(12) United States Patent
Whistler et al.

(10) Patent No.: US 11,248,269 B2
(45) Date of Patent: Feb. 15, 2022

(54) METHODS AND COMPOSITIONS FOR IDENTIFYING PATHOGENIC VIBRIO PARAHAEMOLYTICUS

(71) Applicant: University of New Hampshire, Durham, NH (US)

(72) Inventors: Cheryl Whistler, Durham, NH (US); Jeffrey Allister Hall, Stratham, NH (US); Feng Xu, Guilford, CT (US)

(73) Assignee: UNIVERSITY OF NEW HAMPSHIRE, Durham, NH (US)

( * ) Notice: Subject to any disclaimer, the term of this patent is extended or adjusted under 35 U.S.C. 154(b) by 138 days.

(21) Appl. No.: 15/555,825

(22) PCT Filed: Mar. 5, 2016

(86) PCT No.: PCT/US2016/021089
§ 371 (c)(1),
(2) Date: Sep. 5, 2017

(87) PCT Pub. No.: WO2016/141370
PCT Pub. Date: Sep. 9, 2016

(65) Prior Publication Data
US 2018/0044719 A1    Feb. 15, 2018

Related U.S. Application Data

(60) Provisional application No. 62/128,764, filed on Mar. 5, 2015.

(51) Int. Cl.
| C12Q 1/689 | (2018.01) |
| C12Q 1/68 | (2018.01) |
| C07H 21/04 | (2006.01) |

(52) U.S. Cl.
CPC ....... *C12Q 1/689* (2013.01); *C12Q 2600/136* (2013.01); *C12Q 2600/156* (2013.01); *C12Q 2600/158* (2013.01); *Y02A 50/30* (2018.01)

(58) Field of Classification Search
None
See application file for complete search history.

(56) References Cited

U.S. PATENT DOCUMENTS

| 2003/0176687 A1* | 9/2003 | Ishizuka | ............ | C12Q 1/6865 536/23.7 |
| 2006/0286567 A1 | 12/2006 | Raymond et al. | | |
| 2010/0055506 A1 | 3/2010 | Holland et al. | | |

OTHER PUBLICATIONS

Gonzalez-Escalona (J. Bacterio. Jul. 2011, vol. 193, pp. 3405-3406).*
Mahoney, 2010, Appl Environ Microbiol, 76:7459-7465.*
Whistler, et al. "Use of Whole-Genome Phylogeny and Comparisons for Development of a Multiplex PCR Assay to Identify Sequence Type 36 Vibrio parahaemolyticus" Journal of Clinical Microbiology, Jun. 2015; vol. 53; No. 6; pp. 1864-1872.
Gonzalez-Escalona, et al. "Determination of Molecular Phylogenetics of Vibrio parahaemolyticus Strains by Multilocus Sequence Typing" Journal of Bacteriology; Apr. 2008; vol. 190; No. 8; pp. 2831-2840.
Ahmad, Asim, et al., "Vibrio parahaemolyticus Induced N ecrotizing Fasciitis: An Atypical Organism Causing an Unusual Presentation." Hindawi Publishing Corporation Case Reports in Infectious Diseases vol. 2013, Article ID 216854, 4 pages.
Despaigne, E.Cisneros, et al., "Decontamination of Cuban Oysters Using Irradiation." Institute de Nutrici6n e Higiene de los Alimentos, Cuba, Centro Nacional de Salud Animal, Cuba.
Hara-Kudo, Yukiko, et al., "Decontamination of Vibrio parahaemolyticus in Fish by Washing with Hygienic Seawater and Impacts of the High Level Contamination in the Gills and Viscera." J, Vet, Med, Sci, 75(5): 589- 596, 2013.
Iwamoto, Martha, et al., "Epidemiology of Seafood-Associated Infections in the United States." Clinical Microbiology Reviews, Apr. 2010, p. 399-411.
Kanungo Suman, et al.,"Clinical, epidemiological, and spatial characteristics of Vibrio parahaemolyticus diarrhea and cholera in the urban slums of Kolkata, India." Kanungo et al. BMC Public Health 2012, 12:830 http://www.biomedcentral.com/1471-2458/12/830.
Velazquez-Roman, Jorge et al., "Pandemic Vibrio parahaemolyticus O3:K6 on the American continent." Frontiers in Cellular and Infection Microbiology,Jan. 2014, vol. 3, |Article110, 1.
Ye, Mu, et al., "Effects of pre- or post-processing storage conditions on high-hydrostatic pressure inactivation of Vibrio parahaemolyticus and V. vulnificus in oysters." International Journal of Food Microbiology 163 (2013) 146-152.

\* cited by examiner

*Primary Examiner* — Sarae L Bausch
(74) *Attorney, Agent, or Firm* — Pierce Atwood LLP

(57) ABSTRACT

The invention relates, in part, to methods to identify the presence and/or level of a pathogenic *V. parahaemolyticus* bacterium in a subject or in or on a substrate. Methods are provided that, in part, permit detection of infection of a subject, or contamination of a substrate by pathogenic *V. parahaemolyticus* bacteria.

7 Claims, 6 Drawing Sheets
Specification includes a Sequence Listing.

Distribution of diagnostic loci in draft genomes of *Vibrio parahaemolyticus*[a]

| Strain | Genome Group | Sequence Type | Prp | cps | flp | Isolation Location[b] | Source[c] | Year[d] |
|---|---|---|---|---|---|---|---|---|
| vpV223/04 | n/a | Unk | + | + | + | n/a | n/a | n/a |
| vpS038 | 10329 | 59 | + | + | + | USA | E | 1982 |
| K1203 | 10329 | 59 | + | + | + | AK | E | 2004 |
| K1198 | 10329 | 59 | + | + | + | AK | E | 2004 |
| MDVP40 | 10329 | 36 | + | + | + | MD | C | 2013 |
| MDVP30 | 10329 | 36 | + | + | + | MD | C | 2013 |
| MDVP12 | 10329 | 36 | + | + | + | MD | C | 2012 |
| MDVP32 | 10329 | 36 | + | + | + | MD | C | 2013 |
| MDVP36 | 10329 | 36 | + | + | + | MD | C | 2013 |
| MDVP38 | 10329 | 36 | + | + | + | MD | C | 2013 |
| MDVP33 | 10329 | 36 | + | + | + | MD | C | 2013 |
| MDVP42 | 10329 | 36 | + | + | + | MD | C | 2013 |
| MDVP43 | 10329 | 36 | + | + | + | MD | C | 2013 |
| MAVP-36 | 10329 | 36 | + | + | + | MA | C | 2013 |
| MAVP-26 | 10329 | 36 | + | + | + | MA | C | 2013 |
| MAVP-45 | 10329 | 36 | + | + | + | MA | C | 2013 |
| MAVP-V | 10329 | 36 | + | + | + | MA | C | 2011 |
| 12310 | 10329 | 36 | + | + | + | WA | C | 2016 |
| vp3256 | 10329 | 36 | + | + | + | USA | C | 2007 |
| F11-3A | 10329 | 36 | + | + | + | WA | E | 1988 |
| 48291 | 10329 | 36 | + | + | + | WA | C | 1990 |
| 10296 | 10329 | 36 | + | + | + | WA | C | 1997 |
| NY-3483 | 10329 | 36 | + | + | + | NY | E | 1998 |
| 029-1(b) | 10329 | 36 | + | + | + | OR | E | 1997 |
| 10290 | 10329 | 36 | + | + | + | WA | C | 1997 |
| 48057 | 10329 | 36 | + | + | + | WA | C | 1990 |
| 10329 | 10329 | 36 | + | + | + | WA | C | 1998 |
| CFSAN007462 | 10329 | 36 | + | + | + | MD | C | 2013 |
| vpS037 | 10329 | 36 | + | + | + | USA | C | 1994 |
| MDVP13 | 10329 | 678 | - | + | + | MD | C | 2012 |
| vpS058 | NIHCB0757 | 158 | - | + | + | Japan | C | 1970 |
| Vp970107[e] | S159 | 43 | - | + | - | USA | C | 1997 |
| MDVP28 | S159 | 768 | - | + | - | USA | E | 2010 |
| vpS048 | S048 | 322 | + | - | - | USA | E | 1997 |
| FIM-S1392 | SNUVpS-1 | Unk | + | - | - | Mexico | E | 2014 |
| 10292 | S129 | 50 | - | - | - | WA | C | 1997 |
| MDVP2 | S129 | 651 | - | - | - | MD | C | 2012 |
| MDVP39 | S129 | 896 | - | - | - | MD | C | 2013 |
| VP2007-007 | S100 | 307 | - | - | - | USA | E | 2007 |

Figure 4

| ST | Annotation | Accession number |
|---|---|---|
| 631 | restriction endonuclease | EQM04338 (VP2007-095) |
| 34 | lysR family protein | ETT15213 (Vibrio parahaemolyticus 50, which is also ST34) |
| 674 | Hypothetical protein | WP_053056597 |
| 1127 | Hypothetical protein | KU711831 |
| 36 | Hypothetical protein | WP_047724020<br>Contig: NZ_LBHD01000006<br>locus tag YA91_RS18875 |
| 36 | Orf9 | WP_047724015<br>Contig: NZ_LBHD01000006<br>Locus tag YA91_RS18860 |
| 36 | Orf10 | WP_024701899<br>Contig: NZ_LBHD01000006<br>Locus tag YA91_RS18940 |
| 36 | Hypothetical protein | WP_012842283<br>Contig: NZ_LBHD01000006<br>Locus tag YA91_RS18935 |
| 36 | Orf3 | WP_005477619<br>Contig: NZ_LBHD01000006<br>Locus tag YA91_RS18915 |
| 36 | Orf5 | WP_047715660<br>NZ_LBHE01000002.1<br>Locus tag YA90_RS06390 |
| All above | UreG | EQL83620.1 (VP2007-095)<br>AB831_22120 (MAVP-Q) |
| All above | tdh | EQL83622.1 (vp2007-095)<br>AB831_22110 (MAVP-Q) |

Figure 8

SEQUENCE LISTING

```
<160> NUMBER OF SEQ ID NOS: 175

<210> SEQ ID NO 1
<211> LENGTH: 1992
<212> TYPE: DNA
<213> ORGANISM: Vibrio parahaemolyticus

<400> SEQUENCE: 1
gtgaaaataa aaaacgtacg aattaaaaac tatcgtctgc tcaaagatgt gtcattttcg      60
attgatgaaa aaacaaccat tattgttggg cgtaacaata ctgggaaaac ttcatttgct     120
```

```
gaggcttttc gcagctttct gaatcatgct ggtcccaagg tgcgttatga ggatttcaat      180
caatcctgtc tgtcaggttt cgaagatgcg ctgaatgctc atcaaggcgg agctgaagac      240
gatgttgtga ggcccatgct tccaactatc gagctagagt tacttatcaa ttataaagaa      300
aatgcggacg aatatggtgt cctcggcgac tttattatcg atttttaacga tcaattattt     360 gaaaccatta tcctgatttc ttatcagtta aaagacggca agatcggcga tttttttagt      420
gggctcgata ccatcaaacg aaagcagtat ttttcggatc tgagggcgag gatagagcat      480
tactacgaag ctacagttta cgcggtcgag ccgacaaacc agagcaacaa agcacggctt      540
gagttttcgt catttaaaaa attgctgctg tcgggtctta taaatgcaca acgcggttta      600
gatgacgaaa cgcacaatga acgtgatgtg cttggtaagt cgttaggtaa tattttcaaa      660
agtgcgagta tgttggtgc gccagaagct tttaaggcgc aatcagctga aattcataat       720
gtcgtcgaag gattacaaca agttgttgat actgactttc aggcaagagt gaaagctcta      780
cttcccacct taaatatttt tggatatccg ggtctgcacg atccaaattt aagcgcagca      840
acagagctta atgtgaaatc actgctgaaa agtcacaccc gagtgtttta tcaacgagat      900
gaccatttta cattgccaga aacctataac gggctgggaa tgcggaatct gatctttatc      960
ctcttccgaa tttatgagta tttccgtgag tttcaaagcc atcaaacgcc accgaaaggg     1020
catgtaattt tcatagaaga gcccgaggca catcttcacc cgcaaatgca ggaagtattt     1080
attcgacagc ttgagcaaat tgttgagcag ttccagcgcg aactaaataa ccagcaggtg     1140
tggcctgtac aatttattgt gagtactcat tcctcgcata ttgccaacga agctgatttt     1200
agcaaggttc gttatttcct atccaaaaat ggaaatgaga ccaaagttaa ggatctgggc     1260
gttgctttcc aaagtgccga agcagcgggc gacaaagagt ttttgcataa atacctgacg     1320
ctcacaaaat gcgacctgta ttttgcagac cgagcgatcc tcgttgaagg ggcgactgaa     1380
aggatattgt tgcctcaaat gattaaaaaa gttgacgcag ctttagggac taacttaaga     1440
cagaaatacc tgtcagtcgt cgaaattggt ggagcttatg cacaccactt ctacaaattc     1500
atagatttcc ttgagcttaa aaccctcttt attactgact tagacgcagt tgattcaaaa     1560
caacatcatg ccgctgtaat ggtgagccaa ggggacaggt cgagtaacgt cggcatttca     1620
aaatggtttg gcgaggaggg ttattctgac ttagctacta ttagagctaa agattcagat     1680
tctaaaattc tcggatatcg gcgacttgct tttcaggtag atgaagatgt tagtggttta     1740
tgcggccgca gctttgaaga tgcatttatc ttggttaata gccagttatt ccagctaaat     1800
aacttaactg gttccgcact tgaggccgct gtttatgaca aggcaaaaga tatcggcaaa     1860
aagagcaaag ctgattttgc tattgaatat tgtataagta atacggattg gctcgtcccc     1920
aagtatatcc aagaagggtg cgcatggtta gacgaagacc caacagttgc tgttgaagga     1980
gtgcaatcat ga                                                         1992
```

<210> SEQ ID NO 2
<211> LENGTH: 20
<212> TYPE: DNA
<213> ORGANISM: Vibrio parahaemolyticus

<400> SEQUENCE: 2

```
cggcttgagt tttcgtcatt                                                   20
```

<210> SEQ ID NO 3
<211> LENGTH: 24
<212> TYPE: DNA
<213> ORGANISM: Vibrio parahaemolyticus

<400> SEQUENCE: 3
ccacacctgc tggttattta gttc                                                24

<210> SEQ ID NO 4
<211> LENGTH: 19
<212> TYPE: DNA
<213> ORGANISM: Vibrio parahaemolyticus

<400> SEQUENCE: 4
cccgaggcac atcttcacc                                                      19

<210> SEQ ID NO 5
<211> LENGTH: 25
<212> TYPE: DNA
<213> ORGANISM: Vibrio parahaemolyticus

<400> SEQUENCE: 5
taaaccacta acatcttcat ctacc                                               25

<210> SEQ ID NO 6
<211> LENGTH: 23
<212> TYPE: DNA
<213> ORGANISM: Vibrio parahaemolyticus

<400> SEQUENCE: 6
tgcggaatct gatctttatc ctc                                                 23

<210> SEQ ID NO 7
<211> LENGTH: 23
<212> TYPE: DNA
<213> ORGANISM: Vibrio parahaemolyticus

<400> SEQUENCE: 7
aactgttggg tcttcgtcta acc                                                 23

<210> SEQ ID NO 8
<211> LENGTH: 1590
<212> TYPE: DNA
<213> ORGANISM: Vibrio parahaemolyticus

<400> SEQUENCE: 8
atgttcttga tcatgtctgc ttcttttgtt gatcaagagc tacaatcaga atttgggaaa          60
ataccaccaa gttttttacc tttaggaaat aaaaggcttt ttcaacatca attaaaactg         120
gctccgaaaa acagcattgt ttacctgtca ttaccagagt cattttttat ttcgaataca         180
gatgaaaaat ggctaataaa tcagggagtt agaatcttaa aaataccaga gaatttgagt         240
ttaggagcat cgttagtagc atcgcttaac ctttctgaac ataacctaga ttctccattt         300
agtgttttgt ttggcgatac attattcaat gagttaccag ttggtgaaaa cattatttgt         360
gtttcagaaa gtagtaatag ctacaactgg gctgtagtga cagataatga aatgcactgg         420
cttactgata gtgaaaataa aattgactct aatgtaagaa atattgtcaa cggttatttc         480
cgttttagtt cgccgagaaa tattattcgc tctattactc ggagtaattg ggagtttcta         540
gatgggctta atgaatatca aagataata ggtctcaccg cagtatattc taagcagtgg         600
ttagactttg gtcacgttaa cacttactat aactctaaag ctcatttac tactcaacgt         660 gcttttaatg aattgagaat tacttccgat tatgtagaaa aatcgtcatt taaaagcaat         720
aaaattgcgg cggaagccaa ttggttttca actcttcctt attcactacg aaactatatt         780

```
cctcagtacc taggttctga gaaaaataat gagaaaataa gatataagct tgaatactta    840
tatcttactg cattaaatga gctatatgtg tttagttcat taccagttaa tacttgggag    900
caaattctaa ggcaatgcat cgcatttatt aaagattgcc aacaagaaaa ggcccctaat    960
gattgtaatt ctaaccgttt agttgagttg tttggagata aaactcaagt tcgattgaat   1020
gactattgta atagccagaa tatatctatg tcgacacagt ggatatttaa tggagaagag   1080
aaagtatctt tagaaggtat tttgacggaa actgaacgtt atcttccaaa atcggatgaa   1140
aagaaatggc cattgtgtgt gttacatggt gattttgct ttagtaatgt gctttatgac    1200
tttagatcta atcgtgttaa aactattgat cctagaggta tgaccttaac aggtgaacaa   1260
acaatctatg gcgacattcg atatgatatt gcaaagttaa gtcactcaat cataggtatg   1320
tatgattgga ttattgctgg ttactatgaa gttgatataa agggaaataa tattaatttt   1380
acaattgatg aaagtcatat acaaaaaact attcaacaga gtttatcga gatggtgaaa    1440 gtagaattcg atcttgaagc ttctgaatta atagcaatgc agatccaatt attcttgtct   1500
atgctaccac ttcatcatga tgatattaat cggcaaaaag cactattcgc taatgcgttt   1560
aaattatact ttttaatgaa aaggttgtaa                                    1590

<210> SEQ ID NO 9
<211> LENGTH: 26
<212> TYPE: DNA
<213> ORGANISM: Vibrio parahaemolyticus

<400> SEQUENCE: 9
ttgagaatta cttccgatta tgtaga                                          26

<210> SEQ ID NO 10
<211> LENGTH: 22
<212> TYPE: DNA
<213> ORGANISM: Vibrio parahaemolyticus

<400> SEQUENCE: 10
taaacgcatt agcgaatagt gc                                              22

<210> SEQ ID NO 11
<211> LENGTH: 1254
<212> TYPE: DNA
<213> ORGANISM: Vibrio parahaemolyticus

<400> SEQUENCE: 11
ttagaaacgg tactcggcta agttgttgct actttctagc attttctctg caacatagcg     60
gtgagttgct gttgttggat gcgtgacatc ccagaacaca aacttctcag caccagacgc    120
tgcacactca gagcgcaatg cgtgggtgta catgtaatcg acagacgatg agcggttgat    180
gtccaaacaa ggatcgctcg cgttcacgaa accgtgctct tctggcgcag aagttagcgt    240
ctcgaacaag gcgtgagtat caaacaacgt gatgttgtaa ccttgcgctt tgtagtacat    300
cgcttgtgcc ttgatgaact cgttcatctc aagcactttc gcacgaattt tgtcgatctc    360
ttcttgtgtt gagtacttaa actgaggcgc tttcgtcgcg tctggcagtg tcatcaacat    420
gaagttcttc gcacctgcgt ccgtcaaacg aatcagtgct tctgcataat ctgctttcac    480
ttctggaacg ccacggttgt agttcatgaa gtcattcaaa ccaaactcaa gcgtaaacaa    540 ggtgttttgct ggtttgtagt tcttcgccag ttttgcgtag gttaagtacg aagaaacttg    600
atcaccaacc cctgttagcg cgatgtattg gttctcacca gccgcgccgc caactgccca    660
gttgtagagc ggaaggttct tcgctttggc aatgtattct gtccacacaa aaccgttgga    720
```

```
gaagtgacct aagaaccagc tgttcgggtt agggaagcgc cattgtgatg cgttaaagat      780
gttgcctgta tcagacaagc tgtcaccgag tgcaaccact tgttgatttt gatctggctg      840
cattgctgcg tcgttgctcc agatcgtgtg gttgtatgag aagcgattgt cagcggcgaa      900
gaacgtaatg tctgcgttct cgttcgccaa atctaatgtt gcttcacaac gctgacggat      960
aacgttttgc gacgtgttgg tgtagaacat gtttttaagt gaaacggagc tccaccagta     1020
gccgtcaatg tgaagtagc taccatcttc gttttttgcc cattcccaat cggtcgccgg      1080
atcatctttc gagtagctgg tgcgatacca acagcgaaca taggtatagg tttggttttc     1140
ttgcgtgctg atcacttcag acgctgaaac catttctggt gataaggttg gctcttcggc     1200
aactgcagaa gcaagcggga gtaatgcagt taatagtgtg attgtttttt tcat           1254
```

<210> SEQ ID NO 12
<211> LENGTH: 24
<212> TYPE: DNA
<213> ORGANISM: Vibrio parahaemolyticus

<400> SEQUENCE: 12

```
agaacttcat cttgatgaca ctgc                                              24
```

<210> SEQ ID NO 13
<211> LENGTH: 24
<212> TYPE: DNA
<213> ORGANISM: Vibrio parahaemolyticus

<400> SEQUENCE: 13

```
aaagcggatt atgcagaagc actg                                              24
```

<210> SEQ ID NO 14
<211> LENGTH: 24
<212> TYPE: DNA
<213> ORGANISM: Vibrio parahaemolyticus

<400> SEQUENCE: 14

```
gctactttct agcattttct ctgc                                              24
```

<210> SEQ ID NO 15
<211> LENGTH: 1290
<212> TYPE: DNA
<213> ORGANISM: Vibrio parahaemolyticus

<400> SEQUENCE: 15

```
atgaaagaaa gaatcattaa tctgttctgg ttgtgtttag agcagggggg gagaattctt       60
agttcattct taattacgat tctgatcgtt aagcacctag gggttgaaca gtttggatct      120
tttagtttag ctcttgctat attgacagct ttgggaccct tgctggtct tggatttgac       180 tcgattttat ttaaaaaatt tatcagcaat gaaggagatg aaaagacttt actagggata      240
agctgctttt caagattatt tattgcacta tcgatcatta gtttaactac tttgataaat      300
ttaaacagta atgctgttta tgttaatgta ttaaacatac tcgttctagg ttttctattt      360
gactcatttc tagcatttaa agattatttt cttgctaatc ttaagaataa gttttacaca      420
ttttctactt ttgtttcttc agtgattcaa ttggctcttg tttatacttt agtacaaaaa      480
aatgctagca tagaatactt cgcatggagc tatgtattaa caaagttcat ccaagcgtta      540
gtattaactt gttcatatta taaaattagg caatcattaa tatttccaat ttggaacaaa      600
gagttatcaa gaaaattagt tatagaatct tatccaatga tgctggccgc gtctattggt      660
```

```
ttactttata gtcttcaaga ccaattttttt attaaatact ttcttggtga atacgaactt    720
gggttatact ccgtaggcat taagtttatt ctcattctta tcgtattacc aacactaatc    780
tctaacgtat tttacccaag cttagttaaa aaatttcatt caaataatat tgaaatttat    840
aacaatcaat tgcaggcgat atatttatta ttttcatttt taggtttgtt actatttgcg    900
ttaatgtatt tttcgtcgga aattgtaatt gaaaaattat ttgggactga ttttgaacga    960
tcaagttcta tcatggaaat atattctata ttactggtgg tatcattctt caatctctg    1020 aataataaaa tattaatatt aaataattta caatcagtta tttttaaaag agcagtcttt   1080
gcattaataa caaatgcaat cttgaatctc ttccttatac ctaaatttgg tattaaaggt   1140
gcagcttata gtactgtgtt atcagagatg ttagtattaa ttagttatag cttcagaaaa   1200
gatacaagat ttatttttaa ccatcaaatg agagctatat tttttgttaa tttgttcaaa   1260
attgaaatta taagaagtat taaaagatga                                     1290
```

<210> SEQ ID NO 16
<211> LENGTH: 23
<212> TYPE: DNA
<213> ORGANISM: Vibrio parahaemolyticus

<400> SEQUENCE: 16

```
gtaaaggtct ctgacttttg gac                                              23
```

<210> SEQ ID NO 17
<211> LENGTH: 24
<212> TYPE: DNA
<213> ORGANISM: Vibrio parahaemolyticus

<400> SEQUENCE: 17

```
tggaatagaa ccttcatctt cacc                                             24
```

<210> SEQ ID NO 18
<211> LENGTH: 570
<212> TYPE: DNA
<213> ORGANISM: Vibrio parahaemolyticus

<400> SEQUENCE: 18

```
atgaaactaa aactctactt tgccttcagt ttgctattgg cttcgatatt ttcagtatct     60
aaatcattcg cgattgacct gccatccata ccttttcctt ctccaggttc ggatgagcta    120
ctatttgtcg ttagaaatac aacaataaaa actgaatcac cagttaacgc aatcgttgat    180
gactactgga caaaccgaaa cataaaacga aaccatata aaagcgttca cggtcaatct    240
attttcacga cttcaggctc aaaatggtta agcgcctata tgacggtaaa tattaatgga    300
aataactaca caatggctgc tcttttctgg tataaagatg gccttttcaac ggtcttcaca    360 aaatcagaaa aacaagcct aaatcagaac tattcttctg ttagtgattt cgttggtgag    420
aatgaagaat cattgccaag tgtaacgtat tggatgaaa cgccagaata tttcgtcaat    480
gtcgaagcat atgagagcgg aaatgggcat atgtttgtta tgtgcatttc caataaatca    540
tcatttgatg aatgtatgtc acaaaattaa                                      570
```

<210> SEQ ID NO 19
<211> LENGTH: 25
<212> TYPE: DNA
<213> ORGANISM: Vibrio parahaemolyticus

<400> SEQUENCE: 19

```
cataacaaac atatgcccat ttccg                                            25
```

<210> SEQ ID NO 20
<211> LENGTH: 24
<212> TYPE: DNA
<213> ORGANISM: Vibrio parahaemolyticus

<400> SEQUENCE: 20
ttggcttcga tattttcagt atct                                    24

<210> SEQ ID NO 21
<211> LENGTH: 20
<212> TYPE: DNA
<213> ORGANISM: Vibrio parahaemolyticus

<400> SEQUENCE: 21
gccgaactca aaagcagtaa                                         20

<210> SEQ ID NO 22
<211> LENGTH: 24
<212> TYPE: DNA
<213> ORGANISM: Vibrio parahaemolyticus

<400> SEQUENCE: 22
ggtgtggacg accaataaat caag                                    24

<210> SEQ ID NO 23
<211> LENGTH: 19
<212> TYPE: DNA
<213> ORGANISM: Vibrio parahaemolyticus

<400> SEQUENCE: 23
gggctccgtg tagaagtgg                                          19

<210> SEQ ID NO 24
<211> LENGTH: 25
<212> TYPE: DNA
<213> ORGANISM: Vibrio parahaemolyticus

<400> SEQUENCE: 24
atttggtgat tgtagaagta gatgg                                   25

<210> SEQ ID NO 25
<211> LENGTH: 23
<212> TYPE: DNA
<213> ORGANISM: Vibrio parahaemolyticus

<400> SEQUENCE: 25
acgccttaga ctagaaatag gag                                     23

<210> SEQ ID NO 26
<211> LENGTH: 23
<212> TYPE: DNA
<213> ORGANISM: Vibrio parahaemolyticus

<400> SEQUENCE: 26
ttgacaaccc agaagcagat tgg                                     23

<210> SEQ ID NO 27
<211> LENGTH: 26
<212> TYPE: DNA
<213> ORGANISM: Vibrio parahaemolyticus

<400> SEQUENCE: 27

```
aactcttaat gaaggctaat acatct                                        26

<210> SEQ ID NO 28
<211> LENGTH: 22
<212> TYPE: DNA
<213> ORGANISM: Vibrio parahaemolyticus

<400> SEQUENCE: 28
atttgcgtaa tcgcttatca cg                                            22

<210> SEQ ID NO 29
<211> LENGTH: 24
<212> TYPE: DNA
<213> ORGANISM: Vibrio parahaemolyticus

<400> SEQUENCE: 29
tcttgaagta gaactactgt gacg                                          24

<210> SEQ ID NO 30
<211> LENGTH: 24
<212> TYPE: DNA
<213> ORGANISM: Vibrio parahaemolyticus

<400> SEQUENCE: 30
tttcgcctaa tacgtcttcg tgac                                          24

<210> SEQ ID NO 31
<211> LENGTH: 24
<212> TYPE: DNA
<213> ORGANISM: Vibrio parahaemolyticus

<400> SEQUENCE: 31
cgatgaaaga tcgtaaaaga gacg                                          24

<210> SEQ ID NO 32
<211> LENGTH: 23
<212> TYPE: DNA
<213> ORGANISM: Vibrio parahaemolyticus

<400> SEQUENCE: 32
catttccaga gactgaaaac ctg                                           23

<210> SEQ ID NO 33
<211> LENGTH: 24
<212> TYPE: DNA
<213> ORGANISM: Vibrio parahaemolyticus

<400> SEQUENCE: 33
accttatctt ggaagtagaa gtgg                                          24

<210> SEQ ID NO 34
<211> LENGTH: 25
<212> TYPE: DNA
<213> ORGANISM: Vibrio parahaemolyticus

<400> SEQUENCE: 34
gtattgtttg tatacgggta aaggc                                         25

<210> SEQ ID NO 35
<211> LENGTH: 24
<212> TYPE: DNA
<213> ORGANISM: Vibrio parahaemolyticus

<400> SEQUENCE: 35
```
aaccgaagct ataaaagtca taga                                           24

<210> SEQ ID NO 36
<211> LENGTH: 20
<212> TYPE: DNA
<213> ORGANISM: Vibrio parahaemolyticus

<400> SEQUENCE: 36
tggttgtgtt tagagcaggg                                                20

<210> SEQ ID NO 37
<211> LENGTH: 25
<212> TYPE: DNA
<213> ORGANISM: Vibrio parahaemolyticus

<400> SEQUENCE: 37
tgttggtaat acgataagaa tgaga                                          25

<210> SEQ ID NO 38
<211> LENGTH: 1290
<212> TYPE: DNA
<213> ORGANISM: Vibrio parahaemolyticus

<400> SEQUENCE: 38
atgaaagaaa gaatcattaa tctgttctgg ttgtgtttag agcaggggggg gagaattctt    60
agttcattct taattacgat tctgatcgtt aagcacctag gggttgaaca gtttggatct   120
tttagtttag ctcttgctat attgacagct ttgggacctt ttgctggtct tggatttgac   180
tcgattttat ttaaaaaatt tatcagcaat gaaggagatg aaaagacttt actagggata   240
agctgctttt caagattatt tattgcacta tcgatcatta gtttaactac tttgataaat   300
ttaaacagta atgctgttta tgttaatgta ttaaacatac tcgttctagg ttttctattt   360
gactcatttc tagcatttaa agattatttt cttgctaatc ttaagaataa gttttacaca   420
ttttctactt ttgtttcttc agtgattcaa ttggctcttg tttatacttt agtacaaaaa   480
aatgctagca tagaatactt cgcatggagc tatgtattaa caagttcat ccaagcgtta   540
gtattaactt gttcatatta taaaattagg caatcattaa tatttccaat ttggaacaaa   600
gagttatcaa gaaaattagt tatagaatct tatccaatga tgctggccgc gtctattggt   660
ttactttata gtcttcaaga ccaatttttt attaaatact tcttggtga atacgaactt   720
gggttatact ccgtaggcat taagtttatt ctcattctta tcgtattacc aacactaatc   780
tctaacgtat tttacccaag cttagttaaa aaatttcatt caataatat tgaaatttat   840
aacaatcaat tgcaggcgat atatttatta tttttcattt taggtttgtt actatttgcg   900
ttaatgtatt tttcgtcgga aattgtaatt gaaaaattat ttgggactga ttttgaacga   960
tcaagttcta tcatggaaat atattctata ttactggtgg tatcattctt tcaatctctg  1020
aataataaaa tattaatatt aaataattta caatcagtta tttttaaaag agcagtcttt  1080
gcattaataa caaatgcaat cttgaatctc ttccttatac ctaaatttgg tattaaaggt  1140
gcagcttata gtactgtgtt atcagagatg ttagtattaa ttagttatag cttcagaaaa  1200
gatacaagat ttatttttaa ccatcaaatg agagctatat tttttgttaa tttgttcaaa  1260
attgaaatta taagaagtat taaaagatga                                  1290

<210> SEQ ID NO 39
<211> LENGTH: 20
<212> TYPE: DNA

-continued

<213> ORGANISM: Vibrio parahaemolyticus

<400> SEQUENCE: 39
accaacacaa atctcgtccc                                                    20

<210> SEQ ID NO 40
<211> LENGTH: 25
<212> TYPE: DNA
<213> ORGANISM: Vibrio parahaemolyticus

<400> SEQUENCE: 40
acaaccatta tgctattctt actct                                              25

<210> SEQ ID NO 41
<211> LENGTH: 663
<212> TYPE: PRT
<213> ORGANISM: Vibrio parahaemolyticus

<400> SEQUENCE: 41

```
Met Lys Ile Lys Asn Val Arg Ile Lys Asn Tyr Arg Leu Leu Lys Asp
1               5                   10                  15

Val Ser Phe Ser Ile Asp Glu Lys Thr Thr Ile Ile Val Gly Arg Asn
            20                  25                  30

Asn Thr Gly Lys Thr Ser Phe Ala Glu Ala Phe Arg Ser Phe Leu Asn
        35                  40                  45

His Ala Gly Pro Lys Val Arg Tyr Glu Asp Phe Asn Gln Ser Cys Leu
    50                  55                  60

Ser Gly Phe Glu Asp Ala Leu Asn Ala His Gln Gly Gly Ala Glu Asp
65                  70                  75                  80

Asp Val Val Arg Pro Met Leu Pro Thr Ile Glu Leu Glu Leu Leu Ile
                85                  90                  95

Asn Tyr Lys Glu Asn Ala Asp Glu Tyr Gly Val Leu Gly Asp Phe Ile
            100                 105                 110

Ile Asp Phe Asn Asp Gln Leu Phe Glu Thr Ile Ile Leu Ile Ser Tyr
        115                 120                 125

Gln Leu Lys Asp Gly Lys Ile Gly Asp Phe Phe Ser Gly Leu Asp Thr
130                 135                 140

Ile Lys Arg Lys Gln Tyr Phe Ser Asp Leu Arg Ala Arg Ile Glu His
145                 150                 155                 160

Tyr Tyr Glu Ala Thr Val Tyr Ala Val Glu Pro Thr Asn Gln Ser Asn
                165                 170                 175

Lys Ala Arg Leu Glu Phe Ser Ser Phe Lys Lys Leu Leu Leu Ser Gly
            180                 185                 190

Leu Ile Asn Ala Gln Arg Gly Leu Asp Asp Glu Thr His Asn Glu Arg
        195                 200                 205

Asp Val Leu Gly Lys Ser Leu Gly Asn Ile Phe Lys Ser Ala Ser Ser
    210                 215                 220

Val Gly Ala Pro Glu Ala Phe Lys Ala Gln Ser Ala Glu Ile His Asn
225                 230                 235                 240

Val Val Glu Gly Leu Gln Gln Val Val Asp Thr Asp Phe Gln Ala Arg
                245                 250                 255

Val Lys Ala Leu Leu Pro Thr Leu Asn Ile Phe Gly Tyr Pro Gly Leu
            260                 265                 270

His Asp Pro Asn Leu Ser Ala Ala Thr Glu Leu Asn Val Lys Ser Leu
        275                 280                 285

Leu Glu Ser His Thr Arg Val Phe Tyr Gln Arg Asp Asp His Phe Thr
```

```
        290                 295                 300
Leu Pro Glu Thr Tyr Asn Gly Leu Gly Met Arg Asn Leu Ile Phe Ile
305                 310                 315                 320

Leu Phe Arg Ile Tyr Glu Tyr Phe Arg Glu Phe Gln Ser His Gln Thr
                325                 330                 335

Pro Pro Lys Gly His Val Ile Phe Ile Glu Glu Pro Glu Ala His Leu
                340                 345                 350

His Pro Gln Met Gln Glu Val Phe Ile Arg Gln Leu Glu Gln Ile Val
            355                 360                 365

Glu Gln Phe Gln Arg Glu Leu Asn Asn Gln Gln Val Trp Pro Val Gln
        370                 375                 380

Phe Ile Val Ser Thr His Ser Ser His Ile Ala Asn Glu Ala Asp Phe
385                 390                 395                 400

Ser Lys Val Arg Tyr Phe Leu Ser Lys Asn Gly Asn Glu Thr Lys Val
                405                 410                 415

Lys Asp Leu Gly Val Ala Phe Gln Ser Ala Glu Ala Gly Asp Lys
                420                 425                 430

Glu Phe Leu His Lys Tyr Leu Thr Leu Thr Lys Cys Asp Leu Tyr Phe
            435                 440                 445

Ala Asp Arg Ala Ile Leu Val Glu Gly Ala Thr Glu Arg Ile Leu Leu
        450                 455                 460

Pro Gln Met Ile Lys Lys Val Asp Ala Ala Leu Gly Thr Asn Leu Arg
465                 470                 475                 480

Gln Lys Tyr Leu Ser Val Val Glu Ile Gly Gly Ala Tyr Ala His His
                485                 490                 495

Phe Tyr Lys Phe Ile Asp Phe Leu Glu Leu Lys Thr Leu Phe Ile Thr
                500                 505                 510

Asp Leu Asp Ala Val Asp Ser Lys Gln His His Ala Ala Val Met Val
            515                 520                 525

Ser Gln Gly Asp Arg Ser Ser Asn Val Gly Ile Ser Lys Trp Phe Gly
        530                 535                 540

Glu Gly Tyr Ser Asp Leu Ala Thr Ile Arg Ala Lys Asp Ser Asp
545                 550                 555                 560

Ser Lys Ile Leu Gly Tyr Arg Arg Leu Ala Phe Gln Val Asp Glu Asp
                565                 570                 575

Val Ser Gly Leu Cys Gly Arg Ser Phe Glu Asp Ala Phe Ile Leu Val
            580                 585                 590

Asn Ser Gln Leu Phe Gln Leu Asn Asn Leu Thr Gly Ser Ala Leu Glu
        595                 600                 605

Ala Ala Val Tyr Asp Lys Ala Lys Asp Ile Gly Lys Lys Ser Lys Ala
610                 615                 620

Asp Phe Ala Ile Glu Tyr Cys Ile Ser Asn Thr Asp Trp Leu Val Pro
625                 630                 635                 640

Lys Tyr Ile Gln Glu Gly Cys Ala Trp Leu Asp Glu Asp Pro Thr Val
                645                 650                 655

Ala Val Glu Gly Val Gln Ser
            660

<210> SEQ ID NO 42
<211> LENGTH: 529
<212> TYPE: PRT
<213> ORGANISM: Vibrio parahaemolyticus

<400> SEQUENCE: 42
```

```
Met Phe Leu Ile Met Ser Ala Ser Phe Val Asp Gln Glu Leu Gln Ser
1               5                   10                  15

Glu Phe Gly Lys Ile Pro Pro Ser Phe Leu Pro Leu Gly Asn Lys Arg
            20                  25                  30

Leu Phe Gln His Gln Leu Lys Leu Ala Pro Lys Asn Ser Ile Val Tyr
                35                  40                  45

Leu Ser Leu Pro Glu Ser Phe Phe Ile Ser Asn Thr Asp Glu Lys Trp
            50                  55                  60

Leu Ile Asn Gln Gly Val Arg Ile Leu Lys Ile Pro Glu Asn Leu Ser
65                  70                  75                  80

Leu Gly Ala Ser Leu Val Ala Ser Leu Asn Leu Ser Glu His Asn Leu
                85                  90                  95

Asp Ser Pro Phe Ser Val Leu Phe Gly Asp Thr Leu Phe Asn Glu Leu
            100                 105                 110

Pro Val Gly Glu Asn Ile Ile Cys Val Ser Glu Ser Ser Asn Ser Tyr
                115                 120                 125

Asn Trp Ala Val Val Thr Asp Asn Glu Met His Trp Leu Thr Asp Ser
            130                 135                 140

Glu Asn Lys Ile Asp Ser Asn Val Arg Asn Ile Val Asn Gly Tyr Phe
145                 150                 155                 160

Arg Phe Ser Ser Pro Arg Asn Ile Ile Arg Ser Ile Thr Arg Ser Asn
                165                 170                 175

Trp Glu Phe Leu Asp Gly Leu Asn Glu Tyr His Lys Ile Ile Gly Leu
            180                 185                 190

Thr Ala Val Tyr Ser Lys Gln Trp Leu Asp Phe Gly His Val Asn Thr
                195                 200                 205

Tyr Tyr Asn Ser Lys Ala His Phe Thr Thr Gln Arg Ala Phe Asn Glu
210                 215                 220

Leu Arg Ile Thr Ser Asp Tyr Val Glu Lys Ser Ser Phe Lys Ser Asn
225                 230                 235                 240

Lys Ile Ala Ala Glu Ala Asn Trp Phe Ser Thr Leu Pro Tyr Ser Leu
                245                 250                 255

Arg Asn Tyr Ile Pro Gln Tyr Leu Gly Ser Glu Lys Asn Asn Glu Lys
                260                 265                 270

Ile Arg Tyr Lys Leu Glu Tyr Leu Tyr Leu Thr Ala Leu Asn Glu Leu
            275                 280                 285

Tyr Val Phe Ser Ser Leu Pro Val Asn Thr Trp Glu Gln Ile Leu Arg
            290                 295                 300

Gln Cys Ile Ala Phe Ile Lys Asp Cys Gln Gln Glu Lys Ala Pro Asn
305                 310                 315                 320

Asp Cys Asn Ser Asn Arg Leu Val Glu Leu Phe Gly Asp Lys Thr Gln
                325                 330                 335

Val Arg Leu Asn Asp Tyr Cys Asn Ser Gln Asn Ile Ser Met Ser Thr
                340                 345                 350

Gln Trp Ile Phe Asn Gly Glu Glu Lys Val Ser Leu Glu Gly Ile Leu
            355                 360                 365

Thr Glu Thr Glu Arg Tyr Leu Pro Lys Ser Asp Glu Lys Lys Trp Pro
370                 375                 380

Leu Cys Val Leu His Gly Asp Phe Cys Phe Ser Asn Val Leu Tyr Asp
385                 390                 395                 400

Phe Arg Ser Asn Arg Val Lys Thr Ile Asp Pro Arg Gly Met Thr Leu
                405                 410                 415

Thr Gly Glu Gln Thr Ile Tyr Gly Asp Ile Arg Tyr Asp Ile Ala Lys
```

```
                    420             425             430
Leu Ser His Ser Ile Ile Gly Met Tyr Asp Trp Ile Ile Ala Gly Tyr
            435                 440                 445

Tyr Glu Val Asp Ile Lys Gly Asn Asn Ile Asn Phe Thr Ile Asp Glu
            450                 455                 460

Ser His Ile Gln Lys Thr Ile Gln Gln Lys Phe Ile Glu Met Val Lys
465                 470                 475                 480

Val Glu Phe Asp Leu Glu Ala Ser Glu Leu Ile Ala Met Gln Ile Gln
                485                 490                 495

Leu Phe Leu Ser Met Leu Pro Leu His His Asp Asp Ile Asn Arg Gln
                500                 505                 510

Lys Ala Leu Phe Ala Asn Ala Phe Lys Leu Tyr Phe Leu Met Lys Arg
                515                 520                 525

Leu

<210> SEQ ID NO 43
<211> LENGTH: 417
<212> TYPE: PRT
<213> ORGANISM: Vibrio parahaemolyticus

<400> SEQUENCE: 43

Met Lys Lys Thr Ile Thr Leu Leu Thr Ala Leu Leu Pro Leu Ala Ser
1               5                   10                  15

Ala Val Ala Glu Glu Pro Thr Leu Ser Pro Glu Met Val Ser Ala Ser
                20                  25                  30

Glu Val Ile Ser Thr Gln Glu Asn Gln Thr Tyr Thr Tyr Val Arg Cys
            35                  40                  45

Trp Tyr Arg Thr Ser Tyr Ser Lys Asp Asp Pro Ala Thr Asp Trp Glu
        50                  55                  60

Trp Ala Lys Asn Glu Asp Gly Ser Tyr Phe Thr Ile Asp Gly Tyr Trp
65                  70                  75                  80

Trp Ser Ser Val Ser Leu Lys Asn Met Phe Tyr Thr Asn Thr Ser Gln
                85                  90                  95

Asn Val Ile Arg Gln Arg Cys Glu Ala Thr Leu Asp Leu Ala Asn Glu
            100                 105                 110

Asn Ala Asp Ile Thr Phe Phe Ala Ala Asp Asn Arg Phe Ser Tyr Asn
        115                 120                 125

His Thr Ile Trp Ser Asn Asp Ala Ala Met Gln Pro Asp Gln Ile Asn
130                 135                 140

Lys Val Val Ala Leu Gly Asp Ser Leu Ser Asp Thr Gly Asn Ile Phe
145                 150                 155                 160

Asn Ala Ser Gln Trp Arg Phe Pro Asn Pro Asn Ser Trp Phe Leu Gly
                165                 170                 175

His Phe Ser Asn Gly Phe Val Trp Thr Glu Tyr Ile Ala Lys Ala Lys
            180                 185                 190

Asn Leu Pro Leu Tyr Asn Trp Ala Val Gly Gly Ala Ala Gly Glu Asn
        195                 200                 205

Gln Tyr Ile Ala Leu Thr Gly Val Gly Asp Gln Val Ser Ser Tyr Leu
    210                 215                 220

Thr Tyr Ala Lys Leu Ala Lys Asn Tyr Lys Pro Ala Asn Thr Leu Phe
225                 230                 235                 240

Thr Leu Glu Phe Gly Leu Asn Asp Phe Met Asn Tyr Asn Arg Gly Val
                245                 250                 255

Pro Glu Val Lys Ala Asp Tyr Ala Glu Ala Leu Ile Arg Leu Thr Asp
```

```
                260                 265                 270
Ala Gly Ala Lys Asn Phe Met Leu Met Thr Leu Pro Asp Ala Thr Lys
            275                 280                 285

Ala Pro Gln Phe Lys Tyr Ser Thr Gln Glu Ile Asp Lys Ile Arg
        290                 295                 300

Ala Lys Val Leu Glu Met Asn Glu Phe Ile Lys Ala Gln Ala Met Tyr
305                 310                 315                 320

Tyr Lys Ala Gln Gly Tyr Asn Ile Thr Leu Phe Asp Thr His Ala Leu
                325                 330                 335

Phe Glu Thr Leu Thr Ser Ala Pro Glu Glu His Gly Phe Val Asn Ala
            340                 345                 350

Ser Asp Pro Cys Leu Asp Ile Asn Arg Ser Ser Val Asp Tyr Met
        355                 360                 365

Tyr Thr His Ala Leu Arg Ser Glu Cys Ala Ala Ser Gly Ala Glu Lys
        370                 375                 380

Phe Val Phe Trp Asp Val Thr His Pro Thr Thr Ala Thr His Arg Tyr
385                 390                 395                 400

Val Ala Glu Lys Met Leu Glu Ser Ser Asn Asn Leu Ala Glu Tyr Arg
                405                 410                 415

Phe

<210> SEQ ID NO 44
<211> LENGTH: 174
<212> TYPE: PRT
<213> ORGANISM: Vibrio parahaemolyticus

<400> SEQUENCE: 44

Met Leu Ala Ala Phe Lys Thr Phe Ala Phe Glu Leu Pro Ser Val Pro
1               5                   10                  15

Phe Pro Ala Pro Gly Ser Asp Glu Ile Leu Phe Val Val Arg Asp Ala
            20                  25                  30

Thr Phe Asn Thr Asn Ala Pro Val Asn Val Lys Val Ser Asp Phe Trp
        35                  40                  45

Thr Asn Arg Asn Val Lys Arg Lys Pro Tyr Lys Asp Val Tyr Gly Gln
    50                  55                  60

Ser Val Phe Thr Thr Ser Gly Thr Lys Trp Leu Thr Ser Tyr Met Thr
65                  70                  75                  80

Val Asn Ile Asn Asp Lys Asp Tyr Thr Met Ala Ala Val Ser Gly Tyr
                85                  90                  95

Lys Arg Gly His Ser Ala Val Phe Val Lys Ser Asp Gln Val Gln Leu
            100                 105                 110

Gln His Ser Tyr Asn Ser Val Ala Asn Phe Val Gly Glu Asp Glu Asp
        115                 120                 125

Ser Ile Pro Ser Lys Met Tyr Leu Asp Glu Thr Pro Glu Tyr Phe Val
    130                 135                 140

Asn Val Glu Ala Tyr Glu Ser Gly Ser Gly Asn Ile Leu Val Met Cys
145                 150                 155                 160

Ile Ser Asn Lys Glu Ser Phe Phe Glu Cys Glu His Gln Lys
                165                 170

<210> SEQ ID NO 45
<211> LENGTH: 189
<212> TYPE: PRT
<213> ORGANISM: Vibrio parahaemolyticus

<400> SEQUENCE: 45
```

Met Lys Leu Lys Leu Tyr Phe Ala Phe Ser Leu Leu Ala Ser Ile
1               5                   10                  15

Phe Ser Val Ser Lys Ser Phe Ala Ile Asp Leu Pro Ser Ile Pro Phe
            20                  25                  30

Pro Ser Pro Gly Ser Asp Glu Leu Leu Phe Val Val Arg Asn Thr Thr
            35                  40                  45

Ile Lys Thr Glu Ser Pro Val Asn Ala Ile Val Asp Asp Tyr Trp Thr
50                  55                  60

Asn Arg Asn Ile Lys Arg Lys Pro Tyr Lys Ser Val His Gly Gln Ser
65                  70                  75                  80

Ile Phe Thr Thr Ser Gly Ser Lys Trp Leu Ser Ala Tyr Met Thr Val
                85                  90                  95

Asn Ile Asn Gly Asn Asn Tyr Thr Met Ala Ala Leu Ser Gly Tyr Lys
                100                 105                 110

Asp Gly Leu Ser Thr Val Phe Thr Lys Ser Glu Lys Thr Ser Leu Asn
            115                 120                 125

Gln Asn Tyr Ser Ser Val Ser Asp Phe Val Gly Glu Asn Glu Glu Ser
            130                 135                 140

Leu Pro Ser Val Thr Tyr Leu Asp Glu Thr Pro Glu Tyr Phe Val Asn
145                 150                 155                 160

Val Glu Ala Tyr Glu Ser Gly Asn Gly His Met Phe Val Met Cys Ile
                165                 170                 175

Ser Asn Lys Ser Ser Phe Asp Glu Cys Met Ser Gln Asn
            180                 185

<210> SEQ ID NO 46
<211> LENGTH: 429
<212> TYPE: PRT
<213> ORGANISM: Vibrio parahaemolyticus

<400> SEQUENCE: 46

Met Lys Glu Arg Ile Ile Asn Leu Phe Trp Leu Cys Leu Glu Gln Gly
1               5                   10                  15

Gly Arg Ile Leu Ser Ser Phe Leu Ile Thr Ile Leu Ile Val Lys His
            20                  25                  30

Leu Gly Val Glu Gln Phe Gly Ser Phe Ser Leu Ala Leu Ala Ile Leu
            35                  40                  45

Thr Ala Leu Gly Pro Phe Ala Gly Leu Gly Phe Asp Ser Ile Leu Phe
50                  55                  60

Lys Lys Phe Ile Ser Asn Glu Gly Asp Glu Lys Thr Leu Leu Gly Ile
65                  70                  75                  80

Ser Cys Phe Ser Arg Leu Phe Ile Ala Leu Ser Ile Ile Ser Leu Thr
                85                  90                  95

Thr Leu Ile Asn Leu Asn Ser Asn Ala Val Tyr Val Asn Val Leu Asn
                100                 105                 110

Ile Leu Val Leu Gly Phe Leu Phe Asp Ser Phe Leu Ala Phe Lys Asp
            115                 120                 125

Tyr Phe Leu Ala Asn Leu Lys Asn Lys Phe Tyr Thr Phe Ser Thr Phe
            130                 135                 140

Val Ser Ser Val Ile Gln Leu Ala Leu Val Tyr Thr Leu Val Gln Lys
145                 150                 155                 160

Asn Ala Ser Ile Glu Tyr Phe Ala Trp Ser Tyr Val Leu Thr Lys Phe
                165                 170                 175

Ile Gln Ala Leu Val Leu Thr Cys Ser Tyr Tyr Lys Ile Arg Gln Ser

```
                180                 185                 190
Leu Ile Phe Pro Ile Trp Asn Lys Glu Leu Ser Arg Lys Leu Val Ile
            195                 200                 205

Glu Ser Tyr Pro Met Met Leu Ala Ala Ser Ile Gly Leu Leu Tyr Ser
        210                 215                 220

Leu Gln Asp Gln Phe Phe Ile Lys Tyr Phe Leu Gly Glu Tyr Glu Leu
225                 230                 235                 240

Gly Leu Tyr Ser Val Gly Ile Lys Phe Ile Leu Ile Leu Ile Val Leu
                245                 250                 255

Pro Thr Leu Ile Ser Asn Val Phe Tyr Pro Ser Leu Val Lys Lys Phe
            260                 265                 270

His Ser Asn Asn Ile Glu Ile Tyr Asn Asn Gln Leu Gln Ala Ile Tyr
        275                 280                 285

Leu Leu Phe Phe Ile Leu Gly Leu Leu Leu Phe Ala Leu Met Tyr Phe
    290                 295                 300

Ser Ser Glu Ile Val Ile Glu Lys Leu Phe Gly Thr Asp Phe Glu Arg
305                 310                 315                 320

Ser Ser Ser Ile Met Glu Ile Tyr Ser Ile Leu Leu Val Ser Phe
                325                 330                 335

Phe Gln Ser Leu Asn Asn Lys Ile Leu Ile Leu Asn Asn Leu Gln Ser
            340                 345                 350

Val Ile Phe Lys Arg Ala Val Phe Ala Leu Ile Thr Asn Ala Ile Leu
        355                 360                 365

Asn Leu Phe Leu Ile Pro Lys Phe Gly Ile Lys Gly Ala Ala Tyr Ser
    370                 375                 380

Thr Val Leu Ser Glu Met Leu Val Leu Ile Ser Tyr Ser Phe Arg Lys
385                 390                 395                 400

Asp Thr Arg Phe Ile Phe Asn His Gln Met Arg Ala Ile Phe Phe Val
                405                 410                 415

Asn Leu Phe Lys Ile Glu Ile Ile Arg Ser Ile Lys Arg
            420                 425

<210> SEQ ID NO 47
<211> LENGTH: 21
<212> TYPE: DNA
<213> ORGANISM: Vibrio parahaemolyticus

<400> SEQUENCE: 47
aggacgcagt tacgcttgat g                                    21

<210> SEQ ID NO 48
<211> LENGTH: 22
<212> TYPE: DNA
<213> ORGANISM: Vibrio parahaemolyticus

<400> SEQUENCE: 48
ctaacgcatt gtccctttgt ag                                   22

<210> SEQ ID NO 49
<211> LENGTH: 21
<212> TYPE: DNA
<213> ORGANISM: Vibrio parahaemolyticus

<400> SEQUENCE: 49
tcctgcgtca atgcgaacta c                                    21

<210> SEQ ID NO 50
```

```
<211> LENGTH: 22
<212> TYPE: DNA
<213> ORGANISM: Vibrio parahaemolyticus

<400> SEQUENCE: 50
gattgcgtaa cagggaaaca tc                                              22

<210> SEQ ID NO 51
<211> LENGTH: 20
<212> TYPE: DNA
<213> ORGANISM: Vibrio parahaemolyticus

<400> SEQUENCE: 51
ttgcgtaaca gggaaacatc                                                 20

<210> SEQ ID NO 52
<211> LENGTH: 20
<212> TYPE: DNA
<213> ORGANISM: Vibrio parahaemolyticus

<400> SEQUENCE: 52
gattgcgtaa cagggaaaca                                                 20

<210> SEQ ID NO 53
<211> LENGTH: 26
<212> TYPE: DNA
<213> ORGANISM: Vibrio parahaemolyticus

<400> SEQUENCE: 53
agttcatcag gtagagagtt agagga                                          26

<210> SEQ ID NO 54
<211> LENGTH: 24
<212> TYPE: DNA
<213> ORGANISM: Vibrio parahaemolyticus

<400> SEQUENCE: 54
tcttcgttac catagtatga gcca                                            24

<210> SEQ ID NO 55
<211> LENGTH: 26
<212> TYPE: DNA
<213> ORGANISM: Vibrio parahaemolyticus

<400> SEQUENCE: 55
tcaagtagtc catctctcaa tctcct                                          26

<210> SEQ ID NO 56
<211> LENGTH: 24
<212> TYPE: DNA
<213> ORGANISM: Vibrio parahaemolyticus

<400> SEQUENCE: 56
agaagcaatg gtatcatact cggt                                            24

<210> SEQ ID NO 57
<211> LENGTH: 792
<212> TYPE: DNA
<213> ORGANISM: Vibrio parahaemolyticus

<400> SEQUENCE: 57
agttcatcag gtagagagtt agaggaatat gtacagagta cgtatcgctt tcttctaaat     60
atgaaagatg aaggtgtaac tgtagagcga aatatatact tatctggaaa gtctggagcc   120
```

```
aaacatcaaa ttgatgtctt ttatgagttt aaaacagctg gtattacaca tagggtagct      180
attgaatgta aagaccactc acgcccagtg gaaaaaggga aggttcaaga gtttgcatat      240
aaactgcaag atatcggtgg gatttctggt gtcatggtat ctcaagcagg gtatcaatca      300
ggcgctgaat tgattgctaa gcaggcagat atcctgctga aaactactga tgaacttcct      360
cctactcctt ggttaatggc tgagaggttg gaaagtgtag ctcttccaac agaaaattac      420
aggggggaac cattttgggt gatcatggag catagtgaag gtaaagttaa tggctcatac      480
tatggtaacg aagataatgg tcgtaagttc ataccttttgt ttttctccaa atatcatgct      540
caactaaatt ttgatgaagg tggacttgat gaatcttgtt ggtgtgttcg tggtttacca      600
aggcacgctt ttagggcatt tttgctgtta ctagaattat ttgagcgcca aaaggtcgag      660
cctatgatct gttttagacc tcctggcgat actagtgaaa taggctgggc agggttagtt      720
actacacgtg acttacttgt aaaagagtac tattgtgaag atctgcctag agtgctaaac      780
aaatccgctt aa                                                         792

<210> SEQ ID NO 58
<211> LENGTH: 264
<212> TYPE: PRT
<213> ORGANISM: Vibrio parahaemolyticus

<400> SEQUENCE: 58

Met Ser Ser Ser Gly Arg Glu Leu Glu Glu Tyr Val Gln Ser Thr Tyr
1               5                   10                  15

Arg Phe Leu Leu Asn Met Lys Asp Glu Gly Val Thr Val Glu Arg Asn
            20                  25                  30

Ile Tyr Leu Ser Gly Lys Ser Gly Ala Lys His Gln Ile Asp Val Phe
        35                  40                  45

Tyr Glu Phe Lys Thr Ala Gly Ile Thr His Arg Val Ala Ile Glu Cys
    50                  55                  60

Lys Asp His Ser Arg Pro Val Glu Lys Gly Lys Val Gln Glu Phe Ala
65                  70                  75                  80

Tyr Lys Leu Gln Asp Ile Gly Gly Ile Ser Gly Val Met Val Ser Gln
                85                  90                  95

Ala Gly Tyr Gln Ser Gly Ala Glu Leu Ile Ala Lys Gln Ala Asp Ile
            100                 105                 110

Leu Leu Lys Thr Thr Asp Glu Leu Pro Pro Thr Pro Trp Leu Met Ala
        115                 120                 125

Glu Arg Leu Glu Ser Val Ala Leu Pro Thr Glu Asn Tyr Arg Gly Glu
    130                 135                 140

Pro Phe Trp Val Ile Met Glu His Ser Glu Gly Lys Val Asn Gly Ser
145                 150                 155                 160

Tyr Tyr Gly Asn Glu Asp Asn Gly Arg Lys Phe Ile Pro Leu Phe Phe
                165                 170                 175

Ser Lys Tyr His Ala Gln Leu Asn Phe Asp Glu Gly Gly Leu Asp Glu
            180                 185                 190

Ser Cys Trp Cys Val Arg Gly Leu Pro Arg His Ala Phe Arg Ala Phe
        195                 200                 205

Leu Leu Leu Leu Glu Leu Phe Glu Arg Gln Lys Val Glu Pro Met Ile
    210                 215                 220

Cys Phe Arg Pro Pro Gly Asp Thr Ser Glu Ile Gly Trp Ala Gly Leu
225                 230                 235                 240

Val Thr Thr Arg Asp Leu Leu Val Lys Glu Tyr Tyr Cys Glu Asp Leu
```

```
                  245                 250                 255
Pro Arg Val Leu Asn Lys Ser Ala
        260

<210> SEQ ID NO 59
<211> LENGTH: 17
<212> TYPE: DNA
<213> ORGANISM: Vibrio parahaemolyticus

<400> SEQUENCE: 59
tgggcgttag gctttgc                                                   17

<210> SEQ ID NO 60
<211> LENGTH: 21
<212> TYPE: DNA
<213> ORGANISM: Vibrio parahaemolyticus

<400> SEQUENCE: 60
gggcttctac gactttctgc t                                              21

<210> SEQ ID NO 61
<211> LENGTH: 17
<212> TYPE: DNA
<213> ORGANISM: Vibrio parahaemolyticus

<400> SEQUENCE: 61
acccgcaatc cgaaacg                                                   17

<210> SEQ ID NO 62
<211> LENGTH: 21
<212> TYPE: DNA
<213> ORGANISM: Vibrio parahaemolyticus

<400> SEQUENCE: 62
cccgaagatg ctgaaagacg a                                              21

<210> SEQ ID NO 63
<211> LENGTH: 25
<212> TYPE: DNA
<213> ORGANISM: Vibrio parahaemolyticus

<400> SEQUENCE: 63
tccttgttgt cgttgaatat cagtc                                          25

<210> SEQ ID NO 64
<211> LENGTH: 24
<212> TYPE: DNA
<213> ORGANISM: Vibrio parahaemolyticus

<400> SEQUENCE: 64
gatacggttg tcatgcctat gtgt                                           24

<210> SEQ ID NO 65
<211> LENGTH: 25
<212> TYPE: DNA
<213> ORGANISM: Vibrio parahaemolyticus

<400> SEQUENCE: 65
aggaacaaca gcaacttata gtcag                                          25

<210> SEQ ID NO 66
<211> LENGTH: 24
<212> TYPE: DNA
```

<213> ORGANISM: Vibrio parahaemolyticus

<400> SEQUENCE: 66
ctatgccaac agtacggata caca        24

<210> SEQ ID NO 67
<211> LENGTH: 858
<212> TYPE: DNA
<213> ORGANISM: Vibrio parahaemolyticus

<400> SEQUENCE: 67

```
atggatttga acttaatcaa tactttcctt gttgtcgttg aatatcagtc gtataccaaa      60
gcggcggaac acttaggggt aacacaaccc gcaattagtg catcgatgaa acgactagaa     120
caactatcta acaaaaatct ttttgttaga aaagggcgaa atattgagtt gacctcaacc     180
gcacaccact gggttccatt attcagacga gcattaagca taattaatga tgctgtcatt     240
gagcaagcca catttcaagt ctgctgtacc gaaccctctt tttcgagact gaccgcgtct     300
ccaagctttt cgttgcgttg cgctcctgtt tcgtccctct ccttacttga cgatcttcgt     360
ctacacaaag tggacttggt tattgacaac ctccccacta tagaaacctc atttgtatgt     420
gagttggtat acgaagagcc aattgtggtg atttgccgtc aaggacatcc acgtataact     480
ggcagtacat ttaactcatc aatgttctat gccgaacaac actgtgtatt ggttgatacg     540
gaatatcggg cagtgaatct tggtggggcg ctcctcgacc ctacacaaca tttacacata     600
ggcatgacaa ccgtatctct atctggaatg gtactgaacg tatctaagct agactacctt     660
ggaatcttgc cactctcttt tgctagagaa tggcaggatt ctcttaaact acaaatattg     720
ccatgtccca taaaaagtca atctattggt tataatatga tttatcacaa aagagatgaa     780
cataatgttg cccaccaaaa actgagaagg caaattcgtc acgacctcgt tcaaaacttg     840
atggttagga atttctga                                                  858
```

<210> SEQ ID NO 68
<211> LENGTH: 285
<212> TYPE: PRT
<213> ORGANISM: Vibrio parahaemolyticus

<400> SEQUENCE: 68

```
Met Asp Leu Asn Leu Ile Asn Thr Phe Leu Val Val Val Glu Tyr Gln
1               5                   10                  15

Ser Tyr Thr Lys Ala Ala Glu His Leu Gly Val Thr Gln Pro Ala Ile
            20                  25                  30

Ser Ala Ser Met Lys Arg Leu Glu Gln Leu Ser Asn Lys Asn Leu Phe
        35                  40                  45

Val Arg Lys Gly Arg Asn Ile Glu Leu Thr Ser Thr Ala His His Trp
    50                  55                  60

Val Pro Leu Phe Arg Arg Ala Leu Ser Ile Ile Asn Asp Ala Val Ile
65                  70                  75                  80

Glu Gln Ala Thr Phe Gln Val Cys Cys Thr Glu Pro Ser Phe Ser Arg
                85                  90                  95

Leu Thr Ala Ser Pro Ser Phe Ser Leu Arg Cys Ala Pro Val Ser Ser
            100                 105                 110

Leu Ser Leu Leu Asp Asp Leu Arg Leu His Lys Val Asp Leu Val Ile
        115                 120                 125

Asp Asn Leu Pro Thr Ile Glu Thr Ser Phe Val Cys Glu Leu Val Tyr
    130                 135                 140
```

```
Glu Glu Pro Ile Val Val Ile Cys Arg Gln Gly His Pro Arg Ile Thr
145                 150                 155                 160

Gly Ser Thr Phe Asn Ser Ser Met Phe Tyr Ala Glu Gln His Cys Val
                165                 170                 175

Leu Val Asp Thr Glu Tyr Arg Ala Val Asn Leu Gly Gly Ala Leu Leu
            180                 185                 190

Asp Pro Thr Gln His Leu His Ile Gly Met Thr Thr Val Ser Leu Ser
        195                 200                 205

Gly Met Val Leu Asn Val Ser Lys Leu Asp Tyr Leu Gly Ile Leu Pro
    210                 215                 220

Leu Ser Phe Ala Arg Glu Trp Gln Asp Ser Leu Lys Leu Gln Ile Leu
225                 230                 235                 240

Pro Cys Pro Ile Lys Ser Gln Ser Ile Gly Tyr Asn Met Ile Tyr His
                245                 250                 255

Lys Arg Asp Glu His Asn Val Ala His Gln Lys Leu Arg Arg Gln Ile
                260                 265                 270

Arg His Asp Leu Val Gln Asn Leu Met Val Arg Asn Phe
        275                 280                 285

<210> SEQ ID NO 69
<211> LENGTH: 22
<212> TYPE: DNA
<213> ORGANISM: Vibrio parahaemolyticus

<400> SEQUENCE: 69
gaagatggtc caagagggaa gc                                             22

<210> SEQ ID NO 70
<211> LENGTH: 23
<212> TYPE: DNA
<213> ORGANISM: Vibrio parahaemolyticus

<400> SEQUENCE: 70
ctatcagaga ttgagcaagt agc                                            23

<210> SEQ ID NO 71
<211> LENGTH: 22
<212> TYPE: DNA
<213> ORGANISM: Vibrio parahaemolyticus

<400> SEQUENCE: 71
cttctaccag gttctccctt cg                                             22

<210> SEQ ID NO 72
<211> LENGTH: 23
<212> TYPE: DNA
<213> ORGANISM: Vibrio parahaemolyticus

<400> SEQUENCE: 72
gatagtctct aactcgttca tcg                                            23

<210> SEQ ID NO 73
<211> LENGTH: 447
<212> TYPE: DNA
<213> ORGANISM: Vibrio parahaemolyticus

<400> SEQUENCE: 73
gaagatggtc caagagggaa gcatagtctc cctctttcaa aaagggataa tttagaaaat    60
ctggttttac tttgtaaaac gcatcataaa ttagttgacg atcacgtaga tgagttttcg   120
```

```
gttagtgatt tgacaacact gagagaggag cactttaaat gggtgtcaaa taagttaaat    180
gagcctaggc aatgggagtg taacttaagt cagcttactt atattaatgt acctcgatta    240
tcgatgttat cttctaggtt gggctatgaa gtagatttag atgaatacgg taagtttgaa    300
acattatatt cactgcgttg gtcgcttaat aaattgatga ggcaatttct atcaacatta    360
aacaagataa acgtgaatac attggacttt cctctgttaa ctatcccga tatccggttg    420 gttggagcta cttgctcaat ctctgat                                       447
```

<210> SEQ ID NO 74
<211> LENGTH: 415
<212> TYPE: PRT
<213> ORGANISM: Vibrio parahaemolyticus

<400> SEQUENCE: 74

```
Met Ala Val Leu Glu Lys Thr Arg Asn Met Leu Trp Ala Leu Ser Ala
1               5                   10                  15

Gly Arg Cys Ala Tyr Cys Lys Asn Lys Leu Val Val Glu Ser Lys Lys
            20                  25                  30

Lys Asn Phe Ser Leu Val Gly Glu Val Ala His Ile Val Ala Gln Lys
        35                  40                  45

Glu Asp Gly Pro Arg Gly Lys His Ser Leu Pro Leu Ser Lys Arg Asp
    50                  55                  60

Asn Leu Glu Asn Leu Val Leu Cys Lys Thr His His Lys Leu Val
65                  70                  75                  80

Asp Asp His Val Asp Glu Phe Ser Val Ser Asp Leu Thr Thr Leu Arg
                85                  90                  95

Glu Glu His Phe Lys Trp Val Ser Asn Lys Leu Asn Glu Pro Arg Gln
            100                 105                 110

Trp Glu Cys Asn Leu Ser Gln Leu Thr Tyr Ile Asn Val Pro Arg Leu
        115                 120                 125

Ser Met Leu Ser Ser Arg Leu Gly Tyr Glu Val Asp Leu Asp Glu Tyr
    130                 135                 140

Gly Lys Phe Glu Thr Leu Tyr Ser Leu Arg Trp Ser Leu Asn Lys Leu
145                 150                 155                 160

Met Arg Gln Phe Leu Ser Thr Leu Asn Lys Ile Asn Val Asn Thr Leu
                165                 170                 175

Asp Phe Ser Ser Val Asn Tyr Pro Asp Ile Arg Leu Val Gly Ala Thr
            180                 185                 190

Cys Ser Ile Ser Asp Ser Phe Arg Thr Lys Asn Val Pro Met Ile Gly
        195                 200                 205

Arg Asp Asp Lys Asp Pro Val Thr Phe Cys Gly Asp Leu Lys Lys Asp
    210                 215                 220

Pro His Ile Tyr Lys Lys Tyr Pro Asn Phe Lys Leu Val Met Arg Ile
225                 230                 235                 240

Gln Pro Ser Trp Ile Thr Thr Ser Thr Ala Phe Leu Ala Phe Arg Pro
                245                 250                 255

Ser Gly Gly Val Ser Thr Phe Ser Gly Leu Ile Thr Val Ser Glu Val
            260                 265                 270

Asp Val Glu Asn Ser Val Ile Tyr Ala Ile Pro Leu Val Leu Gly Leu
        275                 280                 285

Pro Val Ser Asp Phe Glu Leu Met Met Lys Glu Pro Lys Leu Phe Arg
    290                 295                 300

Glu Glu Asp Ser Ser Val Val Gly Lys Lys Ile Asn Lys Lys Thr Ser
305                 310                 315                 320
```

```
Leu Ile Glu Phe Glu Asp Leu Glu Lys Ala Ile Glu Gln Asp Thr Lys
                325                 330                 335

Tyr Val Asn Pro Pro Asp Cys Cys Asp Val Cys Arg Ala Ser Leu Glu
            340                 345                 350

Asn Gln Thr Tyr Phe Val Asp Gly Ala Ile Lys Ser Ser Ala Trp
        355                 360                 365

Ala Phe Leu Cys Glu Tyr Cys Phe Glu Lys Asp Gly Val Gly Ile Gly
    370                 375                 380

Trp Gly Leu Gly Gln Leu Phe Lys Lys Asn Lys His Asn Glu Trp Leu
385                 390                 395                 400

Leu Val Gly Gly Phe Ala Pro Glu Ser Asp Asp Tyr Tyr Ile
                405                 410                 415

<210> SEQ ID NO 75
<211> LENGTH: 22
<212> TYPE: DNA
<213> ORGANISM: Vibrio parahaemolyticus

<400> SEQUENCE: 75
cgtaaagtaa aagagcctgg tc                                          22

<210> SEQ ID NO 76
<211> LENGTH: 19
<212> TYPE: DNA
<213> ORGANISM: Vibrio parahaemolyticus

<400> SEQUENCE: 76
ttcagttccc cgcattcat                                              19

<210> SEQ ID NO 77
<211> LENGTH: 22
<212> TYPE: DNA
<213> ORGANISM: Vibrio parahaemolyticus

<400> SEQUENCE: 77
gcatttcatt ttctcggacc ag                                          22

<210> SEQ ID NO 78
<211> LENGTH: 19
<212> TYPE: DNA
<213> ORGANISM: Vibrio parahaemolyticus

<400> SEQUENCE: 78
aagtcaaggg gcgtaagta                                              19

<210> SEQ ID NO 79
<211> LENGTH: 1234
<212> TYPE: DNA
<213> ORGANISM: Vibrio parahaemolyticus

<400> SEQUENCE: 79
cgtaaagtaa aagagcctgg tcttgcatcc accggaatta atctatcttt taggttaata   60
gtacgaacaa actcaccgta tagggatgac caaccatcta gcactttaga aatgctgttt  120
agttgcatag tccctcgacg actaggacga gaaatgtgaa tttcgtgatt tacagataga  180
attgattctt cgatttcttc cgactcaatg tcttctattc tgaagtcgca tggtggaaga  240
tcctcttctg ggatatcttc tgcagctaag atctcaatat tatggttatt accatcgaat  300
gcagtaaaga ttttgaaaat tgaatttttct tcagggtaaa gaaaagcatc tctcaaaagg  360
```

```
cgagaacctg tttcgagaga ttctaatcgt ttggcagaca taggaacgta aagccagacg    420
tctccatctt ctagttcatc tatccaataa actaagaaat agaggcctag ggcattcact    480
acactaaata gtttaggccc atcgtattct tcgtagacct tatttatctc tatagtgcct    540
aagcttttct cttgaactaa agggtacatt acatcattct tctatacatt cgaatcgcgt    600
gtgtggttca gagtccgttt taaaccatac agttatatgg tggtggcctc cggtttcttt    660
catcactccg tcgtcttcaa taagcgcgcc cgttgacaat agcttttgtc gaagaggttt    720
gaacaacttc ttcttttga gcgcttcttt tttctgagtg aataacgatg agccataaag    780
catttctcta tcagttggct ttttcgcttt tcttccaggg ttttcttcaa gtgtagaact    840
aaaacaggtt tttacaggtg gattactatt caccaatcgg aaagctgttc cagatgcagc    900
gatcgcatct tttggaggca tatcatcggg atagtaatct gggtaatcac tcatacatat    960
gcacaggttc gtaaaaaaac attgttgcat attagttagg ttctatttgt taatcaacgg   1020
cctaatacgt gtttgtgtga tagaaatcgc ttcctctgat agatcattac cccaaaattt   1080
gcggtcatga ctcaaagctg aaacacctac agcgccagcc cccataaatg ggtcacaaac   1140
aagttcgcct tctgtcgagc tttgttttat tagaatatcc atcagttcaa cgggttttc     1200 tgtaggataa cctctatgaa tgcggggaac tgaa                                1234
```

<210> SEQ ID NO 80
<211> LENGTH: 1614
<212> TYPE: DNA
<213> ORGANISM: Vibrio parahaemolyticus

<400> SEQUENCE: 80

```
ttttctggag ataatgaatt gagcagagaa atatacgata tggaacgacg ctgtgttaat     60
aggcacaatg atttagcggg tcacattaat cggatgagtc agcagcaagc tcgtatcatg    120
acaaacgaaa atatagcggc gacaaagaa gtagttgctc acgtatacgg aaaagctaac    180
tcttacagca atgtaattat tgctgctggt tatgtcggtt tctttacttt atggtcaagt    240
ctaaaaagtg atttaccctca atgggctatt ttaagctcag gcgcacttat actgatatca    300
ctgatgacat ttataggatt tgaactatat aaaatgatca gtgtttcagt acaaatgcac    360
agagtctcaa aacggcttca aaagcccgac atgtcgtctc taagtgaaat acagcgtatt    420
gagcaaaaaa gcgcactgat taacgctagg gtctgggttt ttacagttat tccaacagtt    480
ttgtcgggat ttggagccgg tcttatattg ttatactgct ttctggttga ctttatagca    540
ccatatttgc aacaaaccta acaaacaatt taagagtgat tcagcacgct tggcattttc    600
ggtttgggtt gagttcggtg tttacggtgg tcaaattgat agtcgtggtt gcgtgcttca    660
caccttaatt gggcgttagg cttgtcgtac aaaatcgaat aggtattaaa attgaaaggt    720
acagaaatac aagctcaaaa tgtaaccaaa ccgattcagc ttttagctgc ttggcttgtt    780
ggtttaatcg caattaacgg ctcttttctt ggagctgcta atgttatttc aactccaact    840
tgggctgccg gattactagt tattgcctcg gtatttaatg tccctctgtt tctaggctta    900 attttttct tacaaactaa gtttcgtgca gaactacaag aagattcgtt ctatgctaag    960
cacctagata aagtaacagg ggcaatgcag actagtgata catcgataaa agcggaagtc   1020
aaagctgatg ttcaaaaaat acaaaaggaa aatgcggaaa actatgaagc aatacagaaa   1080
gaacttcggg ctgtaatgaa ttccttaaat ggtattgcat atagttctgg aaatagtgaa   1140
cttgagcaga aagtcgtaga agcccagcaa cgagtagcaa aattagagtc taacaataaa   1200
aagttctcaa ttaagcttgc cttgaataaa gtactagatc aatttaatgc tatttcgcat   1260
```

```
gaacttacag cttcaggtta tattatcgcg gacgttttg ggagcgacaa acttaactct   1320
aaagctatct cttacattga tggtgtcgat aaagttttat tgcttgacat agttaatact   1380
ttaaagcctt ttggatttga tcgaattgac tatgatcctg aagataaggg ctttgataga   1440
gatgcaaaag tttacattgg ctcctatata gatgatttcc ctgaagctag aaggtcagtt   1500
ttaatttctc atgaagttat ggatattcta aagatgata ctaagtcact gagagattta   1560
aataatttca ttcgagatca acaagcctaa caaggcgttt aagacagatt ccca         1614
```

<210> SEQ ID NO 81
<211> LENGTH: 18
<212> TYPE: DNA
<213> ORGANISM: Vibrio parahaemolyticus

<400> SEQUENCE: 81

```
agcaacgaaa acgcctgt                                                 18
```

<210> SEQ ID NO 82
<211> LENGTH: 21
<212> TYPE: DNA
<213> ORGANISM: Vibrio parahaemolyticus

<400> SEQUENCE: 82

```
accgtatcac caatggactg t                                             21
```

<210> SEQ ID NO 83
<211> LENGTH: 18
<212> TYPE: DNA
<213> ORGANISM: Vibrio parahaemolyticus

<400> SEQUENCE: 83

```
tcgttgcttt tgcggaca                                                 18
```

<210> SEQ ID NO 84
<211> LENGTH: 21
<212> TYPE: DNA
<213> ORGANISM: Vibrio parahaemolyticus

<400> SEQUENCE: 84

```
tggcatagtg gttacctgac a                                             21
```

<210> SEQ ID NO 85
<211> LENGTH: 2114
<212> TYPE: DNA
<213> ORGANISM: Vibrio parahaemolyticus

<400> SEQUENCE: 85

```
atgtctgtat cgtcaccgt cgttaaccag tatggcaatt tgaaagcaac gaaaacgcct     60
gttgcggatt gccaagaata cgtgctgatt tcggcggtgg actaccaaga atataaggaa   120
ccagtcctct tcaacggtga cttgttcctg tatgtcagtg gcgtgctctt gatcaacatg   180
gtcgttggtc actgggtggg tcgtgttgtt cgccttatga gtaaaaggta atcttatga    240 aaaaactaga acttgttgta actaacgtaa aacacgcagt cgtaaacaaa aaaccgcag    300 ctggcgctgc tcttatggtc gcgtctgtct ctccggcctt cgctgaagtc gatatacgg    360 gcgcaatcaa ctctgcggta tccggtggtc aagctaacgt atcactggtt gtggcgggtc   420
taattggtat ggctgcactg ggctttggtg tgaccatggt tgttggcttc ttacgtcgct   480
aacggttcac ctctatgcct cctttatcgg gtaatttact tggagatgtt ctcgctatcg   540
```

```
ttctaggtgt tgcctttgcg ggggcattcc tccacggctt tgtgagtggc atcaatactc    600
actaatcaac ggataaaggg ggcttcggct cccttttta ttggttttat acaatgaatc     660
actatctccg ttttttatt gtccttgtta ttctatgcgc tagtcatcat acgtatgctt     720
tagaagcacg tattagtcat atgcaaatga ggggttgtgg ctctcaaggt gattgggttg    780
accttacaa ggtgaatact tgttttttgg atactgggta tttcgactca tgcacatttg     840
agaagacatc atatgctaat gctcgcgatc cctatcaaac agtttgtgat aatgggctcg    900
gtctttctta ttctgaggtt cgttgtccag aaaatagcga atttgaccct tcaaccttac    960
gttgtaaatc ggtttgtgaa tatggcaaga accctgacgg cacctgcatg gatgcttgcc   1020
agttcaaaca gtccattggt gatacggtga aattgcattg gcaccctgcc atatacggcg   1080
aactggtgac aggcgcgtgc tacgagact acggtgccac tcgatgcgaa gtgaccaaaa    1140
acgaatccac cattatttgt actggcgttc ctgatggaca gtacacgccc gactctcaat   1200
gctctctgcg ctttgcttac actggacgtc agtgtgacgg tggcacactt ttctggggcg   1260
tgaatgggcc agacgagcca atcattccac cggatacgcc agaagaccca actcatgacc   1320
ctgatgaccc aacaggcgag attgaagacc caagtgtcct acccgacgat tcaaccaaca   1380
cggttaatcc cggtgtcgtt gatgataaac cggatgtaga agaccctgac acggatgaat   1440
cgacagacac ggcagtcctt tctgctatta agggcttaa cgtggatgtg aacaaaggca   1500
ttcatgatct taacgtcgat atcaaccagt cacacgctga catcaccaac gcggtgattg   1560
atgtgaaagg ctctttggtc gataacaccc aagccattca agaacagcaa atcaatgaca   1620
acaagattta taacaacacc aaggcactca tccaacaggc caacggcgat atcactacgg   1680
cggtgaacaa caataccaac gccaccattg gtattcgtaa cgatttaaaa gggcttggtg   1740
attcaatggg cgaactcgat agcagcttaa atgcgattga gggtctattg actggctcag   1800
agtttggtac acctacgggc accgctatca ctggcgaaat cttcacggca gaagactttg   1860
ccaacctgca aacccgata gatgaaaaag ccgaatccat ccaaggctat gtggacgata    1920
ttaaaggctt aatcactatc ggcaccaact tcaacaacgg cacattaagc gacaagtctt   1980
ttaacatcaa aggcgcaacc gttgaatcag gactacagcg ttttgatgcg gtatcgggct   2040
acgtgcgccc tgtcgtgctg ttcatttgtg ccttaatcgc cctttgggtt ctgtttggta   2100
atcggagtaa ataa                                                    2114
```

<210> SEQ ID NO 86
<211> LENGTH: 18
<212> TYPE: DNA
<213> ORGANISM: Vibrio parahaemolyticus

<400> SEQUENCE: 86

```
gcatagtggt acctgaca                                                  18
```

<210> SEQ ID NO 87
<211> LENGTH: 24
<212> TYPE: DNA
<213> ORGANISM: Vibrio parahaemolyticus

<400> SEQUENCE: 87

```
tttcttactt ctgtgagcat ttga                                           24
```

<210> SEQ ID NO 88
<211> LENGTH: 24
<212> TYPE: DNA
<213> ORGANISM: Vibrio parahaemolyticus

<400> SEQUENCE: 88
gattactgag cctctaaagc cgtc                                          24

<210> SEQ ID NO 89
<211> LENGTH: 24
<212> TYPE: DNA
<213> ORGANISM: Vibrio parahaemolyticus

<400> SEQUENCE: 89
aaagaatgaa gacactcgta aact                                          24

<210> SEQ ID NO 90
<211> LENGTH: 24
<212> TYPE: DNA
<213> ORGANISM: Vibrio parahaemolyticus

<400> SEQUENCE: 90
ctaatgactc ggagatttcg gcag                                          24

<210> SEQ ID NO 91
<211> LENGTH: 22
<212> TYPE: DNA
<213> ORGANISM: Vibrio parahaemolyticus

<400> SEQUENCE: 91
aatgactcgg agatttcggc ag                                            22

<210> SEQ ID NO 92
<211> LENGTH: 878
<212> TYPE: DNA
<213> ORGANISM: Vibrio parahaemolyticus

<400> SEQUENCE: 92
taatttaaca taatatacat aatgcgcact gatataggg ttcctgtgga cttgcaatca    60
ctaaggccaa tccagcacaa gccattgaaa tgcttgataa tccaagtccg ttaaactttt   120
ttcctatgtt ctgccatagt gtctgcgctt cgtgcgtttt tgctttatcc atcgccaagc   180
caatcagtgc ctttttctttg tcttcaccaa tagtttcagc aagcataagt atctgatttt   240
cattgagata acttcgacct tttcttactt ctgtgagcat ttgagggctt acacctaggt   300
catgagcaat ctgcttgtat tgaatgtagt tcatttgctc tttataagca tcaatgagct   360
tgtttgtgta catttctgct tttcctctaa tcacgctatt ggactgattt tagtcttta   420
gtacagattt tgctgtgttg acggtacaga aatatctgta tttaatcgct acagaattta   480
ctgtatcaga ccgccttagc tttgggcgtt tgcccttgac gctttcgcgc ttggctttgg   540
cggtcactct ctcaactagt caggtggttg taatgatcgt attagaaact gaagttcaaa   600
acgtcaatgt taaacgtta acgctccgtc acttcgcagt gtctcacgtt ccagctttca    660
aactttgtta catcactaca actgacatct ttgaagaagt cgtcgttcct ttcaatcact   720
ttggctactg cattagcaca ttcgaaaaca accaagagtc ctttggttat ctctcggttg   780
gcgattacga gtttcgcttt gaatctgacg agcatgaagt tctatgtcgt ttcttaggca   840
tgacaccttc aaaagcgacg gctttagagg ctcagtaa                           878

<210> SEQ ID NO 93
<211> LENGTH: 878
<212> TYPE: DNA
<213> ORGANISM: Vibrio parahaemolyticus -continued

<400> SEQUENCE: 93

| | | | | | |
|---|---|---|---|---|---|
| taatttaaca | taatatacat | aatgcgcact | gatatagtgg | ttcctgtgga | cttgcaatca | 60 |
| ctaaggccaa | tccagcacaa | gccattgaaa | tgcttgataa | tccaagtccg | ttaaacttttt | 120 |
| ttcctatgtt | ctgccacagt | gtctgcgctt | cgtgcgtttt | tgctttatcc | atagccaagc | 180 |
| caatcagtgc | cttttctttg | tcttcaccaa | tagtttcagc | aagcataagt | atctgatttt | 240 |
| cattgagata | acttcgacct | tttcttactt | ctgtgagcat | ttgagggctt | acacctaggt | 300 |
| catgagcaat | ctgcttgtat | tgaatgtagt | tcatttgctc | tttataagca | tcaatgagct | 360 |
| tgtttgtgta | catttctgct | tttcctctaa | tcacgctatt | ggactgattt | tagtctttta | 420 |
| gtacagattt | tgctgtgttg | acggtacaga | aatatctgta | tttaatcact | acagaattta | 480 |
| ctgtatcaga | ccgccttagc | tttgggcgtt | tgcccttgac | gctttcgcgc | ttggctttgg | 540 |
| cggtcactct | ctcaactagt | caggtggttg | taatgatcgt | attagaaact | gaagttcaaa | 600 |
| acgtcaatgt | taaaacgtta | acgctccgtc | acttcgcagt | gtctcacgtt | ccagctttca | 660 |
| aactttgtta | catcactaca | actgacatct | ttgaagaagt | cgtcgttcct | ttcaatcact | 720 |
| ttggctactg | cattagcaca | ttcgaaaaca | accaagagtc | ctttagttac | ctctcggttg | 780 |
| gcgattacga | gtttcgcttt | gaatctgacg | agcatgaagt | tctatgtcgt | ttcttaggca | 840 |
| tgacaccttc | aaaagcgacg | gctttagagg | ctcagtaa | | | 878 |

<210> SEQ ID NO 94
<211> LENGTH: 24
<212> TYPE: DNA
<213> ORGANISM: Vibrio parahaemolyticus

<400> SEQUENCE: 94
aagtgctaca tgaatgaaag tgct                                          24

<210> SEQ ID NO 95
<211> LENGTH: 25
<212> TYPE: DNA
<213> ORGANISM: Vibrio parahaemolyticus

<400> SEQUENCE: 95
tcaatgaagt atcacgaaat gacta                                         25

<210> SEQ ID NO 96
<211> LENGTH: 24
<212> TYPE: DNA
<213> ORGANISM: Vibrio parahaemolyticus

<400> SEQUENCE: 96
ttcacgatgt acttactttc acga                                          24

<210> SEQ ID NO 97
<211> LENGTH: 25
<212> TYPE: DNA
<213> ORGANISM: Vibrio parahaemolyticus

<400> SEQUENCE: 97
agttacttca tagtgcttta ctgat                                         25

<210> SEQ ID NO 98
<211> LENGTH: 1810
<212> TYPE: DNA
<213> ORGANISM: Vibrio parahaemolyticus

<400> SEQUENCE: 98

```
cgctaggttt tatatgtcaa ggatatgaaa tggctaagtt tttaaataca agtgctacaa      60
actactatct cgaagagctt attaagaatg cttccgaaag actgattcta attagccctt     120
ttctcaagct taatgatcgc attcgagagc ttttggaaga caaggaccga ttaaaaatcg     180
atattagaat tgtctatggc aaaagcgaac tacaaccgga tgagattaac tggcttaaaa     240
gcctctcctt tgtgcgtact agttttgta aaaacctcca tgcaaagtgc tacatgaatg     300
aaagtgcttg tatcattaca agcttaaatc tctatgagtt cagccaagta acaataatg     360 aaatgggtat cttcattgac cgtgacgaag accccaatgt ctacaaagat tcctacgagg     420
aagctcaacg cattattcgt attgtctatg caaaagcga actacaaccg aaagttcgag     480
ctgctaattt agatacggaa cttactgaaa agcctgttac agataatgaa ctaattaaac     540
tcagctcctc taagttagcc aaaaagcaca aacttaaaac agatgagttt ctcagcttgt     600
gtgttaataa aggatactta acgttagatg acggaaagca ctcattaacc gatgaaggta     660
aatcttcagg tggtgagttt aaatacagca acgtttcgg tccatattt gtctggccag     720 agtccttgga agtatcgtaa ctattgggtt caatatttta aagtgagtac agcaaacatg     780
aagattaaaa taagagctat gttaagttta gctgccgccc ttagtttgat aggttgcacc     840
tccactaact tcagtgaata taagggtcta cctggccata agtccatagc tgttggctct     900
aatggcgtta tcgcatattc ctcatcgaag cccaatgccg aaacagccat acaacagcc     960 attgataaat gctcttcaat cggtggcaaa gattgtaagt ttatcgatgt tgatggttat    1020
agtcctatcg gtaataaaac atatatgtat gatgatcgcg cagctagtgt tgattaccta    1080
gaaaaaggtt catacgcagt aaggtataaa tgtgagcaat taacgaaagc aatggcacaa    1140
tcattatttc gttcaggcca tacttaccta gatggagact cagatgggaa gccttgtgag    1200
tcaaaccttt ggagctcata ttattcgaca gataccagta gcagaaaagc aaaaggtact    1260
aactgtcatt atgttcgtgg gtatcgaaga aaaaatggta cttatgtcag tggttataca    1320
cgctgtcgtt gatttacaag gctccattcg gagccttttt tcatataatt ttctttaata    1380
ctcttgcata cttgagaatc tgatgcgcaa tagcaatgtc atttgacgca cctaactcaa    1440
gtaaagcaac cccaattaat acttgctgcg cagtaaccaa ctgtcctgtt ggaagttcta    1500
accgatcatg cctcattacg aagttttccc aatcttcaca gctgctaagt ccctaccct    1560 tattcattcg cattaggcgc ttacactccg gaggaatgga tttccccttg tcccattcct    1620
tgatcgtcct cacagttttt aaacaaagtt tggcagcttc ttcgacggtt aaaccacatt    1680
caaattcacg aaaaatatag ttttagtca tttcgtgata cttcattgaa ttgtccctca    1740
aaagagagac attttatagg atacgcatat gcaatcgcat tcaacataag cgcccataat    1800
gcgcaccagg                                                          1810

<210> SEQ ID NO 99
<211> LENGTH: 1174
<212> TYPE: DNA
<213> ORGANISM: Vibrio parahaemolyticus

<400> SEQUENCE: 99
atggctaagt ttttaaacac aagtgcaaca aactactacc tcgaagaact aattaagaac      60
gcttctgaaa ggctgatcct catcagccct tttctcaagc ttaatgatcg cattcgagag     120
cttttggaag acaagaccg attaaagata gacattcgaa ttgtctatgg caaaagcgag     180
ctacaacctg atgagattaa ctggcttaaa agcctctcct ttgtgcgtac cagttttgc     240
```

| | | | |
|---|---|---|---|
| aaaaacctcc | atgcaaagtg ctacatgaat gaaagtgctt gtatcattac | aagtttaaac | 300 |
| ctctacgagt | ttagccaagt aaacaataac gaaatgggta tcttcattga | ccgtgacgaa | 360 |
| gaccccaatg | tctacaaaga ttcctacgag gaagcgcaac gcattattcg | tattagtgat | 420 |
| gaagttagaa | tctcgttaga gaaagttgaa gctgctaaat tagatacgga | atctactcaa | 480 |
| aagcctgtta | cagagaatga actaattaaa cttagttcct ctaagttagc | taaaaagcat | 540 |
| aaacttaaaa | cagatgactt ccttcagatg tgtgtaagca agggctactt | atctttcgaa | 600 |
| gatggaaaac | attctttaac cgaagaaggg aaatcgttgg gtggtgagtt | caagtacagt | 660 |
| aaacgttttg | gtccttactt tatctggcca gagtcattag aggttgaata | gaaaataag | 720 |
| gctcctgttg | gagccttcaa tcacactatt ttctttagta ttcttgcata | cttcaatatt | 780 |
| tggtgagcca | cctttatatc attcgatgca cctaactcaa gtaaagcaac | cccaatcaat | 840 |
| acttgctgcg | cagtaaccaa ctgtcctgtt ggaagctcta atcgatcatg | cctcattacg | 900 |
| aagttttccc | aatcttcaca agagctcaat tccctacccg tattcatcct | catcaagcgc | 960 |
| ttacactctg | gaggaatgga ttttcccttg tcccattctt tgaccgttct | cacagttttt | 1020 |
| aaacaaagtt | tggcagcttc ttcgacggtt aaaccacatt caaattcacg | aaaaatatag | 1080 |
| tttttagtca | tttcgtgata cttcattgaa ttgtccctca aaagagagac | attttatagg | 1140 |
| atacgcatat | gcaatcgcat tcaacataag cgcc | | 1174 |

<210> SEQ ID NO 100
<211> LENGTH: 25
<212> TYPE: DNA
<213> ORGANISM: Vibrio parahaemolyticus

<400> SEQUENCE: 100
gaatgctgcc aacatggata taaat         25

<210> SEQ ID NO 101
<211> LENGTH: 24
<212> TYPE: DNA
<213> ORGANISM: Vibrio parahaemolyticus

<400> SEQUENCE: 101
gacaaaggta tgctgccaaa agtg          24

<210> SEQ ID NO 102
<211> LENGTH: 25
<212> TYPE: DNA
<213> ORGANISM: Vibrio parahaemolyticus

<400> SEQUENCE: 102
cttacgacgg ttgtacctat attta         25

<210> SEQ ID NO 103
<211> LENGTH: 24
<212> TYPE: DNA
<213> ORGANISM: Vibrio parahaemolyticus

<400> SEQUENCE: 103
ctgtttccat acgacggttt tcac          24

<210> SEQ ID NO 104
<211> LENGTH: 25
<212> TYPE: DNA
<213> ORGANISM: Vibrio parahaemolyticus

<400> SEQUENCE: 104

```
actcaacaca agaagagatc gacaa                                        25

<210> SEQ ID NO 105
<211> LENGTH: 20
<212> TYPE: DNA
<213> ORGANISM: Vibrio parahaemolyticus

<400> SEQUENCE: 105
gatgagcggt tgatgtccaa                                              20

<210> SEQ ID NO 106
<211> LENGTH: 21
<212> TYPE: DNA
<213> ORGANISM: Vibrio parahaemolyticus

<400> SEQUENCE: 106
cgctcgcgtt cacgaaaccg t                                            21

<210> SEQ ID NO 107
<211> LENGTH: 25
<212> TYPE: DNA
<213> ORGANISM: Vibrio parahaemolyticus

<400> SEQUENCE: 107
tgagttgtgt tcttctctag ctgtt                                        25

<210> SEQ ID NO 108
<211> LENGTH: 20
<212> TYPE: DNA
<213> ORGANISM: Vibrio parahaemolyticus

<400> SEQUENCE: 108
ctactcgcca actacaggtt                                              20

<210> SEQ ID NO 109
<211> LENGTH: 21
<212> TYPE: DNA
<213> ORGANISM: Vibrio parahaemolyticus

<400> SEQUENCE: 109
gcgagcgcaa gtgctttggc a                                            21

<210> SEQ ID NO 110
<211> LENGTH: 17
<212> TYPE: DNA
<213> ORGANISM: Vibrio parahaemolyticus

<400> SEQUENCE: 110
tccctttccc tgcccccc                                                17

<210> SEQ ID NO 111
<211> LENGTH: 24
<212> TYPE: DNA
<213> ORGANISM: Vibrio parahaemolyticus

<400> SEQUENCE: 111
cgctgccatt gtatagtctt tatc                                         24

<210> SEQ ID NO 112
<211> LENGTH: 20
<212> TYPE: DNA
<213> ORGANISM: Vibrio parahaemolyticus
```

<400> SEQUENCE: 112
tgacatccta catgactgtg                                              20

<210> SEQ ID NO 113
<211> LENGTH: 17
<212> TYPE: DNA
<213> ORGANISM: Vibrio parahaemolyticus

<400> SEQUENCE: 113
agggaaaagg acggggg                                                 17

<210> SEQ ID NO 114
<211> LENGTH: 24
<212> TYPE: DNA
<213> ORGANISM: Vibrio parahaemolyticus

<400> SEQUENCE: 114
gcgacggtaa catatcagaa atag                                         24

<210> SEQ ID NO 115
<211> LENGTH: 20
<212> TYPE: DNA
<213> ORGANISM: Vibrio parahaemolyticus

<400> SEQUENCE: 115
actgtaggat gtactgacac                                              20

<210> SEQ ID NO 116
<211> LENGTH: 23
<212> TYPE: DNA
<213> ORGANISM: Vibrio parahaemolyticus

<400> SEQUENCE: 116
ttgctttcag tttgctattg gct                                          23

<210> SEQ ID NO 117
<211> LENGTH: 23
<212> TYPE: DNA
<213> ORGANISM: Vibrio parahaemolyticus

<400> SEQUENCE: 117
tgtttaccgt catataggcg ctt                                          23

<210> SEQ ID NO 118
<211> LENGTH: 23
<212> TYPE: DNA
<213> ORGANISM: Vibrio parahaemolyticus

<400> SEQUENCE: 118
agaaatacaa caatcaaaac tga                                          23

<210> SEQ ID NO 119
<211> LENGTH: 23
<212> TYPE: DNA
<213> ORGANISM: Vibrio parahaemolyticus

<400> SEQUENCE: 119
aacgaaagtc aaacgataac cga                                          23

<210> SEQ ID NO 120
<211> LENGTH: 23
<212> TYPE: DNA
<213> ORGANISM: Vibrio parahaemolyticus

```
<400> SEQUENCE: 120
acaaatggca gtatatccgc gaa                                              23

<210> SEQ ID NO 121
<211> LENGTH: 23
<212> TYPE: DNA
<213> ORGANISM: Vibrio parahaemolyticus

<400> SEQUENCE: 121
tctttatgtt gttagttttg act                                              23

<210> SEQ ID NO 122
<211> LENGTH: 25
<212> TYPE: DNA
<213> ORGANISM: Vibrio parahaemolyticus

<400> SEQUENCE: 122
tgacgcagct ttagggacta actta                                            25

<210> SEQ ID NO 123
<211> LENGTH: 27
<212> TYPE: DNA
<213> ORGANISM: Vibrio parahaemolyticus

<400> SEQUENCE: 123
cgctaaacca ctaacatctt catctac                                          27

<210> SEQ ID NO 124
<211> LENGTH: 24
<212> TYPE: DNA
<213> ORGANISM: Vibrio parahaemolyticus

<400> SEQUENCE: 124
gcgaggaggg ttattctgac ttag                                             24

<210> SEQ ID NO 125
<211> LENGTH: 24
<212> TYPE: DNA
<213> ORGANISM: Vibrio parahaemolyticus

<400> SEQUENCE: 125
ctaagtcaga ataccctcc tcgc                                              24

<210> SEQ ID NO 126
<211> LENGTH: 28
<212> TYPE: DNA
<213> ORGANISM: Vibrio parahaemolyticus

<400> SEQUENCE: 126
aaatctatga atttgtagaa gtggtgtg                                         28

<210> SEQ ID NO 127
<211> LENGTH: 29
<212> TYPE: DNA
<213> ORGANISM: Vibrio parahaemolyticus

<400> SEQUENCE: 127
atacctgtca gtcgtcgaaa ttggtggag                                        29

<210> SEQ ID NO 128
<211> LENGTH: 28
<212> TYPE: DNA
```

<213> ORGANISM: Vibrio parahaemolyticus

<400> SEQUENCE: 128
atacctgtca gtcgtcgaaa ttggtgga                    28

<210> SEQ ID NO 129
<211> LENGTH: 28
<212> TYPE: DNA
<213> ORGANISM: Vibrio parahaemolyticus

<400> SEQUENCE: 129
atacctgtca gtcgtcgaaa ttggtgga                    28

<210> SEQ ID NO 130
<211> LENGTH: 26
<212> TYPE: DNA
<213> ORGANISM: Vibrio parahaemolyticus

<400> SEQUENCE: 130
caacatcatg ccgctgtaat ggtgag                      26

<210> SEQ ID NO 131
<211> LENGTH: 25
<212> TYPE: DNA
<213> ORGANISM: Vibrio parahaemolyticus

<400> SEQUENCE: 131
actgcgtcga aatccctgat tgaat                       25

<210> SEQ ID NO 132
<211> LENGTH: 27
<212> TYPE: DNA
<213> ORGANISM: Vibrio parahaemolyticus

<400> SEQUENCE: 132
gcgatttggt gattgtagaa gtagatg                     27

<210> SEQ ID NO 133
<211> LENGTH: 24
<212> TYPE: DNA
<213> ORGANISM: Vibrio parahaemolyticus

<400> SEQUENCE: 133
cgctcctccc aataagactg aatc                        24

<210> SEQ ID NO 134
<211> LENGTH: 24
<212> TYPE: DNA
<213> ORGANISM: Vibrio parahaemolyticus

<400> SEQUENCE: 134
gattcagtct tattgggagg agcg                        24

<210> SEQ ID NO 135
<211> LENGTH: 28
<212> TYPE: DNA
<213> ORGANISM: Vibrio parahaemolyticus

<400> SEQUENCE: 135
tttagatact taaacatctt caccacac                    28

<210> SEQ ID NO 136
<211> LENGTH: 29

```
<212> TYPE: DNA
<213> ORGANISM: Vibrio parahaemolyticus

<400> SEQUENCE: 136
tatggacagt cagcagcttt aaccacctc                                29

<210> SEQ ID NO 137
<211> LENGTH: 28
<212> TYPE: DNA
<213> ORGANISM: Vibrio parahaemolyticus

<400> SEQUENCE: 137
tatggacagt cagcagcttt aaccacct                                 28

<210> SEQ ID NO 138
<211> LENGTH: 28
<212> TYPE: DNA
<213> ORGANISM: Vibrio parahaemolyticus

<400> SEQUENCE: 138
tatggacagt cagcagcttt aaccacct                                 28

<210> SEQ ID NO 139
<211> LENGTH: 26
<212> TYPE: DNA
<213> ORGANISM: Vibrio parahaemolyticus

<400> SEQUENCE: 139
gttgtagtac ggcgacatta ccactc                                   26

<210> SEQ ID NO 140
<211> LENGTH: 25
<212> TYPE: DNA
<213> ORGANISM: Vibrio parahaemolyticus

<400> SEQUENCE: 140
aatctgttct ggttgtgttt agagc                                    25

<210> SEQ ID NO 141
<211> LENGTH: 25
<212> TYPE: DNA
<213> ORGANISM: Vibrio parahaemolyticus

<400> SEQUENCE: 141
aaaggtccca aagctgtcaa tatag                                    25

<210> SEQ ID NO 142
<211> LENGTH: 24
<212> TYPE: DNA
<213> ORGANISM: Vibrio parahaemolyticus

<400> SEQUENCE: 142
aagtcttttc atcaccttca ttgc                                     24

<210> SEQ ID NO 143
<211> LENGTH: 33
<212> TYPE: DNA
<213> ORGANISM: Vibrio parahaemolyticus

<400> SEQUENCE: 143
ctaggggttg aacagtttgg atcttttagt tta                           33

<210> SEQ ID NO 144
```

```
<211> LENGTH: 21
<212> TYPE: DNA
<213> ORGANISM: Vibrio parahaemolyticus

<400> SEQUENCE: 144
ctaggggttg aacagtttgg a                                               21

<210> SEQ ID NO 145
<211> LENGTH: 24
<212> TYPE: DNA
<213> ORGANISM: Vibrio parahaemolyticus

<400> SEQUENCE: 145
tgtagtacgg cgacattacc actc                                            24

<210> SEQ ID NO 146
<211> LENGTH: 25
<212> TYPE: DNA
<213> ORGANISM: Vibrio parahaemolyticus

<400> SEQUENCE: 146
ttagacaaga ccaacacaaa tctcg                                           25

<210> SEQ ID NO 147
<211> LENGTH: 25
<212> TYPE: DNA
<213> ORGANISM: Vibrio parahaemolyticus

<400> SEQUENCE: 147
tttccagggt ttcgacagtt atatc                                           25

<210> SEQ ID NO 148
<211> LENGTH: 24
<212> TYPE: DNA
<213> ORGANISM: Vibrio parahaemolyticus

<400> SEQUENCE: 148
ttcagaaaag tagtggaagt aacg                                            24

<210> SEQ ID NO 149
<211> LENGTH: 33
<212> TYPE: DNA
<213> ORGANISM: Vibrio parahaemolyticus

<400> SEQUENCE: 149
gatccccaac ttgtcaaacc tagaaaatca aat                                  33

<210> SEQ ID NO 150
<211> LENGTH: 21
<212> TYPE: DNA
<213> ORGANISM: Vibrio parahaemolyticus

<400> SEQUENCE: 150
gatccccaac ttgtcaaacc t                                               21

<210> SEQ ID NO 151
<211> LENGTH: 23
<212> TYPE: DNA
<213> ORGANISM: Vibrio parahaemolyticus

<400> SEQUENCE: 151
gctgagaggt tggaaagtgt agc                                             23
```

```
<210> SEQ ID NO 152
<211> LENGTH: 24
<212> TYPE: DNA
<213> ORGANISM: Vibrio parahaemolyticus

<400> SEQUENCE: 152
tcttcgttac catagtatga gcca                                          24

<210> SEQ ID NO 153
<211> LENGTH: 21
<212> TYPE: DNA
<213> ORGANISM: Vibrio parahaemolyticus

<400> SEQUENCE: 153
tatcggtggg atttctggtg t                                             21

<210> SEQ ID NO 154
<211> LENGTH: 25
<212> TYPE: DNA
<213> ORGANISM: Vibrio parahaemolyticus

<400> SEQUENCE: 154
cattaaccaa ggagtaggag gaagt                                         25

<210> SEQ ID NO 155
<211> LENGTH: 29
<212> TYPE: DNA
<213> ORGANISM: Vibrio parahaemolyticus

<400> SEQUENCE: 155
gggtgatcat ggagcatagt gaaggtaaa                                     29

<210> SEQ ID NO 156
<211> LENGTH: 25
<212> TYPE: DNA
<213> ORGANISM: Vibrio parahaemolyticus

<400> SEQUENCE: 156
tctcaagcag ggtatcaatc aggcg                                         25

<210> SEQ ID NO 157
<211> LENGTH: 23
<212> TYPE: DNA
<213> ORGANISM: Vibrio parahaemolyticus

<400> SEQUENCE: 157
cgactctcca acctttcaca tcg                                           23

<210> SEQ ID NO 158
<211> LENGTH: 24
<212> TYPE: DNA
<213> ORGANISM: Vibrio parahaemolyticus

<400> SEQUENCE: 158
agaagcaatg gtatcatact cggt                                          24

<210> SEQ ID NO 159
<211> LENGTH: 21
<212> TYPE: DNA
<213> ORGANISM: Vibrio parahaemolyticus

<400> SEQUENCE: 159
atagccaccc taaagaccac a                                             21
```

<210> SEQ ID NO 160
<211> LENGTH: 25
<212> TYPE: DNA
<213> ORGANISM: Vibrio parahaemolyticus

<400> SEQUENCE: 160
gtaattggtt cctcatcctc cttca                                           25

<210> SEQ ID NO 161
<211> LENGTH: 29
<212> TYPE: DNA
<213> ORGANISM: Vibrio parahaemolyticus

<400> SEQUENCE: 161
cccactagta cctcgtatca cttccattt                                       29

<210> SEQ ID NO 162
<211> LENGTH: 25
<212> TYPE: DNA
<213> ORGANISM: Vibrio parahaemolyticus

<400> SEQUENCE: 162
agagttcgtc ccatagttag tccgc                                           25

<210> SEQ ID NO 163
<211> LENGTH: 25
<212> TYPE: DNA
<213> ORGANISM: Vibrio parahaemolyticus

<400> SEQUENCE: 163
agagttcgtc ccatagttag tccgc                                           25

<210> SEQ ID NO 164
<211> LENGTH: 19
<212> TYPE: DNA
<213> ORGANISM: Vibrio parahaemolyticus

<400> SEQUENCE: 164
gacatcgata tgggtgccg                                                  19

<210> SEQ ID NO 165
<211> LENGTH: 19
<212> TYPE: DNA
<213> ORGANISM: Vibrio parahaemolyticus

<400> SEQUENCE: 165
cgagacgatg cagccattc                                                  19

<210> SEQ ID NO 166
<211> LENGTH: 26
<212> TYPE: DNA
<213> ORGANISM: Vibrio parahaemolyticus

<400> SEQUENCE: 166
tctcatgcgt ctccctggtg aatgtg                                          26

<210> SEQ ID NO 167
<211> LENGTH: 19
<212> TYPE: DNA
<213> ORGANISM: Vibrio parahaemolyticus

<400> SEQUENCE: 167
ctgtagctat acccacggc                                                  19

<210> SEQ ID NO 168
<211> LENGTH: 19
<212> TYPE: DNA
<213> ORGANISM: Vibrio parahaemolyticus

<400> SEQUENCE: 168
gctctgctac gtcggtaag					19

<210> SEQ ID NO 169
<211> LENGTH: 26
<212> TYPE: DNA
<213> ORGANISM: Vibrio parahaemolyticus

<400> SEQUENCE: 169
agagtacgca gagggaccac ttacac				26

<210> SEQ ID NO 170
<211> LENGTH: 20
<212> TYPE: DNA
<213> ORGANISM: Vibrio parahaemolyticus

<400> SEQUENCE: 170
tgatagtcgt ggttgcgtgc					20

<210> SEQ ID NO 171
<211> LENGTH: 21
<212> TYPE: DNA
<213> ORGANISM: Vibrio parahaemolyticus

<400> SEQUENCE: 171
agctgaatcg gtttggttac a					21

<210> SEQ ID NO 172
<211> LENGTH: 23
<212> TYPE: DNA
<213> ORGANISM: Vibrio parahaemolyticus

<400> SEQUENCE: 172
ttgggcgtta ggctttgcgt aca				23

<210> SEQ ID NO 173
<211> LENGTH: 23
<212> TYPE: DNA
<213> ORGANISM: Vibrio parahaemolyticus

<400> SEQUENCE: 173
aacccgcaat ccgaaacgca tgt				23

<210> SEQ ID NO 174
<211> LENGTH: 20
<212> TYPE: DNA
<213> ORGANISM: Vibrio parahaemolyticus

<400> SEQUENCE: 174
actatcagca ccaacgcacg					20

```
<210> SEQ ID NO 175
<211> LENGTH: 21
<212> TYPE: DNA
<213> ORGANISM: Vibrio parahaemolyticus

<400> SEQUENCE: 175
tcgacttagc caaaccaatg t                                      21
```

METHODS AND COMPOSITIONS FOR IDENTIFYING PATHOGENIC VIBRIO PARAHAEMOLYTICUS

RELATED APPLICATIONS

This application is a National Stage filing under U.S.C. § 371 of PCT International Application PCT/US2016/021089, filed Mar. 5, 2016, which designates the U.S., and claims benefit under 35 U.S.C. § 119(e) of U.S. Provisional Application No. 62/128,764, filed Mar. 5, 2015, the content of each of which is incorporated by reference herein in its entirety.

FIELD OF THE INVENTION

The invention relates, in part, to methods and compositions for identifying pathogenic *Vibrio parahaemolyticus* contamination and infections.

BACKGROUND

Rare pathogenic variants of *Vibrio parahaemolyticus*, a ubiquitous yet typically harmless estuarine bacterium, can cause human gastric infections most often from the consumption of raw or improperly handled seafood, and wound infections from recreational aquatic activities [Daniels N A, et al. (2000) J Infect Dis 181: 1661-1666; Scallan E, et al. (2011) Emerg Infect Dis 2011 January DOI:10.3201/eid1701.P11101]. A better understanding of conditions that promote emergence and relative abundance of pathogens is necessary to develop appropriate strategies for disease prevention but an obstacle for the study of emergent pathogenic strains of *V. parahaemolyticus* is a lack of understanding of factors that define virulence and that could be used to detect pathogens within mostly non-pathogenic populations

SUMMARY OF THE INVENTION

According to one aspect of the invention, methods for identifying the status of a pathogenic *V. parahaemolyticus* in a sample are provided. The methods include: (a) detecting in a sample, a level of at least one ST36prp polynucleotide comprising a nucleic acid sequence set forth as SEQ ID NO:1, 2, 3, 4, 5, 6, 7, 21, 22, 23, 24, 25 or 26, or a variant thereof; (b) comparing the level of the detected ST36prp polynucleotide to a control level of the detected ST36prp polynucleotide; and (c) identifying the status of the pathogenic *V. parahaemolyticus* in the sample, based at least in part on a difference between the level of the detected ST36prp polynucleotide and the control level of the detected ST36prp polynucleotide. In some embodiments, a higher level of the detected ST36prp polynucleotide compared to the control level of the detected ST36prp polynucleotide identifies the status of the pathogenic *V. parahaemolyticus* as present in the sample. In certain embodiments, the control level of the detected ST36prp polynucleotide is zero. In some embodiments, the method also includes: (d) detecting in the sample a level of at least one of a ST36cps polynucleotide comprising a nucleic acid sequence set forth as SEQ ID NO:8, 9, 10, 27 or 28, or a variant thereof; (e) comparing the level of the detected ST36cps polynucleotide to a control level of the detected ST36cps polynucleotide; and (f) identifying the status of the pathogenic *V. parahaemolyticus* in the sample, based at least in part on the difference between the level of the detected ST36cps polynucleotide and the control level of the detected ST36cps polynucleotide. In some embodiments, a higher level of the detected ST36cps polynucleotide compared to the control level of the detected ST36cps polynucleotide identifies the status of the pathogenic *V. parahaemolyticus* as present in the sample. In some embodiments, the control level of the detected ST36cps polynucleotide is zero. In certain embodiments, the method also includes (g) detecting in the sample a level of at least one of a tlh polynucleotide comprising a nucleic acid sequence set forth as SEQ ID NO:11, 12, 13, 14, 29, 30 or 31, or a variant thereof; and (h) comparing the level of the detected tlh polynucleotide to a control level of the detected tlh polynucleotide. In some embodiments, a higher level of the detected tlh polynucleotide compared to the control level of the detected tlh polynucleotide aids in identifying the status of the pathogenic *V. parahaemolyticus* in the sample. In certain embodiments, the control level of the detected tlh polynucleotide is zero. In some embodiments, the method also includes (i) detecting in the sample a level of at least one of a tdh and trh polynucleotide comprising a nucleic acid sequence set forth as SEQ ID NO:15, 16, 17, 18, 19, 20, 32, 33, 34 or 35, or a variant thereof; and (j) comparing the level of the detected polynucleotide to a control level of the detected polynucleotide. In some embodiments, a higher level of the detected tdh or trh polynucleotide compared to the control level of the detected polynucleotide aids in identifying the status of the pathogenic *V. parahaemolyticus* in the sample. In some embodiments, the control level of the detected tdh or trh polynucleotide is zero. In certain embodiments, the method also includes: (k) detecting in the sample a level of at least one of a ST36flp polynucleotide comprising a nucleic acid sequence set forth as SEQ ID NO:36, 37, 38, 39 or 40, or a variant thereof; (1) comparing the level of the detected ST36flp polynucleotide to a control level of the detected ST36flp polynucleotide; and (m) identifying the status of the pathogenic *V. parahaemolyticus* in the sample, based at least in part on difference between the level of the detected ST36flp polynucleotide and the control level of the detected ST36flp polynucleotide. In some embodiments, a higher level of the detected ST36flp polynucleotide compared to the control level of the detected ST36flp polynucleotide aids in identifying the status of the pathogenic *V. parahaemolyticus* in the sample. In some embodiments, the control level of the detected ST36flp polynucleotide is zero. In certain embodiments, the variant of the SEQ ID NO:1, 2, 3, 4, 5, 6, 7, 21, 22, 23, 24, 25 or 26 nucleic acid sequence has at least 85%, 90%, 95%, 97%, 98%, 99%, or 100% sequence identity to the nucleic acid sequence of SEQ ID NO:1, 2, 3, 4, 5, 6, 7, 21, 22, 23, 24, 25 or 26, respectively. In some embodiments, the variant of the SEQ ID NO:8, 9, 10, 27 or 28 nucleic acid sequence has at least 85%, 90%, 95%, 97%, 98%, 99%, or 100% sequence identity to the nucleic acid sequence of SEQ ID NO:8, 9, 10, 27 or 28, respectively. In some embodiments, the variant of the SEQ ID NO:11, 12, 13, 14, 29, 30 or 31 nucleic acid sequence has at least 85%, 90%, 95%, 97%, 98%, 99%, or 100% sequence identity to the nucleic acid sequence of SEQ ID NO:11, 12, 13, 14, 29, 30 or 31, respectively. In some embodiments, the variant of the SEQ ID NO:15, 16, 17, 18, 19, 20, 32, 33, 34 or 35 nucleic acid sequence has at least 85%, 90%, 95%, 97%, 98%, 99%, or 100% sequence identity to the nucleic acid sequence of SEQ ID NO:15, 16, 17, 18, 19, 20, 32, 33, 34 or 35, respectively. In certain embodiments, the variant of the SEQ ID NO:36, 37, 38, 39 or 40 nucleic acid sequence has at least 85%, 90%, 95%, 97%, 98%, 99%, or 100% sequence identity to the nucleic acid sequence of SEQ ID NO:36, 37, 38, 39 or 40, respectively. In some embodiments, the variant of the nucleic acid sequence comprises a fragment of the nucleic acid sequence. In some embodiments, the variant of the nucleic acid sequence comprises a fragment of the nucleic acid sequence and the fragment has at least 85%, 90%, 95%, 97%, 98%, 99%, or 100% sequence identity to the region of the nucleic acid sequence with which it aligns. In certain embodiments, the sample is obtained from a subject. In some embodiments, the sample is obtained from a substrate.

According to another aspect of the invention methods of identifying the status of a pathogenic *V. parahaemolyticus* in a sample are provided. The methods include: (a) detecting in a sample a level of at least one ST36cps polynucleotide comprising a nucleic acid sequence set forth as SEQ ID NO:8, 9, 10, 27 or 28, or a variant thereof; (b) comparing the level of the detected ST36cps polynucleotide to a control level of the detected ST36cps polynucleotide; and (c) identifying the status of a pathogenic *V. parahaemolyticus* in the sample, based at least in part on a difference in the level of the detected ST36cps polynucleotide and the control level of the detected ST36cps polynucleotide. In some embodiments, a higher level of the detected ST36cps polynucleotide compared to the control level of the detected ST36cps polynucleotide identifies the status of the pathogenic *V. parahaemolyticus* as present in the sample. In certain embodiments, the control level of the detected ST36cps polynucleotide is zero. In some embodiments, the method also includes detecting in the sample a level of at least one of a polynucleotide comprising a ST36prp nucleic acid sequence or variant thereof, a tlh nucleic acid sequence or variant thereof, a tdh nucleic acid sequence or variant thereof, a trh nucleic acid sequence or variant thereof, and an ST36flp nucleic acid sequence or variant thereof. In some embodiments, the variant of the SEQ ID NO: 8, 9, 10, 27, or 28 nucleic acid sequence has at least 85%, 90%, 95%, 97%, 98%, 99%, or 100% sequence identity to the nucleic acid sequence of SEQ ID NO:8, 9, 10, 27 or 28, respectively. In certain embodiments, the variant of the nucleic acid sequence comprises a fragment of the nucleic acid sequence. In some embodiments, the variant of the nucleic acid sequence comprises a fragment of the nucleic acid sequence and the fragment has at least 85%, 90%, 95%, 97%, 98%, 99%, or 100% sequence identity to the region of the nucleic acid sequence with which it aligns. In some embodiments, the sample is obtained from a subject. In some embodiments, the sample is obtained from a substrate.

According to yet another aspect of the invention, methods of identifying the presence of a pathogenic *V. parahaemolyticus* in a sample are provided. The methods include (a) detecting in a sample a level of at least one ST36flp polynucleotide comprising a nucleic acid sequence set forth as SEQ ID NO: 36, 37, 38, 39 or 40, or a variant thereof; (b) comparing the level of the detected ST36flp polynucleotide to a control level of the detected ST36flp polynucleotide; and (c) identifying the status of a pathogenic *V. parahaemolyticus* in the sample, based at least in part on the difference between the level of the detected ST36flp polynucleotide and the control level of the detected ST36flp polynucleotide. In certain embodiments, a higher level of the detected ST36flp polynucleotide compared to the control level of the detected ST36flp polynucleotide identifies the status of the pathogenic *V. parahaemolyticus* as present in the sample. In some embodiments, the control level of the detected ST36flp polynucleotide is zero. In some embodiments, the method also includes detecting in the sample a level of at least one of a polynucleotide comprising a ST36prp nucleic acid sequence or variant thereof, a tlh nucleic acid sequence or variant thereof, a tdh nucleic acid sequence or variant thereof, a trh nucleic acid sequence or variant thereof, and an ST36cps nucleic acid sequence or variant thereof. In certain embodiments, the variant of the SEQ ID NO:36, 37, 38, 39 or 40 nucleic acid sequence has at least 85%, 90%, 95%, 97%, 98%, 99%, or 100% sequence identity to the nucleic acid sequence of SEQ ID NO:36, 37, 38, 39 or 40, respectively. In some embodiments, the variant of the nucleic acid sequence comprises a fragment of the nucleic acid sequence. In some embodiments, the variant of the nucleic acid sequence comprises a fragment of the nucleic acid sequence and the fragment has at least 85%, 90%, 95%, 97%, 98%, 99%, or 100% sequence identity to the region of the nucleic acid sequence with which it aligns. In some embodiments, the sample is obtained from a subject. In certain embodiments, the sample is obtained from a substrate.

According to another aspect of the invention, methods of assaying a sample are provided. The methods include (a) detecting in a sample determined to have at least one tdh and trh polynucleotide comprising a nucleic acid sequence set forth as SEQ ID NO: 15, 16, 17, 18, 19, 20, 32, 33, 34, 35, 110, 111, 112, 113, 114, 115, 116, 117, 118, 119, 120 or 121, or a variant thereof, and a level of at least one: (i) ST36prp polynucleotide comprising at least one of the nucleic acid sequences set forth as SEQ ID NO:1, 2, 3, 4, 5, 6, 7, 21, 22, 23, 24, 25, 26, 122, 123, 124, 125, 126, 127, 128, 129, 130, 131, 132, 133, 134, 135, 136, 137, 138 or 139, or a variant thereof; (ii) ST36flp polynucleotide comprising at least one of the nucleic acid sequences set forth as SEQ ID NO: 36, 37, 38, 39, 40, 140, 141, 142, 143, 144, 145, 146, 147, 148, 149 or 150, or a variant thereof; (iii) ST631end polynucleotide comprising at least one of the nucleic acid sequences set forth as: SEQ ID NO: 151, 152, 153, 154, 155, 156, 157, 158, 159, 160, 161, 162 or 163, or a variant thereof; and (iv) 631-ENV polynucleotide comprising at least one of the nucleic acid sequences set forth as: SEQ ID NO: 59, 60, 61, 62, 170, 171, 172, 173, 174 or 175, or a variant thereof; and (b) comparing the level of the detected polynucleotide in at least one of steps (i), (ii), (iii), and (iv) to a control level of the detected polynucleotide in steps (i), (ii), (iii), and (iv), respectively. In some embodiments, the method also includes (c) determining the presence of a difference between the detected polynucleotide level and the control level of the detected polynucleotide as compared in (b); and (d) identifying the presence or absence of the pathogenic *V. parahaemolyticus* in the sample, based at least in part on difference between the level of the detected polynucleotide of at least one of steps (i), (ii), (iii), and (iii) and the respective control level of the detected polynucleotide. In some embodiments, assaying the sample comprises identifying the presence of a pathogenic *V. parahaemolyticus* in a sample. In some embodiments, the method also includes detecting an additional amplification control polynucleotide in the sample. In certain embodiments, the nucleic acid sequence of the variant of the tdh, trh, ST36prp, ST36fl, ST631end and ST631-ENV polynucleotide has at least 85%, 90%, 95%, 97%, 98%, 99%, or 100% sequence identity to the nucleic acid sequence of the polynucleotide of which it is a variant thereof. In some embodiments, the variant of the nucleic acid sequence comprises a fragment of the nucleic acid sequence. In some embodiments, the variant of the nucleic acid sequence comprises a fragment of the nucleic acid sequence and the fragment has at least 85%, 90%, 95%, 97%, 98%, 99%, or 100% sequence identity to the region of the nucleic acid sequence with which it aligns. In some embodiments, the sample is obtained from at subject. In certain embodiments, the sample is obtained from a substrate.

According to another aspect of the invention, methods of identifying the status of a pathogenic *V. parahaemolyticus* in a sample are provided. The methods including: (a) detecting in a sample a level of at least one of (a) a ST36Phage polynucleotide comprising a nucleic acid sequence set forth as SEQ ID NO 81, 82, 83 or 84, or a or a variant thereof; (b) a ST36PhHypD-Orf9 polynucleotide comprising a nucleic acid sequence set forth as SEQ ID NO:94, 95, 96 or 97, or a variant thereof; (c) a ST36NEOrf10-Hyp polynucleotide comprising a nucleic acid sequence set forth as SEQ ID NO: 87, 88, 89 or 90, or a variant thereof; and (d) a tlh polynucleotide comprising a nucleic acid sequence set forth as SEQ ID NO: 12 or 14, or a variant thereof; (b) comparing the level of the detected ST36Phage polynucleotide, ST36PhHypD-Orf9 polynucleotide, ST36NEOrf10-Hyp polynucleotide, and tlh polynucleotide to a control level of the detected ST36Phage polynucleotide, ST36PhHypD-Or19 polynucleotide, ST36NEOrf10-Hyp polynucleotide, and tlh polynucleotide, respectively; and (c) identifying the status of a pathogenic *V. parahaemolyticus* in the sample, based at least in part on the difference between the level of the detected ST36Phage polynucleotide, ST36PhHypD-Or19 polynucleotide, ST36NEOrf10-Hyp polynucleotide, and tlh polynucleotide, and the control level of ST36Phage polynucleotide, ST36PhHypD-Orf9 polynucleotide, ST36NEOrf10-Hyp polynucleotide, and tlh polynucleotide, respectively. In some embodiments, a higher level of the detected ST36Phage polynucleotide compared to the control level of the detected ST36Phage polynucleotide and the presence of a higher level of one or more of the ST36PhHypD-Orf9 polynucleotide and the ST36NEOrf10-Hyp polynucleotide identifies the status of the pathogenic *V. parahaemolyticus* as present in the sample. In some embodiments, the control level of one or more of the detected ST36Phage polynucleotide, ST36PhHypD-Orf9 polynucleotide, and the ST36NEOrf10-Hyp polynucleotide is zero. In some embodiments, the method also includes detecting in the sample a level of at least one of a polynucleotide comprising a ST36prp nucleic acid sequence or variant thereof, a tlh nucleic acid sequence or variant thereof, a tdh nucleic acid sequence or variant thereof, a trh nucleic acid sequence or variant thereof, and an ST36cps nucleic acid sequence or variant thereof. In certain embodiments, the nucleic acid sequence of the variant of the SEQ ID NO: 81, 82, 83, 84, 94, 95, 96, 97, 87, 88, 89, 90, 12 or 14 nucleic acid sequence has at least 85%, 90%, 95%, 97%, 98%, 99%, or 100% sequence identity to the nucleic acid sequence of which it is a variant. In some embodiments, the variant of the nucleic acid sequence comprises a fragment of the nucleic acid sequence. In some embodiments, the variant of the nucleic acid sequence comprises a fragment of the nucleic acid sequence and the fragment has at least 85%, 90%, 95%, 97%, 98%, 99%, or 100% sequence identity to the region of the nucleic acid sequence with which it aligns. In some embodiments, the sample is obtained from a subject. In certain embodiments, the sample is obtained from a substrate.

According to an aspect of the invention, methods of identifying the status of a pathogenic *V. parahaemolyticus* in a sample are provided, the methods including: (a) detecting in the sample, the level of at least one ST631end polynucleotide comprising at least one nucleic acid sequence set forth as SEQ ID NO: 53, 54, 55, 56, 57, 58, 151, 152, 153, 154, 155, 156, 157, 158, 159, 160, 161, 162 or 163, or a variant thereof; (b) comparing the level of the detected ST631end polynucleotide to a control level of the detected ST631end polynucleotide; and (c) identifying the presence of the pathogenic *V. parahaemolyticus* in the sample, based at least in part on a difference between the level of the detected ST631end polynucleotide and the control level of the detected ST631end polynucleotide. In some embodiments, a higher level of the detected ST631end polynucleotide compared to the control level of the detected ST631end polynucleotide identifies the status of the pathogenic *V. parahaemolyticus* as present in the sample. In some embodiments, the control level of the detected ST631end polynucleotide is zero. In some embodiments, the method also includes detecting in the sample a level of at least one of a polynucleotide comprising an ST631-ENV nucleic acid sequence or variant thereof, an ST34reg nucleic acid sequence or variant thereof, a ST674hyp nucleic acid sequence or variant thereof, a ST1127hyp nucleic acid sequence or variant thereof, a ST36Phage nucleic acid sequence or variant thereof, an ST36NEOrf1O-Hyp nucleic acid sequence or variant thereof, a ST36PhHypD-Orf9 nucleic acid sequence or variant thereof, a TdhUreG nucleic acid sequence or variant thereof, a ST36cps nucleic acid sequence or variant thereof, a ST36prp nucleic acid sequence or variant thereof, a tlh nucleic acid sequence or variant thereof, a tdh nucleic acid sequence or variant thereof, a trh nucleic acid sequence or variant thereof, a ST36flp nucleic acid sequence or variant thereof, and an ORF8 nucleic acid sequence or variant thereof. In some embodiments, the nucleic acid sequence of the variant of the ST631end, ST631-ENV, ST34reg, ST674hyp, ST1127hyp, ST36Phage, ST36NEOrf10-Hyp, ST36PhHypD-Or19, TdhUreG, ST36cps, ST36prp, tlh, tdh, trh, ST36flp, ORF8 polynucleotide has at least 85%, 90%, 95%, 97%, 98%, 99%, or 100% sequence identity to the nucleic acid sequence of the polynucleotide of which it is a variant thereof. In certain embodiments, the variant of the nucleic acid sequence comprises a fragment of the nucleic acid sequence. In some embodiments, the variant of the nucleic acid sequence comprises a fragment of the nucleic acid sequence and the fragment has at least 85%, 90%, 95%, 97%, 98%, 99%, or 100% sequence identity to the region of the nucleic acid sequence with which it aligns. In some embodiments, the sample is obtained from a subject. In certain embodiments, the sample is obtained from a substrate. In some embodiments of any of the aforementioned aspects of the invention, detecting comprises performing a polymerase chain reaction (PCR) to detect the level of the least one polynucleotide comprising an ST36prp nucleic acid sequence or variant thereof, an ST36cps nucleic acid sequence or variant thereof, a ST36flp nucleic acid sequence or variant thereof, ST631end nucleic acid sequence or variant thereof, ST631-ENV nucleic acid sequence or variant thereof, a ST34reg nucleic acid sequence or variant thereof, a ST674hyp nucleic acid sequence or variant thereof, a ST1127hyp nucleic acid sequence or variant thereof, a ST36Phage nucleic acid sequence or variant thereof, a ST36NEOrf1O-Hyp nucleic acid sequence or variant thereof, a ST36PhHypD-Orf9 nucleic acid sequence or variant thereof, and a TdhUreG nucleic acid sequence or variant thereof. In some embodiments, the PCR comprises qPCR. In certain embodiments, an oligonucleotide probe in the qPCR comprises a detectable label. In some embodiments, the oligonucleotide probe comprises a nucleic acid sequence set forth herein as: SEQ ID NO: 127, 128, 129, 130, 143, 144, 155, 156 or 170, or a variant thereof, wherein the variant has an 85%, 90%, 95%, 97%, 98%, 99%, or 100% sequence identity to the nucleic acid sequence of the polynucleotide of which it is a variant thereof. In some embodiments of any of the aforementioned aspects of the invention, detecting includes performing in situ hybridization to measure the level of the at least one polynucleotide comprising an ST36prp nucleic acid sequence or variant thereof, an ST36cps nucleic acid sequence or variant thereof, a ST36flp nucleic acid sequence or variant thereof, ST631end nucleic acid sequence or variant thereof, ST631-ENV nucleic acid sequence or variant thereof, a ST34reg nucleic acid sequence or variant thereof, a ST674hyp nucleic acid sequence or variant thereof, a ST1127hyp nucleic acid sequence or variant thereof, a ST36Phage nucleic acid sequence or variant thereof, a ST36NEOrf1O-Hyp nucleic acid sequence or variant thereof, a ST36PhHypD-Orf9 nucleic acid sequence or variant thereof, and a TdhUreG nucleic acid sequence or variant thereof. In some embodiments of any of the aforementioned aspects of the invention, detecting includes performing DNA hybridization to measure the level of the at least one polynucleotide comprising a ST36prp nucleic acid sequence or variant thereof, an ST36cps nucleic acid sequence or variant thereof, a ST36flp nucleic acid sequence or variant thereof, ST631 end nucleic acid sequence or variant thereof, ST631-ENV nucleic acid sequence or variant thereof, a ST34reg nucleic acid sequence or variant thereof, a ST674hyp nucleic acid sequence or variant thereof, a ST1127hyp nucleic acid sequence or variant thereof, a ST36Phage nucleic acid sequence or variant thereof, a ST36NEOrf1O-Hyp nucleic acid sequence or variant thereof, a ST36PhHypD-Orf9 nucleic acid sequence or variant thereof, and a TdhUreG nucleic acid sequence or variant thereof. In certain embodiments, the DNA hybridization is DNA microarray hybridization. In some embodiments of any of the aforementioned aspects of the invention, the method also includes one or more of selecting a therapeutic agent to reduce a pathogenic *V. parahaemolyticus* infection in the subject; and administering a therapeutic agent to treat a pathogenic *V. parahaemolyticus* infection in the subject, based at least in part on the identified status of the pathogenic *V. parahaemolyticus* in the sample. In some embodiments of any of the aforementioned aspects of the invention, the method also includes one or more of selecting an agent to reduce a pathogenic *V. parahaemolyticus* contamination of the substrate; and contacting the substrate with an agent selected to reduce a pathogenic *V. parahaemolyticus* contamination of the substrate, based at least in part on the identified status of the pathogenic *V. parahaemolyticus* in the sample obtained from the substrate. In certain embodiments of any of the aforementioned aspects of the invention, the presence of the pathogenic *V. parahaemolyticus* in the sample comprises the presence of one or more pathogenic *V. parahaemolyticus* bacteria in the sample. In some embodiments, the agent is an anti-*V. parahaemolyticus* agent. In some embodiments of any of the aforementioned aspects of the invention, the subject is at least one of: suspected of having a pathogenic *V. parahaemolyticus* infection and diagnosed with a pathogenic *V. parahaemolyticus* infection. In some embodiments of any of the aforementioned aspects of the invention, the subject is a vertebrate, and optionally is a mammal. In certain embodiments of any of the aforementioned aspects of the invention, the subject is an invertebrate. In some embodiments of any of the aforementioned aspects of the invention, the sample comprises one or more of a skin sample, fluid sample, tissue sample, stool sample, pus sample, gastric sample, emesis sample, inflammatory exudate sample, blood sample, or lymph sample. In some embodiments of any of the aforementioned aspects of the invention, the sample is a cultured sample. In certain embodiments of any of the aforementioned aspects of the invention, the substrate is at least one of: known to have been exposed to a *V. parahaemolyticus* bacteria, suspected of being contaminated with a *V. parahaemolyticus* bacteria; and identified as being contaminated with a *V. parahaemolyticus* bacteria. In some embodiments of any of the aforementioned aspects of the invention, reducing the pathogenic *V. parahaemolyticus* contamination of the substrate comprises reducing the level of the pathogenic *V. parahaemolyticus* bacteria on the substrate. In some embodiments of any of the aforementioned aspects of the invention, the substrate comprises a liquid and the liquid optionally comprises water. In certain embodiments of any of the aforementioned aspects of the invention, the substrate comprises one or more of a metal, wood, plastic, glass, cork, fiber, a polymer, or a fabric. In some embodiments of any of the aforementioned aspects of the invention, the substrate comprises a food substance, and wherein the food substance optionally comprises shellfish. In some embodiments of any of the aforementioned aspects of the invention, the substrate comprises at least a portion of a tool, work surface, a medical device, body of water, clothing, skin, tissue, an edible substance, a beverage, or a food. In some embodiments of any of the aforementioned aspects of the invention, the substrate is a contaminated substrate and comprises one or more pathogenic *V. parahaemolyticus* bacteria. In certain embodiments of any of the aforementioned aspects of the invention, the sample comprises a fluid sample, semisolid sample, aqueous sample, or tissue sample.

According to another aspect of the invention, kits for performing a method of any embodiment of any aforementioned aspect of the invention are provided, the kits including: at least one a container comprising an oligonucleotide primer the sequence of which has at least 90%, 95%, 99%, or 100% sequence identity to at least one of SEQ ID NO: 2-7, 9, 10, 36, 37, 52, 53, 59, 60, 63, 64, 75, 76, 81, 82, 87, 88, 94, 95, 122-126, 140-142, 151-154, 170, 171 and 172; wherein the kit additionally comprises instructions for detecting a status of a *V. parahaemolyticus* polynucleotide in a sample. In some embodiments, the *V. parahaemolyticus* polynucleotide is a pathogenic *V. parahaemolyticus* polynucleotide. In certain embodiments, the status comprises one or more of: the presence or absence of the polynucleotide; and a level of the polynucleotide. In some embodiments, the kit comprises one or more of: (a) a container comprising an oligonucleotide primer the sequence of which has at least 90%, 95%, 99%, or 100% sequence identity to SEQ ID NO:2 and a container comprising an oligonucleotide primer the sequence of which has at least 90%, 95%, 99%, or 100% sequence identity to SEQ ID NO:3; (b) a container comprising an oligonucleotide primer the sequence of which has at least 90%, 95%, 99%, or 100% sequence identity to SEQ ID NO:4 and a container comprising an oligonucleotide primer the sequence of which has at least 90%, 95%, 99%, or 100% sequence identity to SEQ ID NO:5; (c) a container comprising an oligonucleotide primer the sequence of which has at least 90%, 95%, 99%, or 100% sequence identity to SEQ ID NO:6 and a container comprising an oligonucleotide primer the sequence of which has at least 90%, 95%, 99%, or 100% sequence identity to SEQ ID NO:7; (d) a container comprising an oligonucleotide primer the sequence of which has at least 90%, 95%, 99%, or 100% sequence identity to SEQ ID NO:9 and a container comprising an oligonucleotide primer the sequence of which has at least 90%, 95%, 99%, or 100% sequence identity to SEQ ID NO:10; (e) a container comprising an oligonucleotide primer the sequence of which has at least 90%, 95%, 99%, or 100% sequence identity to SEQ ID NO:36 and a container comprising an oligonucleotide primer the sequence of which has at least 90%, 95%, 99%, or 100% sequence identity to SEQ ID NO:37; (f) a container comprising an oligonucleotide primer the sequence of which has at least 90%, 95%, 99%, or 100% sequence identity to SEQ ID NO:53 and a container comprising an oligonucleotide primer the sequence of which has at least 90%, 95%, 99%, or 100% sequence identity to SEQ ID NO:54; (g) a container comprising an oligonucleotide primer the sequence of which has at least 90%, 95%, 99%, or 100% sequence identity to SEQ ID NO:59 and a container comprising an oligonucleotide primer the sequence of which has at least 90%, 95%, 99%, or 100% sequence identity to SEQ ID NO:60; (h) a container comprising an oligonucleotide primer the sequence of which has at least 90%, 95%, 99%, or 100% sequence identity to SEQ ID NO:63 and a container comprising an oligonucleotide primer the sequence of which has at least 90%, 95%, 99%, or 100% sequence identity to SEQ ID NO:64; (i) a container comprising an oligonucleotide primer the sequence of which has at least 90%, 95%, 99%, or 100% sequence identity to SEQ ID NO:69 and a container comprising an oligonucleotide primer the sequence of which has at least 90%, 95%, 99%, or 100% sequence identity to SEQ ID NO:70; (j) a container comprising an oligonucleotide primer the sequence of which has at least 90%, 95%, 99%, or 100% sequence identity to SEQ ID NO:75 and a container comprising an oligonucleotide primer the sequence of which has at least 90%, 95%, 99%, or 100% sequence identity to SEQ ID NO:76; (k) a container comprising an oligonucleotide primer the sequence of which has at least 90%, 95%, 99%, or 100% sequence identity to SEQ ID NO:122 and a container comprising an oligonucleotide primer the sequence of which has at least 90%, 95%, 99%, or 100% sequence identity to SEQ ID NO:123; (1) a container comprising an oligonucleotide primer the sequence of which has at least 90%, 95%, 99%, or 100% sequence identity to SEQ ID NO:124 and a container comprising an oligonucleotide primer the sequence of which has at least 90%, 95%, 99%, or 100% sequence identity to SEQ ID NO:125; (m) a container comprising an oligonucleotide primer the sequence of which has at least 90%, 95%, 99%, or 100% sequence identity to SEQ ID NO:126; (n) a container comprising an oligonucleotide primer the sequence of which has at least 90%, 95%, 99%, or 100% sequence identity to SEQ ID NO:140 and one or more of a container comprising an oligonucleotide primer the sequence of which has at least 90%, 95%, 99%, or 100% sequence identity to SEQ ID NO:141, and a container comprising an oligonucleotide primer the sequence of which has at least 90%, 95%, 99%, or 100% sequence identity to SEQ ID NO:142; (o) a container comprising an oligonucleotide primer the sequence of which has at least 90%, 95%, 99%, or 100% sequence identity to SEQ ID NO:151 and a container comprising an oligonucleotide primer the sequence of which has at least 90%, 95%, 99%, or 100% sequence identity to SEQ ID NO:152; (p) a container comprising an oligonucleotide primer the sequence of which has at least 90%, 95%, 99%, or 100% sequence identity to SEQ ID NO:153 and a container comprising an oligonucleotide primer the sequence of which has at least 90%, 95%, 99%, or 100% sequence identity to SEQ ID NO:154; and (q) a container comprising an oligonucleotide primer the sequence of which has at least 90%, 95%, 99%, or 100% sequence identity to SEQ ID NO:171 and a container comprising an oligonucle-otide primer the sequence of which has at least 90%, 95%, 99%, or 100% sequence identity to SEQ ID NO:172. In some embodiments, the kit also includes one or more oligonucleotide probes. In some embodiments, one or more of the oligonucleotide primers and probes is linked to one or more detectable labels. In certain embodiments, the detectable label comprises one or more of a radioactive molecule, a luminescent molecule, a chemiluminescent molecule, biotin, an enzyme, a His tag, or an exogenous nucleic acid sequence. In some embodiments, the link is an indirect link. In some embodiments, the detectable label comprises: Hexachloro-Fluorescein (HEX), VIC fluorescent dye, 4-5-Dichloro carboxy fluorescein (JOE), Cy3 fluorescent dye, or TexasRed (TxRed).

According to yet another aspect of the invention, compositions that include a polynucleotide having a sequence set forth as SEQ ID NO: 2-7, 9, 10, 12, 13, 21-30, 36, 37, 40, 53-56, 59, 60, 63-66, 69-72, 81-84, 87-91, 94-97, 100-103, 122-174, 175, or another polynucleotide sequence disclosed herein, or a variant of any thereof are provided. In certain embodiments, the polynucleotide is linked to one or more detectable labels. In some embodiments, the detectable label comprises one or more of a radioactive molecule, a luminescent molecule, a chemiluminescent molecule, biotin, an enzyme, a His tag, or an exogenous nucleic acid sequence. In some embodiments, the link is an indirect link. In certain embodiments, the detectable label comprises: Hexachloro-Fluorescein (HEX), VIC fluorescent dye, 4-5-Dichloro carboxy fluorescein (JOE), Cy3 fluorescent dye, or TexasRed (TxRed).

According to yet another aspect of the invention, methods of identifying a test compound as an agent to reduce one or both of pathogenic *V. parahaemolyticus* in subject and pathogenic *V. parahaemolyticus* contamination of a substrate are provided, the methods including: (a) identifying the level of a pathogenic *V. parahaemolyticus* bacteria in a first portion of a sample using a method of any embodiment of any of the aforementioned methods of the invention; (b) contacting a second portion of the sample of (a) with a test compound; (c) incubating the contacted second portion of the sample with the test compound; (d) identifying the level of the pathogenic *V. parahaemolyticus* bacteria in the incubated second portion of the sample; and (e) comparing the level of the pathogenic *V. parahaemolyticus* bacteria in the first portion of the sample to the level of the pathogenic *V. parahaemolyticus* bacteria in the incubated second portion of the sample, wherein a decrease in the level of the pathogenic *V. parahaemolyticus* bacteria in the incubated second portion of the sample compared to the control level identified in step (a) identifies the test compound as a candidate compound to treat a pathogenic *V. parahaemolyticus* infection in a subject or as a candidate compound to reduce a pathogenic *V. parahaemolyticus* contamination of a substrate. In some embodiments, the incubation is at least 1 min, 5 min, 30 min, 1 hour, 6 hours, 12 hours, or 18 hours in duration. In some embodiments, the method also includes: confirming efficacy of the candidate compound for treating a subject having or at risk of having the pathogenic *V. parahaemolyticus* infection or for reducing contamination of a substrate by the pathogenic *V. parahaemolyticus* bacteria. In certain embodiments, the control level detected in step (a) is greater than zero. In some embodiments, detecting the level of the pathogenic *V. parahaemolyticus* bacteria in the sample comprises detecting in the sample, the level of a pathogenic *V. parahaemolyticus* polynucleotide of the pathogenic *V. parahaemolyticus* bacteria.

According to yet another aspect of the invention, methods of identifying the status of a pathogenic *V. parahaemolyticus* infection in a subject are provided wherein the methods include any embodiment of any of the aforementioned methods to identify a *V. parahaemolyticus* in a sample. According to yet another aspect of the invention, methods of identifying the status of a pathogenic *V. parahaemolyticus* contamination of a substrate are provided wherein the methods include any embodiment of any of the aforementioned methods to identify a *V. parahaemolyticus* in a sample. Polynucleotides listed in Table 2, Table 3, and in the Brief Description of the sequences may be used in embodiments of the aforementioned methods, kits, and compositions.

The present invention is not intended to be limited to a system or method that must satisfy one or more of any stated objects or features of the invention. It is also important to note that the present invention is not limited to the exemplary or primary embodiments described herein. Modifications and substitutions by one of ordinary skill in the art are considered to be within the scope of the present invention.

BRIEF DESCRIPTION OF SEQUENCES

```
SEQ ID NO: 1 nucleic acid sequence of ST36prp
gtgaaaataaaaaacgtacgaattaaaaactatcgtctgctcaaagatgt
gtcattttcgattgatgaaaaaacaaccattattgttgggcgtaacaata
ctgggaaaacttcatttgctgaggcttttcgcagctttctgaatcatgct
ggtcccaaggtgcgttatgaggatttcaatcaatcctgtcgtcaggttt
cgaagatgcgctgaatgctcatcaaggcggagctgaagacgatgttgtga
ggcccatgcttccaactatcgagctagagttacttatcaattataaagaa
aatgcggacgaatatggtgtcctcggcgacttttattatcgattttaacga
tcaattatttgaaaccattatcctgatttcttatcagttaaaagacggca
agatcggcgattttttttagtgggctcgataccatcaaacgaaagcagtat
ttttcggatctgagggcgaggatagagcattactacgaagctacagttta
cgcggtcgagccgacaaaccagagcaacaaagcacggcttgagttttcgt
catttaaaaaattgctgctgtcgggtcttataaatgcacaacgcggttta
gatgacgaaacgcacaatgaacgtgatgtgcttggtaagtcgttaggtaa
tattttcaaaagtgcgagtagtgttggtgcgccagaagatttaaggcgca
atcagctgaaattcataatgtcgtcgaaggattacaacaagttgttgata
ctgactttcaggcaagagtgaaagctctacttcccaccttaaatattttt
ggatatccgggtctgcacgatccaaatttaagcgcagcaacagagcttaa
tgtgaaatcactgctggaaagtcacacccgagtgttttatcaacgagatg
accatttttacattgccagaaacctataacgggctgggaatgcggaatctg
atctttatcctcttccgaattatgagtatttccgtgagtttcaaagcca
tcaaacgccaccgaaagggcatgtaattttcatagaagagcccgaggcac
atcttcacccgcaaatgcaggaagtatttattcgacagcttgagcaaatt
gttgagcagttccagcgcgaactaaataaccagcaggtgtggcctgtaca
atttattgtgagtactcattcctcgcatattgccaacgaagctgatttta
gcaaggttcgttatttcctatccaaaaatggaaatggaaccaaagttaag
gatctgggcgttgctttccaaagtgccgaagcagcgggcgacaaagagtt
tttgcataaatacctgacgctcacaaaatgcgacctgtattttgcagacc
gagcgatcctcgttgaaggggcgactgaaaggatattgttgcctcaaatg
attaaaaaagttgacgcagctttagggactaactgttacctgtcacctt
gtcagtcgtcgaaattggtggagatatgcacaccacttctacaaattcat
agatttccttgagataaaaccctattattactgacttagacgcagttgat
tcaaaacaacatcatgccgctgtaatggtgagccaaggggacaggtcgag
taacgtcggcatttcaaaatggtttggcgaggagggttattctgacttag
ctactattagagctaaagattcagattctaaaattctcggatatcggcga
cttgcttttcaggtagatgaagatgttagtggtttatgcggccgcagatt
gaagatgcatttatcttggttaatagccagttattccagctaaataactt
aactggttccgcacttgaggccgctgtttatgacaaggcaaaagatatcg
gcaaaagagcaaagctgattttgctattgaatattgtataagtaatacg
gattggctcgtcccaagtatatccaagaagggtgcgcatggttagacga
agacccaacagttgctgttgaaggagtgcaatcatga SEQ ID NO: 8 nucleic acid sequence of ST36cps locus
atgttatgatcatgtctgatcttttgttgatcaagagctacaatcagaat
ttgggaaaataccaccaagttttttacctttaggaaataaaaggatttc
aacatcaattaaaactggctccgaaaaacagcattgtttacctgtcatta
ccagagtcattttttatttcgaatacagatgaaaaatggctaataaatca
gggagttagaatcttaaaaataccagagaatttgagtttaggagcatcgt
tagtagcatcgcttaacctttctgaacataacctagattctccatttagt
gtttttgtttggcgatacattattcaatgagttaccagttggtgaaaacat tatttgtgtttcagaaagtagtaatagctacaactgggctgtagtgacag
ataatgaaatgcactggcttactgatagtgaaaataaaattgactctaat
gtaagaaatattgtcaacggttatttccgttttagttcgccgagaaatat
tattcgctctattactcggagtaattgggagtttctagatgggcttaatg
aatatcataagataatagggtctcaccgcagtatattctaagcagtggtta
gactttggtcacgttaacacttactataactctaaagctcattttactac
tcaacgtgatttaatgaattgagaattacttccgattatgtagaaaaatc
gtcatttaaaagcaataaaattgcggcggaagccaattggttttcaacta
tccttattcactacgaaactatattcctcagtacctaggttctgagaaaa
ataatgagaaaataagatataagcttgaatacttatatcttactgcatta
aatgagctatatgtgtttagttcattaccagttaatacttgggagcaaat
tctaaggcaatgcatcgcatttattaaagattgccaacaagaaaaggccc
ctaatgattgtaattctaaccgtttagttgagttgtttggagataaaact
caagttcgattgaatgactattgtaatagccagaatatatctatgtcgac
acagtggatatttaatggagaagagaaagtatctttagaaggtattttga
cggaaactgaacgttatcttccaaaatcggatgaaaagaaatggccattg
tgtgtgttacatggtgattttgctttagtaatgtgctttatgactttag
atctaatcgtgttaaaactattgatcctagagggtatgaccttaacaggtg
aacaaacaatctatggcgacattcgatatgatattgcaaagttaagtcac
tcaatcataggtatgtatgattggattattgctggttactatgaagttga
tataaagggaaataatattaattttacaattgatgaaagtcatatacaaa
aaactattcaacagaagtttatcgagatggtgaaagtagaaattcgatctt
gaagcttctgaattaatagcaatgcagatccaattattcttgtctatgct
accacttcatcatgatgatattaatcggcaaaaagcactattcgctaatg
cgtttaaattatacttttaatgaaaaggttgtaa SEQ ID NO: 11 nucleic acid sequence of tlh locus
ttagaaacggtactcggctaagttgttgctactttctagcattttctctg
caacatagcggtgagttgctgttgttggatgcgtgacatcccagaacaca
aacttctcagcaccagacgctgcacactcagagcgcaatgcgtgggtgta
catgtaatcgacagacgatgagcggttgatgtccaaacaaggatcgctcg
cgttcacgaaaccgtgctcttctggcgcagaagttagcgtctcgaacaag
gcgtgagtatcaaacaacgtgatgttgtaaccttgcgctttgtagtacat
cgcttgtgccttgatgaactcgttcatctcaagcacttttcgcacgaattt
tgtcgatctcttcttgtgttgagtacttaaactgaggcgcttttcgtcgcg
tctggcagtgtcatcaacatgaagttcttcgcacctgcgtccgtcaaacg
aatcagtgatctgcataatctgattcacttctggaacgccacggttgtag
ttcatgaagtcattcaaaccaaactcaagcgtaaacaaggtgtttgctgg
tttgtagttatcgccagttttgcgtaggttaagtacgaagaaaacttgatc
accaacccctgttagcgcgatgtattggttctcaccagccgcgccgccaa
ctgcccagttgtagagcggaaggttcttcgctttggcaatgtattctgtc
cacacaaaaccgttggagaagtgacctaagaaccagctgttcgggttagg
gaagcgccattgtgatgcgttaaagatgttgcctgtatcagacaagctgt
caccgagtgcaaccactttgttgatttgatctggctgcattgctgcgtcg
ttgctccagatcgtgtggttgtatgagaagcgattgtcagcggcgaagaa
cgtaatgtctgcgttctcgttcgccaaatctaatgttgcttcacaacgct
gacggataacgttttgcgacgtgttggtgtagaacatgtttttaagtgaa
acggagctccaccagtagccgtcaatggtgaagtagctaccatcttcgtt
ttttgcccattcccaatcggtcgccggatcatctttcgagtagctggtgc
gataccaacagcgaacataggtataggtttggttttcttgcgtgctgatc
acttcagacgctgaaaccatttctggtgataaggttggctcttcggcaac
tgcagaagcaagcgggagtaatgcagttaatagtgtgattgttttttca
t SEQ ID NO: 15 nucleic acid sequence of tdh locus
atgaaagaaagaatcattaatctgttctggttgtgtttagagcaggggg
gagaattcttagttcattcttaattacgattctgatcgttaagcacctag
gggttgaacagtttggatcttttagtttagctcttgctatattgacagct
ttgggaccttttgctggtcttggatttgactcgattttattttaaaaaatt
tatcagcaatgaaggagatgaaaagacttttactagggataagctgctttt
caagattatttattgcactatcgatcattagttaactactttgataaat
ttaaacagtaatgctgtttatgttaatgtattaaacatactcgttctagg
ttttctatttgactcatttctagcatttaaagattatttcttgctaatc
ttaagaataagttttacacattttctacttttgtttcttcagtgattcaa
ttggctcttgtttatactttagtacaaaaaaatgctagcatagaatactt
cgcatggagctatgtattaacaaagttcatccaagcgttagtattaactt
gttcatattataaaattaggcaatcattaatatttccaatttggaacaaa
gagttatcaagaaaattagttataagatacttatccaatgatgctggccgc
gtctattggtttacttttatagtcttcaagaccaattttttattaaatact
ttcttggtgaatacgaacttgggttatactccgtaggcattaagtttatt
ctcattcttatcgtattaccaacactaatctctaacgtattttacccaag
cttagttaaaaaatttcattcaaataatattgaaatttataacaatcaat
tgcaggcgatatatttattattttttcattttaggttttgttactatttgcg
ttaatgtattttttcgtcggaaattgtaattgaaaaattattttgggactga
ttttgaacgatcaagttctatcatggaaatatattctatattactggtgg
tatcattctttcaatctctgaataataaaatattaatattaaataattta
caatcagttatttttaaaagagcagtcttttgcattaataacaaatgcaat
cttgaatctcttccttatacctaaatttggtattaaaggtgcagcttata
gtactgtgttatcagagatgttagtattaattagttatagatcagaaaag
```

```
atacaagatttattttaaccatcaaatgagagctatattttttgttaat
ttgttcaaaattgaaattataagaagtattaaaagatga
```

SEQ ID NO: 18 nucleic acid sequence of trh locus
```
atgaaactaaaactctactttgccttcagtttgctattggcttcgatatt
ttcagtatctaaatcattcgcgattgacctgccatccataccttttcctt
ctccaggttcggatgagctactatttgtcgttagaaatacaacaataaaa
actgaatcaccagttaacgcaatcgttgatgactactggacaaaccgaaa
cataaaacgaaaaccatataaaagcgttcacggtcaatctattttcacga
cttcaggcctcaaaatggttaagcgcctatatgacggtaaatattaatgga
ataactacacaatggctgctattctggctataaagatggcattcaacgg
tatcacaaaatcagaaaaaacaagcctaaatcagaactattcttctgtta
gtgatttcgttggtgagaatgaagaatcattgccaagtgtaacgtatttg
gatgaaacgccagaatatttcgtcaatgtcgaagcatatgagagcggaaa
tgggcatatgtttgttatgtgcattccaataaatcatctttgatgaat
gtatgtcacaaaattaa
```

SEQ ID NO: 38 nucleic acid sequence of ST36flp locus
```
atgaaagaaagaatcattaatctgttctggttgtgtttagagcaggggg
gagaattcttagttcattcttaattacgattctgatcgttaagcacctag
ggggttgaacagtttggatctttagtttagctcttgctatattgacagct
ttgggacctttgctggtcttggatttgactcgatttatttaaaaaatt
tatcagcaatgaaggagatgaaaagacttttactagggataagctgcttt
caagattatttattgcactatcgatcattagtttaactacttttgataaat
ttaaacagtaatgctgtttatgttaatgtattaaacatactcgttcagg
ttttctatttgactcatttctagcattttaaagattattttcttgctaatc
ttaagaataagttttacacattttctacttttgtttcttcagtgattcaa
ttggctcttgtttatactttagtacaaaaaaatgctagcatagaatactt
cgcatggagctatgtattaacaaagttcatccaagcgttagtattaactt
gttcatattataaaattaggcaatcattaatatttccaatttggaacaaa
gagttatcaagaaaattagttataagaatcttatccaatgatgctggccgc
gtctattggttacttttatagtcttcaagaccaatttttattaaaatact
ttcttggtgaatacgaactttgggttatactccgtaggcattaagttatt
ctcattcttatcgtattaccaacactaatctctaacgtattttacccaag
cttagttaaaaaatttcattcaaataatattgaaatttataacaatcaat
tgcaggcgatatatttattattttcatttaggtttgttactatttgcg
ttaatgtattttcgtcggaaattgtaattgaaaaattatttgggactga
ttttgaacgatcaagttctatcatggaaatatattctatattactggtgg
tatcattcttttcaatctctgaataataaaatattaatatttaaataattta
caatcagttattttttaaaagagcagtctttcgcattaataacaaatgcaat
cttgaatctcttcctttatacctaaatttggtattaaaaggtgcagcttata
gtactgtgttatcagagatgttagtattaattagttatagatcagaaaag
atacaagatttattttaaccatcaaatgagagctatattttttgttaat
ttgttcaaaattgaaattataagaagtattaaaagatga
```

SEQ ID NO: 41 is amino acid sequence of ST36prp, encoded by SEQ ID NO: 1
MKIKNVRIKNYRLLKDVSFSIDEKTTIIVGRNNTGKTSFAEAFRSFLNHA
GPKVRYEDFNQSCLSGEEDALNAHQGGAEDDVVRPMLPTIELELLINYKE
NADEYGVLGDFEDENDQLFETIIILISYQLKDGKIGDFFSGLDTIKRKQYF
SDLRARIEHYYEATVYAVEPTNQSNKARLEFSSFKKLLLSGLINAQRGLD
DETHNERDVLGKSLGNIFKSASSVGAPEAFKAQSAEIHNVVEGLQQVVDT
DFQARVKALLPTLNIFGYPGLHDPNLSAATELNVKSLLESHTRVFYQRDD
HFTLPETYNGLGMRNLIFILFRIYEYFREFQSHQTPPKGHVIFIEEPEAH
LHPQMQEVFIRQLEQIVEQFQRELNNQQVWPVQFIVSTHSSHIANEADFS
KVRYFLSKNGNETKVKDLGVAFQSAEAAGDKEFLHKYLTLTKCDLYFADR
AILVEGATERILLPQMIKKVDAALGTNLRQKYLSVVEIGGAYAHHEYKFI
DFLELKTLFITDLDAVDSKQHHAAVMVSQGDRSSNVGISKWFGEEGYSDL
ATIRAKDSDSKILGYRRLAFQVDEDVSGLCGRSFEDAFILVNSQLFQLNN
LTGSALEAAVYDKAKDIGKKSKADFAIEYCISNTDWLVPKYIQEGCAWLD
EDPTVAVEGVQS.

SEQ ID NO: 42 is amino acid sequence of ST36cps, encoded by SEQ ID NO: 8
MFLIMSASFVDQELQSEFGKIPPSFLPLGNKRLFQHQLKLAPKNSIVYLS
LPESFFISNTDEKWLINQGVRILKIPENLSLGASLVASLNLSEHNLDSPF
SVLFGDTLFNELPVGENIICVSESSNSYNWAVVTDNEMHWLTDSENKIDS
NVRNIVNGYFRFSSPRNIIRSITRSNWEFLDGLNEYHKIIGLTAVYSKQW
LDFGHVNTYYNSKAHFTTQRAFNELRITSDYVEKSSFKSNKIAAEANWFS
TLPYSLRNYIPQYLGSEKNNEKIRYKLEYLYLTALNELYVFSSLPVNTWE
QILRQCIAFIKDCQQEKAPNDCNSNRLVELFGDKTQVRLNDYCNSQNISM
STQWIENGEEKVSLEGILTETERYLPKSDEKKWPLCVLHGDFCFSNVLYD
FRSNRVKTIDPRGMTLTGEQTIYGDIRYDIAKLSHSIIGMYDWIIAGYYE
VDIKGNNINFTIDESHIQKTIQQKFIEMVKVEFDLEASELIAMQIQLFLS
MLPLHHDDINRQKALFANAFKLYFLMKRL.

SEQ ID NO: 43 is amino acid sequence of tlh, encoded by SEQ ID NO: 11
MKKTITLLTALLPLASAVAEEPTLSPEMVSASEVISTQENQTYTYVRCWY
RTSYSKDDPATDWEWAKNEDGSYFTIDGYWWSSVSLKNMFYTNTSQNVIR
QRCEATLDLANENADITFFAADNRFSYNHTIWSNDAAMQPDQINKVVALG
DSLSDTGNIFNASQWRFPNPNSWFLGHFSNGFVWTEYIAKAKNLPLYNWA
VGGAAGENQYIALTGVGDQVSSYLTYAKLAKNYKPANTLFTLEFGLNDFM
NYNRGVPEVKADYAEALIRLTDAGAKNFMLMTLPDATKAPQFKYSTQEEI
DKIRAKVLEMNEFIKAQAMYYKAQGYNITLFDTHALFETLTSAPEEHGEV
NASDPCLDINRSSSVDYMYTHALRSECAASGAEKFVFWDVTHPTTATHRY
VAEKMLESSNNLAEYRF.

SEQ ID NO: 44 is amino acid sequence of tdh, encoded by SEQ ID NO: 15
MLAAFKTFAFELPSVPFPAPGSDEILFVVRDATFNTNAPVNVKVSDFWTN
RNVKRKPYKDVYGQSVETTSGTKWLTSYMTVNINDKDYTMAAVSGYKRGH
SAVEVKSDQVQLQHSYNSVANFVGEDEDSIPSKMYLDETPEYFVNVEAYE
SGSGNILVMCISNKESFFECEHQK.

SEQ ID NO: 45 is amino acid sequence of trh, encoded by SEQ ID NO: 18
MKLKLYFAFSLLLASIFSVSKSFAIDLPSIPFPSPGSDELLFVVRNTTIK
TESPVNAIVDDYWTNRNIKRKPYKSVHGQSIFTTSGSKWLSAYMTVNING
NNYTMAALSGYKDGLSTVFTKSEKTSLNQNYSSVSDFVGENEESLPSVTY
LDETPEYFVNVEAYESGNGHMFVMCISNKSSFDECMSQN SEQ ID NO: 46 is amino acid sequence of ST36flp, encoded by SEQ ID NO: 38
MKERIINLFWLCLEQGGRILSSFLITILIVKHLGVEQFGSFSLALAILTA
LGPFAGLGFDSILFKKFISNEGDEKTLLGISCFSRLFIALSIISLTTLIN
LNSNAVYVNVLNILVLGELFDSFLAFKDYFLANLKNKFYTFSTFVSSVIQ
LALVYTLVQKNASIEYFAWSYVLTKFIQALVLTCSYYKIRQSLIFPIWNK
ELSRKLVIESYPMMLAASIGLLYSLQDQPFIKYFLGEYELGLYSVGIKFI
LILIVLPTLISNVFYPSLVKKEHSNNIEIYNNQLQATYLLFFILGLLLFA
LMYFSSEIVIEKLFGTDFERSSSIIVIEIYSILLVVSFFQSLNNKILILN
NLQSVIFKRAVFALITNAILNLFLIPKEGIKGAAYSTVLSEMLVLISYSF
RKDTRFIENHQMRAIFFVNLFKIEIIRSIKR SEQ ID NO: 57 is nucleic acid sequence of ST631 locus
```
Agttcatcaggtagagagttagaggaatatgtacagagtacgtatcgctt
tatctaaatatgaaagatgaaggtgtaactgtagagcgaaatatatactt
atctgaaagtctggagccaaacatcaaattgatgtctttttatgagttta
aaacagctggtattacacataggtagctattgaatgtaaagaccactca
cgcccagtggaaaagggaaggttcaagagtttgcatataaactgcaaga
tatcggtgggatttctggtgtcatggtatctcaagcagggtatcaatcag
gcgctgaattgattgctaagcaggcagatatcctgctgaaaactactgat
gaacttcctcctactccttggttaatggctgagaggttggaaagtgtagc
tcttccaacagaaaattacaggggggaaccattttgggtgatcatggagc
atagtgaaggtaaagttaatggctcatgatggtaacgaagataatggt
cgtaagttcataccttttttctccaaatatcatgctcaactaaattt
tgatgaaggtggacttgatgaatcttgttggtgtgttcgtggtttaccaa
ggcacgcttttagggcatttttgctgttactagaattatttgagcgccaa
aaggtcgagcctatgatgtcttgtttagacctcctggcgatactagtgaaat
aggctgggcagggttagttactacacgtgacttacttgtaaaagagtact
attgtgaagatctgcctagagtgctaaacaaatccgcttaa
```

SEQ ID NO: 58 is ST631 amino acid sequence
MSSSGRELEEYVQSTYRELLNMKDEGVTVERNIYLSGKSGAKHQIDVEYE
EKTAGITHRVAIECKDHSRPVEKGKVQEFAYKLQDIGGISGVMVSQAGYQ
SGAELIAKQADILLKTTDELPPTPWLMAERLESVALPTENYRGEPFWVIM
EHSEGKVNGSYYGNEDNGRKFIPLFFSKYHAQLNEDEGGLDESCWCVRGL
PRHAFRAELLLLELFERQKVEPMICFRPPGDTSEIGWAGLVTTRDLLVKE
YYCEDLPRVLNKSA.

SEQ ID NO: 67 is ST34reg nucleic acid sequence
```
atggatttgaacttaatcaatactttccttgttcgttgaatatcagtc
gtataccaaagcggcggaacacttaggggtaacacaacccgcaattagtg
catcgatgaaacgactagaacaactatctaacaaaaatctttttgttaga
aaagggcgaaatattgagttgacctcaaccgcacaccactgggttccatt
attcagacgagcattaagcataattaatgatgctgtcattgagcaagcca
cattcaagtctgctgtaccgaaccctcttttttcgagactgaccgcgtct
ccaagcttttcgttgcgtgcgctcctgtttcgtccctctccttacttga
cgatcttcgtctacacaaagtggactttggttattgacaacctccccacta
tagaaacctcatttgtatgtgagttggtatacgaagagccaattgtggtg
atttgccgtcaaggacatccacgtataactggcagtacatttaactcatc
aatgttctatgccgaacaacactgtgtattggttgatacggaatatcggg
cagtgaatcttggtggggcgctcctcgaccctacacaacatttacacata
```

```
ggcatgacaaccgtatctctatctggaatggtactgaacgtatctaagct
agactaccttggaatcttgccactctcttttgctagagaatggcaggatt
ctcttaaactacaaatattgccatgtcccataaaaagtcaatctattggt
tataatatgatttatcacaaaagagatgaacataatgttgcccaccaaaa
actgagaaggcaaattcgtcacgacctcgttcaaaacttgatggttagga
atttctga.

SEQ ID NO: 68 is ST34 amino acid sequence
MDLNLINTFLVVVEYQSYTKAAEHLGVTQPAISASMKRLEQLSNKNLFVR
KGRNIELTSTAHHWVPLFRRALSIINDAVIEQATFQVCCTEPSFSRLTAS
PSFSLRCAPVSSLSLLDDLRLHKVDLVIDNLPTIETSFVCELVYEEPIVV
ICRQGHPRITGSTENSSNIFYAEQHCVLVDTEYRAVNLGGALLDPTQHLH
IGMTTVSLSGMVLNVSKLDYLGILPLSFAREWQDSLKLQILPCPIKSQSI
GYNMIYHKRDEHNVAHQKLRRQIRHDLVQNLMVRNF.

SEQ ID NO: 73 is ST674 nucleic acid sequence
gaagatggtccaagagggaagcatagtctccctctttcaaaaagggataa
tttagaaaatctggttttactttgtaaaacgcatcataaattagttgacg
atcacgtagatgagttttcggttagtgatttgacaacactgagagaggag
cactttaaatgggtgtcaaataagtaaatgagcctaggcaatgggagtg
taacttaagtcagcttacttatattaatgtacctcgattatcgatgttat
cttctaggttgggctatgaagtagatttagatgaatacggtaagtttgaa
acattatattcactgcgttggtcgcttaataaattgatgaggcaattcgt
atcaacattaaacaagataaacgtgaatacattggacttttcctctgtta
actatcccgatatccggttggtggagctacttgctaatctctgat.

SEQ ID NO: 74 is ST674 amino acid sequence:
MAVLEKTRNMLWALSAGRCAYCKNKLVVESKKKNFSLVGEVAHIVAQKED
GPRGKHSLPLSKRDNLENLVLLCKTHHKLVDDHVDEFSVSDLTTLREEHF
KWVSNKLNEPRQWECNLSQLTYINVPRLSMLSSRLGYEVDLDEYGKFETL
YSLRWSLNKLMRQFLSTLNKINVNTLDFSSVNYPDIRLVGATCSISDSFR
TKNVPMIGRDDKDPVTFCGDLKKDPHIYKKYPNFKLVMRIQPSWITTSTA
FLAFRPSGGVSTFSGLITVSEVDVENSVIYAIPLVLGLPVSDFELMMKEP
KLFREEDSSVVGKKINKKTSLIEFEDLEKAIEQDTKYVNPPDCCDVCRAS
LENQTYFVDGAIKSSSAWAFLCEYCFEKDGVGIGWGLGQLFKKNKHNEWL
LVGGFAPESDDDYYI.

SEQ ID NO: 79 is nucleic acid sequence of ST1127
locus
cgtaaagtaaaagagcctggtcttgcatccaccggaattaatctatcttt
taggttaatagtacgaacaaactcaccgtatagggatgaccaaccatcta
gcactttagaaatgctgtttagttgcatagtccctcgacgactaggacga
gaaatgtcaaattcgtgatttacagatagaattgatttatccgttatccg
actcaatgtatctattctgaagtcgcatggtggaagatcctatctggat
atcttctgcagctaagatctcaatatatggttattaccatcgaatgcag
taaagattttgaaaattgaattttcttcagggtaaagaaaagcatctctc
aaaaggcgagaacctgtttcgagagatctctaatcgtttggcagacatagg
aacgtaaagccagacgtctccatcttctagtttcatctatccaataaacta
agaaatagaggcctaggcattcactacactaaatagtttaggcccatcg
tattatcgtagaccttatttatctctatagtgcctaagatttctcttgaa
ctaaagggtacattacatcattctatacattcgaatcgcgtgtgtggt
tcagagtccgttttaaaccatacagttatatggtggtggctccggttc
tttcatcactccgtcgtcttcaataagcgcgcccgttgacaatagatttg
tcgaagaggtttgaacaacttcttctttttgagcgcttctttttttctgag
tgaataacgatgagccataaagcatttctctatcagttggcttttcgct
tttcttccaggttttcttcaagtgtagaactaaaacaggtttttacagg
tggattactattccaccaatcggaaagctgttccagatgcagcgatcgcat
cttttggaggcatatcatcgggatagtaatctgggtaatcactcatacat
atgcacagttcgtaaaaaaacattgttgcatattagttaggttctattt
gttaatcaacggcctaatacgtgtttgtgtgatagaaatcgcttcctctg
atagatcattacccccaaaatttgcggtcatgactcaaagctgaaacacct
acagcgccagccccataaatgggtcacaaacaagttcgccttctgtcga
gctttgttttattagaatatccatcagttcaacgggttttcctgtaggat
aacctctatgaatgcgggaactgaa SEQ ID NO: 80 is nucleic acid sequence of ST631
hypothetical protein locus, which is expressed in
pathogenic and non-pathogenic V. parahaemolyticus
bacteria
ttttctggagataatgaattgagcagagaaatatacgatatggaacgacg
ctgtgttaataggcacaatgattagcgggtcacattaatcggatgagtc
agcagcaagctcgtatcatgacaaacgaaaatatagcggcgacaaaagaa
gtagttgctcacgtatacgaaaagctaactcttacagcaatgtaattat
tgctgctggttatgtcggtttctttacttatggtcaagtctaaaaagtg
atttacctcaatggctcatttaagctcaggcgcacttatactgatatca
ctgatgacatttataggattgaactataaaatgatcagtgtttcagt
acaaatgcacagagtctcaaaacggcttcaaaagcccgacatgtcgtctc
taagtgaaatacagctattgagcaaaaaagcgcactgattaacgctagg
gtctgggttttttacagttattccaacagttttgtcggatttggagccgg
```

SEQ ID NO: 85 nucleic acid sequence of MAVP-36
and MAVP-46 (Orf3 WP_005477619 to hyp WP_
047715660) and (any f237-like phage, ORF 3-5)
atgtctgtatgcgtcaccgtcgttaaccagtatggcaatttgaaagcaac
gaaaacgcctgttgcggattgccaagaatacgtgctgatttcggcggtgg
actaccagaataataaggaaccagtcctcttcaacggtgacttgttcctg
tatgtcagtggcgtgctcttgatcaacgtcgttggtcactgggtggg
tcgtgttgttcgccttatgagtaaaaggtaaatcttatgaaaaaactaga
acttgttgtaactaacgtaaaacacgcagtcgtaaacaaaaaaaccgcag
ctggcgctgctcttatggtcgcgtctgtctctccggccttcgctgaagtc
gatatcacgggcgcaatcaactcctgcgtatccggtggtcaagctaacgt
atcactggttgtgcgggtctaattgtatggctgcactgggctttgtg
tgaccatggttgttggcttatacgtcgctaacggttcacctctatgcctc
ctttatcgggtaatttacttggagatgttctcgctatcgttctaggtgtt
gcctttgcggggcattcctccacggctttgtgagtggcatcaatactca
ctaatcaacggataaaggggcttcggctccctttttttattggttttata
caatgaatcactatctccgttttttttattgtcctgttattctatgcgct
agtcatcatacgtatgcttagaagcacgtattagtcatatgcaaatgag
gggtgttggctctcaaggtgcttggttgaccatcaaggtgaatacttg
ttttttggatactgggtattcgactcatgcacatttgagaagacatcat
atgctaatgctcgcgatcctatcaaacagtttgtgataatgggctcggt
cttctttattctgaggtcgttgtccagaaaatagcgaatttgacccttc
aacctacgttgtaaatcggtttgtgaatatggcaagaaccctgacggca
cctgcatggatgcttgccagttcaaacagtccattggtgatacggtgaaa
ttgcattggcaccctgccatatacggcgaactggtgacaggcgcgtgcta
cggagactacggtgccactcgatgcgaagtgaccaaaaacgaatcctcca
ttatttgctactggcgttcctgatgacagtacacgcccgactctcaatgc
tctctgcgcttgcttacactggacgtcagtgtgacggtggcacactttt
ctggggcgtgaatgggccagacgagccaatcattccaccggatacgccag
aagacccaactcatgaccctgatgacccaacaggcgagattgaagaccca
agtgtcctaccgacgattcaaccaacacggttaatccggtgtcgttga
tgataaaccggatgtagaagaccctgacaggatgaatcgacagacacg
cagtccttttctgctattaaagggcttaacgtggatgtgaacaaaggcatt
catgatcttaacgtcgatatcaaccagtcacacgctgacatcaccaacgc
ggtgatgtgatgtgaaaggctcttggtcgataacaccccaagccattcaag
aacagcaaatcaatgacaacaagattttataacaacaccaaggcactcatc
caacaggccaacggcgatatcactacggcggtgaacaacaataccaacgc
caccattggtattcgtaacgatttaaagggcttggtgattcaatggcg
aactcgatagcagataaatgcgattgagggtctattgactggctcagagt
ttggtacacctacgggcaccgctatcactggcgaaatcttcacggcgaa
gactttgccaacctgcaaaccacgatagatgaaaaagccgaatccatcca
aggctatgtggacgatattaaaggcttaatcactatcggcaccaacttca
acaacggcacattaagcgacaagtcttttaacatcaaaggcgcaaccgtt
gaatcaggactacagcgttttgatgcgggtatcgggctacgtgcgccctgt
cgtgctgttcatttgtgccttaatcgcccttttgggttctgtttggtaatc
ggagtaaataa SEQ ID NO: 92 nucleic acid sequence of MAVP-26
Orf10-to Hypothetical A, (North East Atlantic
phage only, not 10290 phage)
taatttaacataataacataatgcagtctgataagggtcctgtgga
cttgcaatcactaaggccaatccagcacaagccattgaaatgcttgataa
tccaagtccgttaaactttttcctatgttctgccatagtgtctgcgctt
cgtgcgttttgctttatcctcgccaagccaatcagtgcctttctttg
tcttcaccaatagtttcagcaagcataagtatctgattttcattgagata

```
acttcgaccttttcttacttctgtgagcatttgagggcttacacctaggt
catgagcaatctgatgtattgaatgtagttcatttgctctttataagcat
caatgagcttgtttgtgtacatttctgcttttcctctaatcacgctattg
gactgattttagtcttttagtacagattttgctgtgttgacggtacagaa
atatctgtatttaatcgctacagaattactgtatcagaccgccttagct
ttgggcgtttgcccttgacgctttcgcgcttggctttggcggtcactctc
tcaactagtcaggtggttgtaatgatcgtattagaaactgaagttcaaaa
cgtcaatgttaaaacgttaacgctccgtcacttcgcagtgtctcacgttc
cagcttttcaaacttttgttacatcactacaactgacatctttgaagaagtc
gtcgttcattcaatcactttggctactgcattagcacattcgaaaacaac
caagagtcctttggttatctctcggttggcgattacgagtttcgctttga
atctgacgagcatgaagttctatgtcgtttcttaggcatgacaccttcaa
aagcgacggctttagaggctcagtaa.

SEQ ID NO: 93 nucleic acid sequence of MAVP-26
Orf10-to Hypothetical A, (North East Atlantic
phage only, not 10290 phage)
taatttaacataatatacataatgcgcactgatatagtggttcctgtgga
cttgcaatcactaaggccaatccagcacaagccattgaaatgcttgataa
tccaagtccgttaaacttttttcctatgttctgccacagtgtctgcgctt
cgtgcgttttgctttatccatagccaagccaatcagtgcctttttcttg
tcttcaccaatagtttcagcaagcataagtatctgattttcattgagata
acttcgaccttttcttacttctgtgagcatttgagggcttacacctaggt
catgagcaatctgatgtattgaatgtagttcatttgctctttataagcat
caatgagcttgtttgtgtacatttctgcttttcctctaatcacgctattg
gactgattttagtcttttagtacagattttgctgtgttgacggtacagaa
atatctgtatttaatcactacagaattactgtatcagaccgccttagct
ttgggcgtttgcccttgacgctttcgcgcttggctttggcggtcactctc
tcaactagtcaggtggttgtaatgatcgtattagaaactgaagttcaaaa
cgtcaatgttaaaacgttaacgctccgtcacttcgcagtgtctcacgttc
cagcttttcaaacttttgttacatcactacaactgacatctttgaagaagtc
gtcgttcattcaatcactttggctactgcattagcacattcgaaaacaac
caagagtcctttagttacctctcggttggcgattacgagtttcgctttga
atctgacgagcatgaagttctatgtcgtttcttaggcatgacaccttcaa
aagcgacggctttagaggctcagtaa.

SEQ ID NO: 98 is nucleic acid sequence of MAVP-26,
also referred to as Vipa 26. Region from HypD
(WP_047724020) to Orf9 (WP_047724015).
cgctaggttttatatgtcaaggatatgaaatggctaagttttttaaataca
agtgctacaaactactatctcgaagagcttattaagaatgcttccgaaag
actgattctaattagcccttttctcaagataatgatcgcattcgagagct
tttggaagacaaggaccgattaaaaatcgatattagaattgtctatggca
aaagcgaactacaaccggatgagattaactggcttaaaagcctctccttt
gtgcgtactagttttgtaaaaacctccatgcaaagtgctacatgaatga
aagtgatgtatcattacaagataaatctctatgagttcagccaagtaaac
aataatgaaatgggtatcttcattgaccgtgacgaagaccccaatgtcta
caaagattcctacgaggaagctcaacgcattattcgtattgtctatggca
aaagcgaactacaaccgaaagtcgagctgctaatttagatacggaacttc
actgaaaagcctgttacagataatgaactaattaaactcagctcctctaa
gttagccaaaaagcacaaacttaaaacagatgagtttctcagcttgtgtg
ttaataaaggatacttaacgttagatgacggaaagcactcattaaccgat
gaaggtaaatcttcaggtggtgagtttaaatacagcaaacgtttcggtcc
atattttgtctggccagagtccttggaagtatcgtaactattgggttcaa
tattttaaagtgagtacagcaaacatgaagattaaaataagagctatgtt
aagtttagctgccgccccttagtttgataggttgcacctccactaacttca
gtgaatataagggtctacctggccataagtccatagctgttggctctaat
ggcgttatcgcatattcctcatcgaagcccaatgccgaaacagccattac
aacagccattgataaatgctcttcaatcggtggcaaagattgtaagttta
tcgatgttgatggttatagtcctatcggtaataacatatatgtgatt
gatcgcgcagctagtgttgattacctagaaaaaggttcatacgcagtaag
gtataaatgtgagcaattaacgaaagcaatggcacaatcattatttcgtt
caggccatacttacctagatggagactcagatgggaagccttgtgagtca
aacctttggagctcatattattcgacagataccagtagcagaaaagcaaa
aggtactaactgtcattatgttcgtgggtatcgaagaaaaaatggtactt
atgtcagtggttatacacgctgtcgttgatttacaaggctccattcggag
cctttttttcatataattttctttaatactatgcatacttgagaatctgat
gcgcaatagcaatgtcatttgacgcacctaactcaagtaaagcaacccca
attaatacttgctgcgcagtaaccaactgtcctgttggaagttctaaccg
atcatgcctcattacgaagttttccccaatcttcacagctgctaagttccc
tacccttattcatctcgcatagcgttacactccggagggaatgaattttc
ccctgtcccattcctgatcgtcctcacagttttttaaacaaagtttggc
agcttcttcgacggttaaaccacattcaaattcacgaaaaatatagtttt
tagtcatttcgtgatacttcattgaattgtccctcaaaagagagacatttt
tataggatacgcatatgcaatcgcattcaacataagcgcccataatgcgc
accagg SEQ ID NO: 99 is nucleic acid sequence of MAVP-36,
also referred to as Vipa 36. Region from HypD
(WP_047724020) to Orf9 (WP_047724015).
Atggctaagttttttaaacacaagtgcaacaaactactacctcgaagaact
aattaagaacgcttctgaaaggctgatcctcatcagcccttttctcaagc
ttaatgatcgcattcgagagcttttggaagacaaagaccgattaaagata
gacattcgaattgtctatggcaaaagcgagctacaacctgatgagattaa
ctggcttaaaagcctctcattgtgcgtaccagtttttgcaaaaacctcca
tgcaaagtgctacatgaatgaaagtgcttgtatcattacaagtttaaacc
tctacgagtttagccaagtaaacaataacgaaatgggtatcttcattgac
cgtgacgaagaccccaatgtctacaaagattcctacgaggaagcgcaacg
cattattcgtattagtgatgaagttagaatctcgttagagaaagttgaag
ctgctaaattagatacggaatctactcaaaagcctgttacagagaatgaa
ctaattaaacttagttcctctaagttagctaaaaagcataaacttaaaac
agatgacttccttcagatgtgtgtaagcaagggctacttatctttcgaag
atggaaaacattctttaaccgaagaagggaaatcgttggtggtgagttc
aagtacagtaaacgttttggtccttacttttatctggccagagtcattaga
ggttgaatagaaaaataaggctcctgttggagccttcaatcacactattt
tctttagtattcttgcatacttcaatatttggtgagccacctttatatca
ttcgatgcacctaactcaagtaaagcaaccccaatcaatacttgctgcgc
agtaaccaactgtcctgttggaagctctaatcgatcatgcctcattacga
agttttcccaatcttcacaagagctcaattcctacccgtattcatcctc
atcaagcgcttacactctggaggaatggattttcccttgtcccattctttt
gaccgttctcacagttttttaaacaaagtttggcagcttcttcgacggtta
aaccacattcaaattcacgaaaaatatagtttttagtcatttcgtgatac
ttcattgaattgtccctcaaaagagagacattttataggatacgcatatg
caatcgcattcaacataagcgcc.

SEQ ID NO: 21 gccgaactcaaaagcagtaa.

SEQ ID NO: 22 ggtgtggacgaccaataaatcaag.

SEQ ID NO: 23 gggctccgtgtagaagtgg.

SEQ ID NO: 24 atttggtgattgtagaagtagatgg.

SEQ ID NO: 25 acgccttagactagaaataggag.

SEQ ID NO: 26 ttgacaacccagaagcagattgg.

SEQ ID NO: 27 aactcttaatgaaggctaatacatct.

SEQ ID NO: 28 atttgcgtaatcgcttatcacg.

SEQ ID NO: 29 tcttgaagtagaactactgtgacg.

SEQ ID NO: 30 tttcgcctaatacgtcttcgtgac.

SEQ ID NO: 31 cgatgaaagatcgtaaaagagacg.

SEQ ID NO: 32 catttccagagactgaaaacctg.

SEQ ID NO: 33 accttatcttggaagtagaagtgg.

SEQ ID NO: 34 gtattgtttgtatacgggtaaaggc.

SEQ ID NO: 35 aaccgaagctataaaagtcataga.

SEQ ID NO: 39 accaacacaaatctcgtccc.

SEQ ID NO: 40 acaaccattatgctattcttactct.

SEQ ID NO: 49 tcctgcgtcaatgcgaactac.

SEQ ID NO: 50 gattgcgtaacagggaaacatc.

SEQ ID NO: 51 ttgcgtaacagggaaacatc.

SEQ ID NO: 52 gattgcgtaacagggaaaca.

SEQ ID NO: 55 tcaagtagtccatctctcaatctcct.

SEQ ID NO: 56 agaagcaatggtatcatactcggt.

SEQ ID NO: 61 acccgcaatccgaaacg.

SEQ ID NO: 62 cccgaagatgctgaaagacga.
```

-continued

SEQ ID NO: 65 aggaacaacagcaacttatagtcag

SEQ ID NO: 66 ctatgccaacagtacggatacaca

SEQ ID NO: 71 cttctaccaggttctcccttcg

SEQ ID NO: 72 gatagtctctaactcgttcatcg

SEQ ID NO: 77 gcatttcattttctcggaccag

SEQ ID NO: 78 aagtcaaggggcgtaagta

SEQ ID NO: 83 tcgttgcttttgcggaca

SEQ ID NO: 84 tggcatagtggttacctgaca

SEQ ID NO: 86 gcatagtggtacctgaca

SEQ ID NO: 89 aaagaatgaagcactcgtaaact

SEQ ID NO: 90 ctaatgactcggagatttcggcag

SEQ ID NO: 91 aatgactcggagatttcggcag

SEQ ID NO: 96 ttcacgatgtacttactttcacga

SEQ ID NO: 97 agttacttcatagtgctttactgat

SEQ ID NO: 102 cttacgacggttgtacctatattta

SEQ ID NO: 103 ctgtttccatacgacggttttcac

SEQ ID NO: 107 tgagttgtgttcttctctagctgtt

SEQ ID NO: 108 ctactcgccaactacaggtt

SEQ ID NO: 109 gcgagcgcaagtgctttggca

SEQ ID NO: 113 agggaaaaggacggggg

SEQ ID NO: 114 gcgacggtaacatatcagaaatag

SEQ ID NO: 115 actgtaggatgtactgacac

SEQ ID NO: 119 aacgaaagtcaaacgataaccga

SEQ ID NO: 120 acaaatggcagtatatccgcgaa

SEQ ID NO: 121 tctttatgttgttagttttgact

SEQ ID NO: 131 actgcgtcgaaatccctgattgaat

SEQ ID NO: 132 gcgatttggtgattgtagaagtagatg

SEQ ID NO: 133 cgctcctcccaataagactgaatc

SEQ ID NO: 134 gattcagtcttattgggaggagcg

SEQ ID NO: 135 tttagatacttaaacatcttcaccacac

SEQ ID NO: 136 tatggacagtcagcagctttaaccacctc

SEQ ID NO: 137 tatggacagtcagcagctttaaccacct

SEQ ID NO: 138 tatggacagtcagcagctttaaccacct

SEQ ID NO: 139 gttgtagtacggcgacattaccactc

SEQ ID NO: 145 tgtagtacggcgacattaccactc

SEQ ID NO: 146 ttagacaagaccaacacaaatctcg

SEQ ID NO: 147 tttccagggtttcgacagttatatc

SEQ ID NO: 148 ttcagaaaagtagtggaagtaacg

SEQ ID NO: 149 gatcccaacttgtcaaacctagaaaatcaaat

SEQ ID NO: 150 gatcccaacttgtcaaacct

SEQ ID NO: 157 cgactctccaaccttctcacatcg

SEQ ID NO: 158 agaagcaatggtatcatactcggt

SEQ ID NO: 159 atagccaccctaaagaccaca

SEQ ID NO: 160 gtaattggttcctcatcctccttca

SEQ ID NO: 161 cccactagtacctcgtatcacttccattt

SEQ ID NO: 162 agagttcgtcccatagttagtccgc

SEQ ID NO: 163 agagttcgtcccatagttagtccgc

SEQ ID NO: 167 ctgtagctatacccacggc

SEQ ID NO: 168 gctctgctacgtcggtaag

SEQ ID NO: 169 agagtacgcagagggaccacttacac

SEQ ID NO: 173 aacccgcaatccgaaacgcatgt

SEQ ID NO: 174 actatcagcaccaacgcacg

SEQ ID NO: 175 tcgacttagccaaaccaatgt.

BRIEF DESCRIPTION OF THE DRAWINGS

FIG. 4 provides a listing of diagnostic loci in all available draft genomes of *V. parahaemolyticus*. Note "a": For all high quality draft genomes which had no sequence type identified in www.pubMLST.org, the sequence type was identified using the SRST2 program (Inouye M, et al., (2012). *BMC Genomics* 13:338); Unk: sequence type is not known due to new sequence type or incomplete sequences at the 7 loci, n/a: Information was unavailable. Note "b": Location of reported infection or isolation by US state; Note "c": source identified as clinical (C) or environmental (E); Note "d": year of isolation; Note "e" only partial coding sequence for cps identified from this genome.

FIG. 8 provides a table of ST loci in the left column, additional identifying information in the center column and associated GenBank® Accession numbers in the right column.

DETAILED DESCRIPTION

Figure 1:
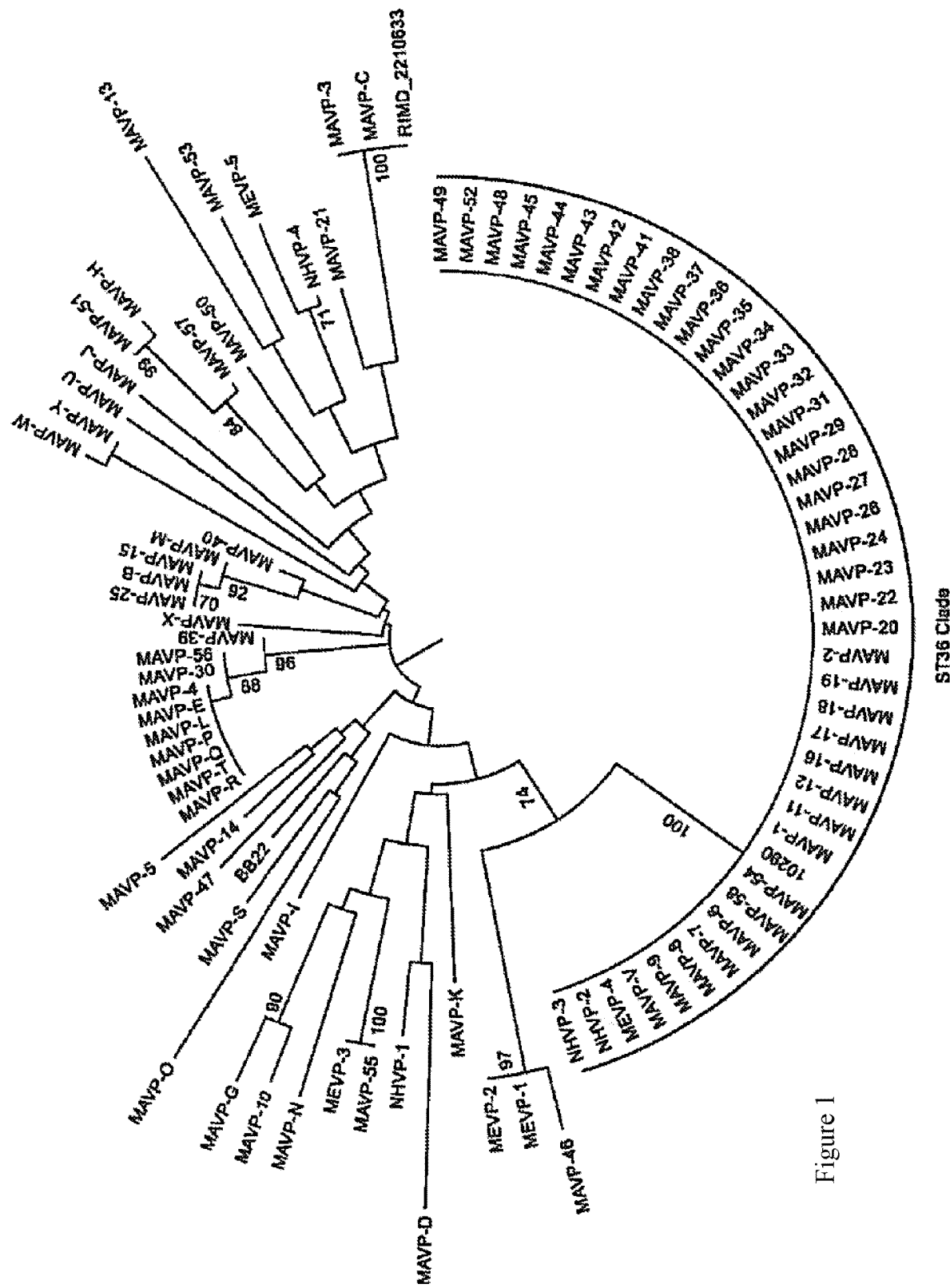
FIG. 1 provides a diagram showing identification of ST36 12 clade strains from among northern New England clinical isolates of *V. parahaemolyticus*. A consensus neighbor-joining tree was constructed from four concatenated housekeeping gene loci including dnaE, dtdS, pntA, and tnaA sequences (1868 bp) by using a Jukes-Cantor model, with statistical support assessed by 1,000 bootstrap re-assemblies to identify all ST36 complex strains. The bar indicates 0.2% divergences, and branches with less than 70% bootstrap support are unlabeled.

Definitive markers of virulence have now been identified for *V. parahaemolyticus*, and assays have been developed that allow identification pathogenic *V. parahaemolyticus* known to cause infections in subjects and to contaminate substrates. In certain aspects of the invention, assays are provided that can be used to identify the status of infection of a subject with, or contamination of a substrate with *V. parahaemolyticus* bacteria. In some aspects of the invention, methods include determining one or more of the presence and level of a pathogenic *V. parahaemolyticus* bacterium in a sample. A sample assayed using methods and compositions of the invention may be obtained from a variety of different sources such as, but not limited to: cells, tissues, subjects, and substrates. In certain aspects of the invention, the identification of status of a pathogenic *V. parahaemolyticus* polynucleotide in a sample may be extrapolated to identify the presence of the pathogenic *V. parahaemolyticus* bacterium in the cell, tissue, or subject, or substrate from which the sample was obtained. The presence of pathogenic *V. parahaemolyticus* bacterium may indicate infection or contamination of the source of the sample such as the cell, tissue, subject or the substrate by the pathogenic *V. parahaemolyticus* bacterium. Thus, some embodiments of the invention include methods of determining whether a cell, tissue or subject has, or is at risk of having, a pathogenic *V. parahaemolyticus* infection and certain embodiments of the invention include methods of determining whether a substrate is contaminated by, or is a risk of contamination by a pathogenic *V. parahaemolyticus* bacterium.

The invention in some aspects also includes methods to monitor treatment of a pathogenic *V. parahaemolyticus* infection in a cell, tissue, or subject and to monitor decontamination of a substrate contaminated by a pathogenic *V. parahaemolyticus* bacterium. Thus, some aspects of the invention include methods such as assays to identify changes in a level of a pathogenic *V. parahaemolyticus* bacterium in a sample. In instances in which a sample is obtained from a cell, tissue, or subject and/or from a substrate, methods of the invention may be used to monitor treatment of infection or contamination of the cell, tissue, or subject or a substrate, respectively, by pathogenic *V. parahaemolyticus* bacterium. The invention also provides in some aspects, methods useful to characterize one or more compounds to determine whether or not they may be useful to treat a pathogenic *V. parahaemolyticus* infection or to reduce or eliminate contamination by a pathogenic *V. parahaemolyticus* bacterium. Certain methods of the invention may be used to determine efficacy, cell toxicity, and other characteristics of compounds that may be used to treat a pathogenic *V. parahaemolyticus* infection or to reduce or eliminate pathogenic *V. parahaemolyticus* contamination of a substrate.

Pathogenic *V. parahaemolyticus* bacteria are rod-shaped, gram-negative, motile bacteria that are found in brackish water and saltwater. They can be found in organisms such as seafood, shellfish that when eaten by a subject, can cause gastrointestinal illness. Entry of the bacteria into a subject may also occur through contact with water that contains the pathogenic *V. parahaemolyticus* bacteria and thus can cause infections via contact with open wounds and handling of contaminated substrates such as shellfish, materials, liquids, etc. Outbreaks of *V. parahaemolyticus* bacterial infections generally occur along coastal regions during times when the water temperature supports high bacterial levels. Infection in a subject may be indicated by severe diarrhea, nausea, vomiting, abdominal pain, and fever and can last from 2 to 10 days. Subjects or substrates that have infection by or contamination with pathogenic *V. parahaemolyticus* bacteria may spread the disease, via contact by another subject, for example, transmission from body fluids, diarrhea, or by contact with wounds, food, beverages, etc. Although most infections are not life-threatening, deaths do result from pathogenic *V. parahaemolyticus* infection.

Pathogenic *V. parahaemolyticus* bacteria are a cause of a growing number of cases of food-borne illnesses. Methods and tools of the invention that can be used to determine (also referred to herein as "to identify") the status of a pathogenic *V. parahaemolyticus* infection or contamination may, in some embodiments include determining the presence, absence, and/or level or quantity of the pathogenic *V. parahaemolyticus* bacteria in or on a cell, tissue, subject, and/or substrate have now been identified. Such methods of the invention may be used in identify disease or risk of disease or contamination or risk of contamination by pathogenic *V. parahaemolyticus*. Disease or contamination by a pathogenic *V. parahaemolyticus* bacteria are conditions characterized by abnormal (e.g., increased) levels of the pathogenic *V. parahaemolyticus* bacteria. With respect to a pathogenic *V. parahaemolyticus* level in a sample, as used herein a "normal" level would be no detectable pathogenic *V. parahaemolyticus* bacteria as determined using a method of the invention, and an "abnormal" level would be a detectable level of pathogenic *V. parahaemolyticus* bacteria determined using a method of the invention. As used herein, with respect to the level of a pathogenic *V. parahaemolyticus* bacteria, the terms: "increased", "elevated", and "higher" are used interchangeably, and the terms "decrease", "reduced", and "lower" are used interchangeably.

Methods and assays set forth in certain embodiments of the invention can be used to identify the status of, and evaluate and compare levels of pathogenic *V. parahaemolyticus* bacteria in samples, or in some embodiments of the invention, in or on subjects and substrates. Methods in some aspects of the invention may include detecting in a sample the presence and/or level of one or more specific polynucleotides and/or polypeptides that have now been identified as biomarkers for pathogenic *V. parahaemolyticus* bacteria. Information obtained using methods of the invention can be used to identify the status of infection of a subject or contamination of a substrate by a pathogenic *V. parahaemolyticus* bacterium and may be used to select a treatment for a subject and to select an agent with which to reduce contamination of a substrate.

As used herein the term "status" with respect to a pathogenic *V. parahaemolyticus* in a sample, may mean presence, absence, or level of the pathogenic *V. parahaemolyticus* in the sample. In certain embodiments of the invention the status of a pathogenic *V. parahaemolyticus* in a sample is binary, and is determined to be either present or absent using a method of the invention. In certain embodiments of the invention, a status may be a level of a pathogenic *V. parahaemolyticus* bacteria in a sample, and may be a difference in a level between two or more samples, and or between a sample and a control. In some aspects of the invention, a determination of a level greater than zero of a pathogenic *V. parahaemolyticus* polynucleotide in a sample indicates the presence of a pathogenic *V. parahaemolyticus* in the sample and in the source from which the sample was obtained. In some embodiments the source from which a sample is obtained is a subject and in certain embodiments of the invention, the source is a substrate. In certain aspects of the invention, a status of a pathogenic *V. parahaemolyticus* in a sample may be used to determine a status of a pathogenic *V. parahaemolyticus* bacterial infection in a subject from whom the sample was obtained, or a pathogenic *V. parahaemolyticus* bacterial contamination of a substrate from which the sample was obtained.

As used herein the term "status" with respect to infection or contamination may mean presence, absence, onset, end, recurrence, progression, regression, increase, decrease, or other indication of the state of the infection or contamination by the pathogenic *V. parahaemolyticus* bacteria. For example, in certain embodiments of the invention the status of infection or contamination is binary, and is determined to be either present or absent using a method of the invention. In certain embodiments of the invention, a status may be the state of progression of infection or contamination, which can be determined by testing a first sample obtained from a subject or substrate and testing a second sample obtained from the subject or substrate, respectively, wherein the second sample is obtained from the subject or substrate at a later point in time. An increase in the level of a pathogenic *V. parahaemolyticus* bacteria determined in the second sample compared to the level determined in the first sample indicates the status of progression or increase of the infection or contamination of the subject or substrate by the pathogenic *V. parahaemolyticus* bacteria. A determination of a level of zero of a pathogenic *V. parahaemolyticus* bacteria in a first sample obtained from a subject or substrate followed by a determination of a level greater than zero of the pathogenic *V. parahaemolyticus* bacteria in a sample subsequently obtained from the subject or substrate, respectively, may indicate a status of onset of the infection or contamination of the subject or substrate, respectively, by the pathogenic *V. parahaemolyticus* bacteria. Similarly, a decrease in the level of a pathogenic *V. parahaemolyticus* bacteria determined in a sample obtained from a subject or substrate at a later time point compared to that determined in a sample obtained from the subject or substrate, respectively, at an earlier time point would indicate a status of regression or decrease of the infection or contamination with the pathogenic *V. parahaemolyticus* bacteria. A determination of a level of a pathogenic *V. parahaemolyticus* bacteria that is greater than zero in a first sample obtained from a subject or substrate followed by determination of a zero level of the pathogenic *V. parahaemolyticus* bacteria in a sample subsequently obtained from the subject or substrate, respectively, indicate a status of the infection or contamination of the subject or substrate, respectively, by the pathogenic *V. parahaemolyticus* bacteria as ended or resolved.

Some embodiments of the invention provide methods that may be diagnostic and/or prognostic for infection with or contamination by pathogenic *V. parahaemolyticus* bacteria. Methods of the invention, in some aspects, utilize detection of the identified nucleic acid and/or polypeptide biomarkers to determine the presence and/or level of the bacteria in biological samples obtained from subjects, culture, and/or substrates. It has now been identified that increased presence of signature pathogenic *V. parahaemolyticus* molecules in or on a cell, tissue, subject, or substrate is correlated with infection or contamination of the cell, tissue, subject, or substrate with the pathogenic *V. parahaemolyticus* bacteria.

As used herein, the term "*V. parahaemolyticus* molecule" means a polynucleotide or polypeptide naturally expressed by a *V. parahaemolyticus* bacterium and the term "pathogenic *V. parahaemolyticus* molecule" means a polynucleotide or polypeptide naturally expressed by a pathogenic *V. parahaemolyticus* bacterium. As used herein, a "signature" pathogenic *V. parahaemolyticus* molecule refers to a polynucleotide or polypeptide that is naturally expressed by a pathogenic *V. parahaemolyticus* bacterium and is not naturally expressed by a non-pathogenic *V. parahaemolyticus* bacterium.

In an infection of a cell, tissue, or subject with, or contamination of a substrate by, pathogenic *V. parahaemolyticus* bacteria, the level of the pathogenic bacteria is statistically significantly higher in that cell, tissue, subject, or substrate as compared to the level of the pathogenic bacteria in cells, tissues, subjects, or substrates that do not have the infection or contamination. It has now been identified that the presence and/or level of a signature pathogenic *V. parahaemolyticus* polynucleotide or polypeptide of the invention in a sample obtained from a subject or substrate correlates with the presence and/or level of the pathogenic *V.*

*parahaemolyticus* bacteria in the subject or substrate, respectively. In an infection of a cell, tissue, or subject with a pathogenic *V. parahaemolyticus* bacteria, and in contamination of a substrate with a pathogenic *V. parahaemolyticus* bacteria, the level of a signature pathogenic *V. parahaemolyticus* polynucleotide or polypeptide of the invention is statistically significantly higher in or on the cell, tissue, subject, or substrate as compared to the level of the signature pathogenic *V. parahaemolyticus* polynucleotide or polypeptide in a cell, tissue, subject, or substrate not infected with or contaminated by the pathogenic *V. parahaemolyticus* bacteria. Thus, detecting a level of a signature pathogenic *V. parahaemolyticus* polynucleotide or polypeptide of the invention in a sample obtained from a subject or substrate permits identification of the status of the infection of the subject with the pathogenic *V. parahaemolyticus* bacteria, and permits identification of the status of the contamination of the substrate with the pathogenic *V. parahaemolyticus* bacteria, respectively.

In some embodiments of the invention detection of an amount greater than zero and/or the presence of a signature pathogenic *V. parahaemolyticus* polynucleotide or polypeptide in a sample identifies the status of the source (for example, the subject or substrate) of the sample as infected and/or contaminated with the pathogenic *V. parahaemolyticus* bacteria. In some embodiments of the invention, the level of a signature pathogenic *V. parahaemolyticus* polynucleotide or polypeptide in a control sample is zero, which means the absence of the pathogenic *V. parahaemolyticus* bacterium. In certain embodiments of the invention, any detected level of a signature pathogenic *V. parahaemolyticus* polynucleotide or polypeptide of the invention that is greater than zero in a sample need not be compared to a control because a level greater than zero confirms the presence of the pathogenic *V. parahaemolyticus* bacterium in the sample.

Methods of the invention, in some embodiments, may include detecting a level of a pathogenic *V. parahaemolyticus* polynucleotide (and hence bacteria) in a sample and comparing the detected level to one or more of: a level of zero, a control level, and a prior level in a biological sample from the same subject or substrate. For example in some aspects of the invention, a method may include detecting a level of a pathogenic *V. parahaemolyticus* bacterium in a sample and the sample was obtained from a subject that has, is suspected of having, is susceptible to having, or is at risk of having an infection by the pathogenic *V. parahaemolyticus* bacterium.

As used herein, the term "level" when used in reference to detecting a level of a *V. parahaemolyticus* polynucleotide, polypeptide, or bacterium means: (a) a quantitative value such as an amount, weight, or concentration of the polynucleotide, polypeptide, or bacterium; or (b) the "presence" or "absence" of the polynucleotide, polypeptide or bacterium. It will be understood that in certain embodiments of the invention, the presence or absence of a *V. parahaemolyticus* polynucleotide, polypeptide, or bacterium is detected as a binary determination, without quantification. Thus, detecting may include one or more of determining the presence or absence of a pathogenic *V. parahaemolyticus* bacterium polynucleotide or polypeptide molecule; and determining a quantity of a pathogenic *V. parahaemolyticus* bacterium polynucleotide or polypeptide molecule. Means for detecting levels of polypeptides and polynucleotides and for determining amino acid and nucleic acid sequences are known in the art and non-limiting examples of detection means are provided herein.

In certain aspects of the invention, a level of a pathogenic *V. parahaemolyticus* bacterium in/on a subject or substrate can be detected using methods of the invention to measure the pathogenic *V. parahaemolyticus* bacterium polynucleotide and/or polypeptide molecule (for example, one or more biomarker polynucleotides or polypeptides) in an in vitro assay of a biological sample obtained from the subject or substrate, respectively. As used herein, the term "measure" used in reference to measuring a level of a *V. parahaemolyticus* polynucleotide comprising a nucleic acid sequence means: (a) determining a quantitative value, such as an amount, weight, concentration, relative amount, relative concentration, etc., of a polynucleotide comprising the nucleic acid sequence; or (b) determining the "presence" or "absence" of a polynucleotide comprising the nucleic acid sequence. It will be understood that in certain embodiments of the invention, the presence or absence of a *V. parahaemolyticus* polynucleotide is measured as a binary determination, without quantitation. Thus, measuring may include one or more of determining the presence or absence of a pathogenic *V. parahaemolyticus* bacterium polynucleotide or polypeptide molecule; and determining a quantity of a pathogenic *V. parahaemolyticus* bacterium polynucleotide or polypeptide molecule. Means for measuring levels of polypeptides and polynucleotides and for determining amino acid and nucleic acid sequences are known in the art. Non-limiting examples of measuring means are provided herein.

Detection methods suitable for use in certain embodiments of methods of the present invention can be used to detect and measure levels of pathogenic *V. parahaemolyticus* bacterium polypeptide or nucleic acid molecules in samples (also interchangeably herein as biological samples) in vitro as well as in vivo. For example, in certain embodiments of the invention in vitro techniques for detecting and/or measuring levels of pathogenic *V. parahaemolyticus* polynucleotides (genes) include but are not limited to: polymerase chain reaction methods, reverse transcriptase quantitative polymerase chain reaction (RT-qPCR), Northern hybridizations, in situ hybridizations, DNA or oligonucleotide array, sequencing, etc. In certain aspects of the invention in vitro techniques for detecting and/or measuring levels of pathogenic *V. parahaemolyticus* bacterium DNA include, but are not limited to: polymerase chain reaction (PCR) and Southern hybridizations. In vitro techniques for detecting and/or measuring levels of pathogenic *V. parahaemolyticus* bacterium polypeptides in certain embodiments of the invention include, but are not limited to enzyme linked immunosorbent assays (ELISAs), Western blots, immunoprecipitations, immunofluorescence, and other known suitable techniques.

In some embodiments of the invention, methods may include comparing a level of a pathogenic *V. parahaemolyticus* polynucleotide or polypeptide molecule in a sample to a control value or level for the pathogenic *V. parahaemolyticus* polynucleotide or polypeptide molecule. As used herein a "control" may be a normal control or an infection or contamination control. Selection and use of appropriate controls in comparative, diagnostic, and assay methods are well known in the art. In some embodiments of the invention, a normal control level may zero and represent the amount in a subject or substrate free of the pathogenic *V. parahaemolyticus* bacterium. A control level of a pathogenic *V. parahaemolyticus* molecule can readily be determined by measuring a level of the pathogenic *V. parahaemolyticus* polynucleotide or polypeptide molecule using a method of the invention, as described herein. In some embodiments of the invention, an infection or contamination control level may be obtained from a sample from a subject or substrate known have infection with or contamination by, respectively, the pathogenic *V. parahaemolyticus* bacterium. In some embodiments, a disease control pathogenic *V. parahaemolyticus* bacterium level may be based on levels obtained from one or more subjects known to have the infection, or one or more surfaces known to have contamination with the pathogenic *V. parahaemolyticus* bacterium. In certain embodiments of the invention, the disease control may be a sample from a subject diagnosed with a pathogenic *V. parahaemolyticus* infection and the subject's disease control may be compared to another sample obtained from the subject at a different time. In certain embodiments of the invention, a disease control level of a pathogenic *V. parahaemolyticus* molecule can readily be determined by measuring levels of the pathogenic *V. parahaemolyticus* molecule in a sample obtained from a subject known to have a pathogenic *V. parahaemolyticus* infection, or obtained from a substrate known to have a pathogenic *V. parahaemolyticus* contamination.

In some embodiments of the invention, a control level of pathogenic *V. parahaemolyticus* is a level determined from samples, subjects, substrates, tissues, cells, etc. that do not have contamination by or infection by the pathogenic *V. parahaemolyticus* bacteria that is being tested for in the sample. For example, in some embodiments, a control level of pathogenic *V. parahaemolyticus* molecule is a level determined in a normal sample that does not have contamination by the pathogenic *V. parahaemolyticus* bacteria that is suspected to be in the sample obtained from the subject or substrate. In such a case, the presence of infection and/or contamination by the pathogenic *V. parahaemolyticus* can be determined based on an increase in the level of the pathogenic *V. parahaemolyticus* polynucleotide or polypeptide in the subject's or substrate's sample as compared to the control that is free of the pathogenic *V. parahaemolyticus*. In another embodiment of the invention, the control is from a normal subject or substrate and the test sample is from a subject or substrate that is suspected of having infection with or contamination by a pathogenic *V. parahaemolyticus* bacteria.

In some aspects of the invention methods are provided that include comparing a level of a pathogenic *V. parahaemolyticus* molecule measured a biological sample obtained from a subject, or substrate to a control value for determining infection or contamination status, stage, prognosis, etc. Changes over time in the presence and/or level of a pathogenic *V. parahaemolyticus* molecule in a subject or substrate can be assessed by determining levels in two or more samples obtained from a subject or substrate at different times. Values obtained from a sample obtained at one time can be compared to values obtained from samples obtained at other times. For example, a first level obtained from a subject may serve as a baseline level or control level for that subject, thus allowing comparison of the pathogenic *V. parahaemolyticus* molecule level and the determination of change or stability of the pathogenic *V. parahaemolyticus* infection over time. Levels of a pathogenic *V. parahaemolyticus* molecule may also be measured after a specific course of treatment of the pathogenic *V. parahaemolyticus* infection or contamination has been initiated, with the intent of determining the efficacy of that treatment of the subject or the decontamination of the substrate, or just the natural change of the level of the pathogenic *V. parahaemolyticus* bacteria in or on a subject or substrate over time. For example, though not intended to be limiting, samples may be obtained from a substrate such as a body of water, at different times of the year and the levels of a signature pathogenic *V. parahaemolyticus* polynucleotide or polypeptide determined to assess changes in the contamination of the substrate over time. Thus, the status of infection with or contamination by a pathogenic *V. parahaemolyticus* bacterium in a subject or substrate can be monitored over time using aspects of methods of the invention to assess change in levels of one or more pathogenic *V. parahaemolyticus* molecules.

In some aspects of the invention, assessing a change in at least one of the presence, absence, and level of a pathogenic *V. parahaemolyticus* molecule in a subject or substrate may be desirable, and methods of the invention may be used to monitor the level of the pathogenic *V. parahaemolyticus* bacteria in biological samples obtained from the subject or substrate over time to assess changes. Some aspects of the invention include methods to monitor the level of a pathogenic *V. parahaemolyticus* molecule over time to assess changes in the level. A decrease in a level of the pathogenic *V. parahaemolyticus* bacteria over time may be indicated by a level of the pathogenic *V. parahaemolyticus* molecule that, in a second biological sample is less than 100%, 99%, 95%, 90%, 85%, 80%, 75%, 70%, 65%, 60%, 55%, 50%, 45%, 40%, 35%, 30%, 25%, 20%, 15%, 10%, 5%, or 1% of the level identified in a first biological sample obtained from the subject or substrate at a prior time point than the time at which the second sample was obtained. An increase in a level of a pathogenic *V. parahaemolyticus* bacterium over time may be indicated by a level of the pathogenic *V. parahaemolyticus* molecule that, in second biological sample is more than 100%, 101%, 105%, 110%, 115%, 120%, 125%, 130%, 140%, 150%, 160%, 170%, 180%, 190%, 200%, 500%, 1000%, 10,000% of the level identified in a first biological sample obtained from the subject or substrate at a prior time point, including all percentages in between those stated. A higher level of increase, for example 200%, 400%, 600%, 1000% or higher increase may indicate the severity of the infection or contamination with a higher percent increase corresponding to a more severe infection or contamination. An increase in a level of a pathogenic *V. parahaemolyticus* molecule between a first and second sample may also indicate the progression of a pathogenic *V. parahaemolyticus* infection or contamination. In embodiments where the level of a pathogenic *V. parahaemolyticus* molecule was zero in a first biological sample, any level over zero in the second biological sample indicates an increase in a level of the pathogenic *V. parahaemolyticus* bacteria and in some embodiments may indicate the onset of infection or contamination in a subject or substrate, respectively. It will be understood that if zero pathogenic *V. parahaemolyticus* molecules are detected in a sample, any level of detection in a subsequent sample that is greater than zero indicates an increase. Similarly, if any level of a pathogenic *V. parahaemolyticus* molecule is detected in an initial sample and no pathogenic *V. parahaemolyticus* molecules are detected in a subsequent sample, it indicates a decrease.

Samples (also referred to herein as biological samples) may be obtained from a subject or substrate at any desired interval such as at least once per day, every other day, once per week, every other week, once per month, every other month, every third month, every year, etc. It will be understood that interval testing using methods of the invention may be performed to assess the level of a pathogenic *V. parahaemolyticus* bacteria to determine information including, but not limited to: the likelihood of infection from a substrate, reinfection of a substrate, reinfection of a subject, decreased contamination of a substrate, carrier status of a subject, etc.

Assessment of efficacy of candidate agents to treat subjects or de-contaminate substrates that have been contacted with a pathogenic *V. parahaemolyticus* bacterium may also be done according to some embodiments of the invention, such as, in a non-limiting example, screening assays to assess candidate agents or compounds to reduce or eliminate pathogenic *V. parahaemolyticus* bacteria from a subject or substrate. It will be understood that a therapeutic regimen or decontamination regime may be either prophylactic or a treatment of an existing pathogenic *V. parahaemolyticus* infection or contamination of a subject or substrate, respectively. The invention in some aspects provides methods that may be used to monitor a subject's or substrate's response to prophylactic treatment provided to a subject or substrate. Some embodiments of the invention may include methods to assess treatments intended to reduce, prevent, or eliminate pathogenic *V. parahaemolyticus* bacteria and/or to provide an indicator of a status of a pathogenic *V. parahaemolyticus* infection or contamination, and in some embodiments of the invention, can be used to select one or more therapies for the subject, or one or more decontamination treatments for the substrate, for example, to select a drug therapy, disinfection protocol, etc. In some aspects, methods of the invention may include one or more of selecting a treatment for a subject or substrate and treating a subject or substrate for a pathogenic *V. parahaemolyticus* infection or contamination based at least in part on the results of an assay of the invention.

Assays for assessing pathogenic *V. parahaemolyticus* bacteria levels in certain embodiments of the invention may include determining one or more pathogenic *V. parahaemolyticus* molecule levels, including but not limited to determining levels of signature polynucleotides that encode pathogenic *V. parahaemolyticus* polypeptides and/determining levels of pathogenic *V. parahaemolyticus* polypeptides in cells, tissues, subjects, and substrates. Levels of pathogenic *V. parahaemolyticus* polynucleotides and polypeptides can be determined in a number of ways when carrying out various embodiments of methods of the invention. In some embodiments of the invention, a level of a pathogenic *V. parahaemolyticus* polynucleotide acid or polypeptide is measured in relation to a control level of the polynucleotide or polypeptide, respectively, in a biological sample from at least one of a cell, tissue, subject, and substrate. One possible measurement of the level of pathogenic *V. parahaemolyticus* polynucleotide or polypeptide is a measurement of an absolute level of the polynucleotide or polypeptide. This could be expressed, for example, in the level of the polynucleotide or polypeptide per unit of cells or tissue. Another measurement of a level of a pathogenic *V. parahaemolyticus* polynucleotide or polypeptide is a measurement of a change in the level of the polynucleotide or polypeptide over time. This may be expressed in an absolute amount or may be expressed in terms of a percentage increase or decrease over time. Methods disclosed herein may be used in embodiments of the invention to assess pathogenic *V. parahaemolyticus* polypeptide and polynucleotide molecules to assess the status of infection in a subject and contamination of a substrate and/or the efficacy of treatments for such infection and/or contamination.

As used herein a "subject" refers to an animal, such as, but not limited to a human, a non-human primate, a rodent, a dog, cat, a fish, a bird, or other animal. Thus, in addition to human medical application, some aspects of the invention include veterinary application of methods described herein.

In certain aspects of the invention a subject is an invertebrate, including but not limited to a shellfish, including but not limited to a clam, oyster, or mussel. A subject may be suspected of being infected with a pathogenic *V. parahaemolyticus* bacterium and methods of the invention can be used to measure the pathogenic *V. parahaemolyticus* molecules in a biological sample from the subject, thus the subject may be diagnosed with the infection by the pathogenic *V. parahaemolyticus* bacteria. In some embodiments of the invention, a subject may not have been previously or be currently diagnosed with infection by a pathogenic *V. parahaemolyticus* bacteria, but may be considered at risk of having the infection, for example, a subject who may be free of symptoms, but who may have been exposed to, or be considered to be at risk of having been exposed to a pathogenic *V. parahaemolyticus* bacterium.

Similarly, a substrate may be suspected of having contamination with a pathogenic *V. parahaemolyticus* bacterium and methods of the invention can be used to measure the pathogenic *V. parahaemolyticus* in a biological sample from the substrate, thus the substrate may be determined to be contaminated with the pathogenic *V. parahaemolyticus* bacteria. In some embodiments, a substrate may not have been previously, or be currently identified as being contaminated with the pathogenic *V. parahaemolyticus*, but may be considered to be at risk of contamination by a pathogenic *V. parahaemolyticus* bacterium. In some embodiments of the invention, a substrate may have previously identified as having contamination by a pathogenic *V. parahaemolyticus* bacteria, but conditions such as temperature or environmental status may have changed and methods of the invention may be used to identify an increase, or decrease in contamination of the substrate.

In some embodiments of the invention, a sample comprises a cell or tissue or extracellular material from a subject or substrate. In some embodiments a sample comprises one or more of: a skin sample, fluid sample, tissue sample, stool sample, mucus sample, sweat sample, tear sample, urine sample, pus sample, tissue scraping, gastric sample, emesis sample, inflammatory exudate sample, blood sample, or lymph sample. It will be understood that additional types of samples may also be used in methods of the invention. In certain embodiments of the invention, a sample is a cultured sample.

In certain embodiments of the invention a sample is a sample obtained from a substrate. In some embodiments of the invention, a substrate comprises a liquid. A liquid component of a sample may, in some embodiments comprise water. In some embodiments of the invention a substrate is at least a portion of a tool, work surface, a medical device, body of water, clothing, skin, tissue, an edible substance (e.g., a beverage or food), etc. In certain embodiments, a substrate may comprise a solid, such as, but not limited to: metal, wood, dirt, rock, plastic, glass, cork, fiber, a polymer, stone, leather, plant matter, fiberglass, nylon, or a fabric. In some embodiments of the invention a substrate may comprise a food or beverage substance. Non-limiting examples of food substances that may be assessed using methods of the invention include shellfish, fish, water organisms, plants, dairy products, etc. In certain embodiments, a sample may be obtained from one or more of a plurality of substrates, for example from one or more individual shellfish that make up part of a plurality of shellfish, and results of an detection method of the invention may be used to identify whether or not the plurality of substrates is contaminated with a pathogenic *V. parahaemolyticus* bacteria.

As used herein, the term "isolated", when used in the context of a sample, is intended to indicate that the sample has been removed from a subject, culture, or substrate. In some embodiments of the invention, a sample is isolated from a subject, culture, or substrate and is subjected to a method of the present invention without further processing or manipulation subsequent to its isolation. In some embodiments of the invention, a sample can be processed or manipulated subsequent to being isolated and prior to being subjected to a method of the invention. For example, a sample can be refrigerated (e.g., stored at 4° C.), frozen (e.g., stored at −20° C., stored at −135° C., frozen in liquid nitrogen, or cryopreserved using any one of many standard cryopreservation techniques known in the art). Furthermore, a sample may be purified subsequent to isolation from a subject, culture, or a substrate and prior to subjecting it to a method of the present invention.

As used herein, the term "purified" when used in the context of a sample, is intended to indicate that at least one component of the isolated biological sample has been removed from the sample such that fewer components, and consequently, purer components, remain following purification. For example, a serum sample can be separated into one or more components using centrifugation techniques known in the art to obtain partially-purified sample preparation. Furthermore, it is possible to purify a biological sample such that substantially only one component remains. For example, a sample can be purified such that substantially only the polypeptide or polynucleotide component of the sample remains. Thus it will be understood that a sample may originally comprise one or more of a pathogenic *V. parahaemolyticus* bacterium may be purified and processed prior to assay and thus may no longer contain the *V. parahaemolyticus* bacteria, but containing components of the pathogenic *V. parahaemolyticus* bacteria such as one or more pathogenic *V. parahaemolyticus* bacteria polynucleotides (also referred to herein as pathogenic *V. parahaemolyticus* polynucleotides). Therefore, identifying a status of a pathogenic *V. parahaemolyticus* polynucleotide in a sample that has been isolated or processed identifies that status in the original sample.

Furthermore, it may be desirable to amplify a component of a sample such that detection of the component is facilitated. For example, the mRNA component of a biological sample can be amplified (e.g., by RT-PCR) such that detection of *V. parahaemolyticus* mRNA is facilitated. As used herein, the term "RT-PCR" (an abbreviation for reverse transcriptase-polymerase chain reaction) involves subjecting mRNA to the reverse transcriptase enzyme, resulting in the production of a cDNA which is complementary to the base sequences of the mRNA. Large amounts of selected cDNA can then be produced by means of the polymerase chain reaction which relies on the action of heat-stable DNA polymerase for its amplification action. Alternative amplification methods include: self-sustained sequence replication (Guatelli, J. C. et al., 1990, Proc. Natl. Acad. Sci. USA 87: 1874-1878), transcriptional amplification system (Kwoh, D. Y. et al., 1989, Proc. Natl. Acad. Sci. USA 86: 1173-1177), Q-Beta Replicase (Lizardi, P. M. et all, 1988, Bio/Technology 6: 1197), or any other nucleic acid amplification method, followed by the detection of the amplified molecules using techniques well known to those of skill in the art. These detection schemes are especially useful for the detection of nucleic acid molecules if such molecules are present in very low numbers.

*V. parahaemolyticus* Detection Techniques

*V. parahaemolyticus* molecules (for example, *V. parahaemolyticus* polypeptides and polynucleotides that encode *V. parahaemolyticus* polypeptides), can be detected and measured using any suitable means known in the art. In certain aspects of the invention a *V. parahaemolyticus* polypeptide and/or polynucleotide that encodes a *V. parahaemolyticus* polypeptide are molecules that are present in pathogenic *V. parahaemolyticus* bacteria, and are not present in non-pathogenic bacteria. Thus, in certain embodiments the polypeptide molecules and nucleic acid molecules that encode the polypeptides are signature molecules. In some embodiments of the invention, a detection or measurement means for *V. parahaemolyticus* molecules includes an immunological assay, nucleotide determination (mRNA or DNA), etc. Examples of immunological assays suitable for use in methods of the invention may include, but are not limited to ELISA assays, assays that utilize an anti-*V. parahaemolyticus* polypeptide antibody (or FV derivative) to which is conjugated a detectable label. A detectable label may be conjugated (also referred to herein as "linked") either directly or indirectly. In some aspects of the invention, pathogenic *V. parahaemolyticus* presence and/or levels may be measured by a PCR reaction, in situ hybridization, DNA microarray hybridization, or other suitable method to identify the presence of a sequence present in a pathogenic *V. parahaemolyticus* bacterium. Methods of measuring levels of polynucleotides encoding pathogenic *V. parahaemolyticus* bacteria (i.e. pathogenic *V. parahaemolyticus* bacteria mRNA) may include, but are not limited to, real-time polymerase chain reaction (qRT-PCR), DNA array, and next generation sequencing methods. Application and optimization of such methods are known and practiced in the art.

The present invention features agents that are capable of detecting and/or quantitating a pathogenic *V. parahaemolyticus* bacteria-encoding polynucleotide such that the presence and/or level of the pathogenic *V. parahaemolyticus* bacteria are determined. As defined herein, an "agent" refers to a substance that is capable of identifying or detecting a pathogenic *V. parahaemolyticus* bacteria in a sample (e.g., identifies or detects pathogenic *V. parahaemolyticus* bacteria mRNA, DNA, polypeptide, activity, etc.). As used herein, the terms "labeled" or "labelable" refers to the attaching or including of a label (e.g., a marker or indicator) or ability to attach or include a label (e.g., a marker or indicator). A detectable label may be conjugated to (also referred to herein as "linked to") a polynucleotide either directly or indirectly. For example, though not intended to be limiting: a direct link may be a be when a detectable label and a polynucleotide are physically attached to each other, and an indirect link may be when a detectable label is physically attached to an entity and the entity and not the detectable label is physically attached to a polynucleotide. Detectable labels, markers, or indicators useful in methods of the invention may include, but are not limited to, for example, radioactive molecules, colorimetric molecules, and enzymatic molecules that produce detectable changes in a substrate. A detectable label for use in methods, compositions, and kits of the invention may be a radioactive molecule, a luminescent molecule, a fluorescent molecule, a chemiluminescent molecule, biotin, an enzyme, a His tag, or an exogenous nucleic acid sequence, or other suitable detectable label known in the art. In some aspects of the invention, a detectable label comprises: Hexachloro-Fluorescein (HEX), VIC fluorescent dye, 4-5-Dichloro carboxy fluorescein (JOE), Cy3 fluorescent dye, or TexasRed (TxRed).

Methods of the invention for detecting the presence and/or quantity of a pathogenic *V. parahaemolyticus* bacterium may also include procedures such as an immunological assay, a polymerase chain reaction, real-time polymerase chain reaction (qRT-PCR), mass spectroscopy, etc. In addition, embodiments of the invention include may include nucleic "aptamers", i.e. nucleic acids [DNA, RNA or peptide nucleic acids (PNAs)] that possess high affinity for polypeptides now identified as present in pathogenic *V. parahaemolyticus* bacteria (which may not be present in non-pathogenic *V. parahaemolyticus* bacteria) and can be readily labeled for high throughput binding assays. Aptamers can be produced by standard molecular biological techniques by those skilled in the art by repeated rounds of binding, selection, and affinity, and amplification [Hamaguchi, et al. Anal. Biochem. (2001) 294; pt 2, pages 126-131].

In some embodiments of the invention an agent is a labeled or labelable polynucleotide probe capable of hybridizing to a pathogenic *V. parahaemolyticus* polynucleotide, (e.g., a pathogenic *V. parahaemolyticus* RNA or DNA). For example, the agent can be an oligonucleotide primer for the polymerase chain reaction that flanks or lies within the nucleotide sequence encoding pathogenic *V. parahaemolyticus* polypeptides that may be present in pathogenic *V. parahaemolyticus* and may not be present in non-pathogenic *V. parahaemolyticus* bacteria. In some embodiments of the invention, the biological sample being tested is an isolate, for example, RNA. In yet another embodiment, the isolate (e.g., the RNA) is subjected to an amplification process that results in amplification of a pathogenic *V. parahaemolyticus* polynucleotide. As defined herein, an "amplification process" is designed to strengthen, increase, or augment a molecule within the isolate. For example, where the isolate is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Pathogenic *V. parahaemolyticus* Nucleic Acid Binding Agents

Types of agents that can be used to determine levels of pathogenic *V. parahaemolyticus*-encoding polynucleotides may include, but are not limited to cDNA, riboprobes, synthetic oligonucleotides, and genomic probes. Probes of the invention may also be used in real-time PCR (also referred to as qPCR) methods. It will be understood that primers listed herein are also probes in the sense that they bind, hybridize, anneal to a sequence. The type of agent (e.g. probe) used will generally be dictated by the particular situation, such as riboprobes for in situ hybridization, and cDNA for Northern blotting, for example. In certain aspects of the invention, the probe is directed to nucleotide regions unique to the polypeptide. Detection of the pathogenic *V. parahaemolyticus*-encoding gene, per se, will be useful for diagnostic methods of the invention and for screening for compounds to treat infection and/or contamination by the pathogenic *V. parahaemolyticus* bacteria. Other forms of assays to detect targets more readily associated with levels of expression—transcripts and other expression products—will generally be useful as well. A probe may be as short as is required to differentially recognize pathogenic *V. parahaemolyticus* mRNA transcripts, and may be as short as, for example, 6, 7, 8, 9, 10, 11, 12, 13, 14, 15, 16, 17, 18, 19, 20, 21, 22, 23, 24, 25, 26, 27, 28, 29, 30 bases, or more may be used. Non-limiting examples of polynucleotides that may be considered probes in certain instances are set forth herein as: SEQ ID NOs:2, 3, 4, 5, 6, 7, 9, 10, 12, 13, 14, 16, 17, 19, 20, 21, 22, 23, 24, 25, 26, 27, 28, 29, 30, 31, 32, 33, 34, 35, 36, 37, 39, 40, and polynucleotides identified as primers and probes in Tables 2 and 3. One or more probes may also be reverse engineered by one skilled in the art, for example using the nucleic acid sequence of a pathogenic *V. parahaemolyticus* provided herein, such as SEQ ID NO:1, SEQ ID NO:8, SEQ ID NO:38 or other provided sequence or variant thereof. The form of labeling of a probe used in an embodiment of the invention may be any that is appropriate, such as the use of radioisotopes, for example, $^{32}P$ and $^{35}S$, etc. Labeling with radioisotopes may be achieved, whether the probe is synthesized chemically or biologically, by the use of suitably labeled bases using methods well known in the art. For use in some aspects of the invention, probes may be detectably labeled with a fluorescent (also referred to herein as a chemiluminescent or luminescent) molecule, examples of which include, but are not limited to: Hexachloro-Fluorescein (HEX), VIC fluorescent dye, 4-5-Dichloro carboxy fluorescein (JOE), Cy3 fluorescent dye, and TexasRed (TxRed). Additional types of detectable labels, known in the art and/or disclosed herein may also be used in conjunction with polynucleotide probes of the invention. In some embodiments of the invention a *V. parahaemolyticus* molecule may be detected as part of a complex with one or more additional molecules such as polynucleotides or labeling agents.

Pathogenic *V. parahaemolyticus* RNA Detection Techniques

Detection of RNA transcripts may be achieved by Northern blotting, for example, wherein a preparation of RNA is run on a denaturing agarose gel, and transferred to a suitable support, such as activated cellulose, nitrocellulose or glass or nylon membranes. Radiolabeled cDNA or RNA is then hybridized to the preparation, washed and analyzed by autoradiography.

Detection of RNA transcripts can further be accomplished using known amplification methods. For example, it is within the scope of the present invention to reverse transcribe mRNA into cDNA followed by real-time polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR). Each of these methods is well known and routinely used in the art. Other known amplification methods can also be utilized in methods of the invention. In situ hybridization visualization may also be employed, wherein a radioactively labeled antisense RNA probe is hybridized with a thin section of a biopsy sample, washed, cleaved with RNase and exposed to a sensitive emulsion for autoradiography. Biological samples may be stained with haematoxylin to demonstrate the histological composition of the sample, and dark field imaging with a suitable light filter shows the developed emulsion. Non-radioactive labels such as digoxigenin, or others referred to herein and/or known in the art may also be used.

Pathogenic *V. parahaemolyticus* Antibodies and Additional Binding Agents

In addition to using PCR and RNA detection methods for detection of a pathogenic *V. parahaemolyticus* molecule in diagnostic methods of the invention, it may also be possible to use other molecules or compounds that bind to a pathogenic *V. parahaemolyticus* molecule identified as being expressed in pathogenic but not non-pathogenic *V. parahaemolyticus* bacteria. For example, it may be possible to identify compounds, and/or molecules such as polypeptides that specifically bind to a pathogenic *V. parahaemolyticus* molecule. In addition, it may also be possible to use an antibody or other compound or molecule that binds to, and permits detection of a pathogenic *V. parahaemolyticus* molecule in a sample. In some embodiments a pathogenic *V.*

*parahaemolyticus* molecule may be detected as part of a complex with one or more additional polypeptides.

An isolated pathogenic *V. parahaemolyticus* polypeptide, or fragment thereof, can be used as an immunogen to generate antibodies that bind pathogenic *V. parahaemolyticus* polypeptides using standard techniques for polyclonal and monoclonal antibody preparation. The full-length pathogenic *V. parahaemolyticus* polypeptide can be used or, alternatively, the invention provides antigenic peptide fragments of a pathogenic *V. parahaemolyticus* for use as immunogens. The antigenic peptide of pathogenic *V. parahaemolyticus* may comprise at least 8 amino acid residues of the amino acid sequence set forth herein and encompasses an epitope of a polypeptide from a pathogenic *V. parahaemolyticus* that is not present in a non-pathogenic *V. parahaemolyticus* polypeptide.

Pathogenic *V. parahaemolyticus* Protein Detection Techniques

In certain embodiments of the invention, methods include the use of diagnostic molecules (e.g., antibodies, antibody equivalents, binding molecules, etc.) to detect pathogenic *V. parahaemolyticus* polypeptides. Amino acid sequences of pathogenic *V. parahaemolyticus* polypeptides prp, cps, and flp are provided herein as SEQ ID NOs: 41, 42, and 46, respectively. Methods for the detection of polypeptides are well known to those skilled in the art, and include ELISA (enzyme linked immunosorbent assay), RIA (radioimmunoassay), Western blotting, and immunohistochemistry. Methods for immunoassays are routinely used and are well known in the art.

ELISA and RIA procedures may be conducted such that a pathogenic *V. parahaemolyticus* standard is labeled (with a radioisotope such as $^{125}$I or $^{35}$S, or an assayable enzyme, such as horseradish peroxidase or alkaline phosphatase), and, together with the unlabelled sample, brought into contact with the corresponding antibody, whereon a second antibody is used to bind the first, and radioactivity or the immobilized enzyme assayed (competitive assay). Alternatively, pathogenic *V. parahaemolyticus* in the sample is allowed to react with the corresponding immobilized antibody, radioisotope- or enzyme-labeled anti-pathogenic *V. parahaemolyticus* antibody is allowed to react with the system, and radioactivity or the enzyme assayed (ELISA-sandwich assay). Other conventional methods may also be employed as suitable. Enzymatic and radiolabeling of a detection agent (e.g., antibodies, binding molecules, etc.) may be carried out by conventional means.

Other techniques may be used to detect pathogenic *V. parahaemolyticus* molecules according to a practitioner's preference based upon the present disclosure. One such technique is Western blotting (Towbin et al., 1979 Proc. Nat. Acad. Sci. 76:4350), wherein a suitably treated sample is run on an SDS-PAGE gel before being transferred to a solid support, such as a nitrocellulose filter. Anti-pathogenic *V. parahaemolyticus* antibodies (unlabeled) are then brought into contact with the support and assayed by a secondary immunological reagent, such as labeled protein A or anti-immunoglobulin (suitable labels including but not limited to $^{125}$I, horseradish peroxidase and alkaline phosphatase). Chromatographic detection may also be used.

Immunohistochemistry may be used to detect expression of pathogenic *V. parahaemolyticus* in a biological sample. A suitable antibody is brought into contact with, for example, cells, washed, and then contacted with a second, labeled antibody. Labeling may be by fluorescent markers, enzymes, such as peroxidase, avidin, or radiolabelling. The assay may be scored visually, using microscopy, or using any other suitable methods.

Pathogenic *V. parahaemolyticus* Detection Kit

The invention also encompasses kits for detecting the presence of pathogenic *V. parahaemolyticus* in a sample (e.g., a cell sample, tissue sample, water sample, seafood sample, fish sample, wound sample, etc.). For example, a kit can comprise a labeled or labelable agent capable of detecting a pathogenic *V. parahaemolyticus* polypeptide or polynucleotide (e.g., RNA, DNA, etc.) in a sample and a means for determining a status (e.g., at least one of the presence and level/amount) of a pathogenic *V. parahaemolyticus* molecule in the sample. The agent can be packaged in a suitable container. The kit can further comprise a means for comparing the level of the pathogenic *V. parahaemolyticus* molecule in the sample with a standard or control and/or can further comprise instructions for using the kit to detect the pathogenic *V. parahaemolyticus* polynucleotide or polypeptide. A kit may also include a detectably labeled probe.

This invention in some aspects also provides a kit for measuring pathogenic *V. parahaemolyticus* molecules. Such a kit may include a diagnostic agent (e.g., an antibody or antibody fragments, or binding molecule, etc.) that selectively bind a pathogenic *V. parahaemolyticus* molecule or a set of DNA oligonucleotide primers that allows synthesis of cDNA encoding the polypeptide or a DNA probe that detects expression of a pathogenic *V. parahaemolyticus* mRNA, etc. In some embodiments of the invention, the primers and probes may comprise at least 8, 9, 10, 11, 12, 13, 14, 15, 16, 17, 18, 19, 20, 21, 22, 23, 24, or more nucleotides and hybridize under stringent conditions to a DNA fragment having the nucleic acid sequence set forth herein, for example, the nucleic acid sequence of an ST36prp polynucleotide, a ST36cps polynucleotide, a tlh polynucleotide, a tdh polynucleotide, a trh polynucleotide, an ST36flp polynucleotide, an ST631end polynucleotide, ST631-ENV polynucleotide, ST34lys polynucleotide, an ST34reg polynucleotide, an ST1127hyp polynucleotide, an ST36Phage or other polynucleotide set forth in Table 2, Table 3, or elsewhere herein, or a variant thereof. As herein used, the term "stringent conditions" means hybridization will occur only if there is at least 85%, 90%, 91%, 92%, 93%, 94%, 95%, 96%, 97%, 98%, or at least 99%, identity between the sequences. Table 1 provides additional information in reference to the prp, cps, flp, tdh, trh, and tlh sequences and FIG. 8 provides additional information in reference to loci such as the ST631, ST34, ST674, ST1127, and ST36 loci. Table 2 provides non-limiting examples of primers utilized in PCR amplifications. Table 3 provides oligonucleotide primers, which in some aspects of the invention may be used in qPCR detection. QPCR is also referred to as real-time PCR.

TABLE 1

Sequence Identification Information for prp, cps, flp, tdh, trh, and tlh

| | Protein accession # | contig accession # | location in contig | locus tag |
|---|---|---|---|---|
| flp | EGF42675 | AFBW01000018.1 | 220810 . . . 222099 | VP10329_01545 |
| tdh | EGF40527 | AFBW01000025.1 | 7483 . . . 8007 | VP10329_22563 |
| trh | EGF40542 | AFBW01000025.1 | 22125 . . . 22694 | VP10329_22638 |

TABLE 1-continued

Sequence Identification Information for prp, cps, flp, tdh, trh, and tlh

| | Protein accession # | contig accession # | location in contig | locus tag |
|---|---|---|---|---|
| tlh | EGF40542 | AFBW01000024.1 | 230297 . . . 231550 | VP10329_04677 |
| prp | EGF42613 | AFBW01000018.1 | 160407 . . . 162398 | VP10329_01235 |
| cps | EGF42671 | AFBW01000018.1 | 216766 . . . 218355 | VP10329_01525 |

TABLE 2

Oligonucleotide primers used for isolate identification by PCR and examples of amplification conditions

| Gene/locus | Primer sequence | SEQ ID NO | Amplicon size (bp) | Temp Anneal | Source |
|---|---|---|---|---|---|
| Tlh | F2: AGAACTTCATCTTGATGACACTGC | 12 | 401 | 55 | 1 |
| | F: AAAGCGGATTATGCAGAAGCACTG | 13 | 450 | | 2 |
| | R: GCTACTTTCTAGCATTTTCTCTGC | 14 | | | |
| Tdh | F: GTAAAGGTCTCTGACTTTTGGAC | 16 | 269 | 55 | 1 |
| | R: TGGAATAGAACCTTCATCTTCACC | 17 | | | |
| Trh | F: CATAACAAACATATGCCCATTTCCG | 19 | 500 | 55 | 1 |
| | R: TTGGCTTCGATATTTTCAGTATCT | 20 | | | |
| ORF8 | F-O3MM824: AGGACGCAGTTACGCTTGATG | 47 | 369 | 55 | 1 |
| | R-O3MM1192: CTAACGCATTGTCCCTTTGTAG | 48 | | | |
| ST36prp | F: CGGCTTGAGTTTTCGTCATT | 2 | 609 | 55 | 2 |
| | R: CCACACCTGCTGGTTATTTAGTTC | 3 | | | |
| ST36prp | F2: TGCGGAATCTGATCTTTATCCTC | 6 | 1028 | 55 | 2 |
| | R2: AACTGTTGGGTCTTCGTCTAACC | 7 | | | |
| ST36prp | F3: CCCGAGGCACATCTTCACC | 4 | 699 | 55 | 2 |
| | R3: TAAACCACTAACATCTTCATCTACC | 5 | | | |
| ST36cps | F1: TTGAGAATTACTTCCGATTATGTAGA | 9 | 889 | 55 | 2 |
| | R1: TAAACGCATTAGCGAATAGTGC | 10 | | | |
| ST36flp | F1: TGGTTGTGTTTAGAGCAGGG | 36 | 747 | 55 | 2 |
| | R1: TGTTGGTAATACGATAAGAATGAGA | 37 | | | |
| ST631end | F1: AGTTCATCAGGTAGAGAGTTAGAGGA | 53 | 494 (1.5 min) | 57 | 3 |
| | R1: TCTTCGTTACCATAGTATGAGCCA | 54 | | | |
| ST631-ENV | F1: TGGGCGTTAGGCTTTGC | 59 | 496 (1.5 min) | 57 | 3 |
| | F2: GGGCTTCTACGACTTTCTGCT | 60 | | | |
| ST34reg | F1: TCCTTGTTGTCGTTGAATATCAGTC | 63 | 592 (1.5 min) | 60 | 3 |
| | R1: GATACGGTTGTCATGCCTATGTGT | 64 | | | |
| ST674hyp | F1: GAAGATGGTCCAAGAGGGAAGC | 69 | 449 (1.5 min) | 56 | 3 |
| | R1: CTATCAGAGATTGAGCAAGTAGC | 70 | | | |
| ST1127hyp | F1: CGTAAAGTAAAAGAGCCTGGTC | 75 | 1234 (1.5 min) | 56 | 3 |
| | R1: TTCAGTTCCCCGCATTCAT | 76 | | | |
| ST36Phage | F2: AGCAACGAAAACGCCTGT | 81 | 1000 (1.5 min) | 55 | 3 |
| | R2: ACCGTATCACCAATGGACTGT | 82 | | | |
| ST36NEOrf10-Hyp | F: TTTCTTACTTCTGTGAGCATTTGA | 87 | 618 (1.5 min) | 55 | 3 |
| | R: GATTACTGAGCCTCTAAAGCCGTC | 88 | | | |
| ST36PhHypD-Orf9 | F3: AAGTGCTACATGAATGAAAGTGCT | 94 | 854 (MA-36) | 55 | 3 |
| | R1: TCAATGAAGTATCACGAAATGACTA | 95 | 1440 (MA-26) | | |
| TdhUreG | fwd4: GAATGCTGCCAACATGGATATAAAT | 100 | 2638 (3 min) | 55 | 3 |
| | rev5: GACAAAGGTATGCTGCCAAAAGTG | 101 | | | |

Sources: (1) Panicker etal., (2004) Appl Environ Microbiol. Dec; 70(12): 7436-7444; (2) Whistler et al. 2015 1 Clin. Microbiol. June 2015 vol. 53 no. 6 1864-1872; (3) unpublished

TABLE 3

Oligonucleotide primers, examples of labels, and Tm conditions.

| Locus | Primer sequence | SEQ ID NO | Modification | Tm | Source |
|---|---|---|---|---|---|
| Tlh | F: ACTCAACACAAGAAGAGATCGACAA | 104 | | 61 | (1) |
| | R: GATGAGCGGTTGATGTCCAA | 105 | | 63 | |
| | Probe: CGCTCGCGTTCACGAAACCGT | 106 | 5' TxRED to 3' BHQ2 | 72 | |
| tdh | F: TCCCTTTTCCTGCCCCC | 110 | | 63 | (1) |
| | R: CGCTGCCATTGTATAGTCTTTATC | 111 | | 61 | |
| | Probe: TGACATCCTACATGACTGTG | 112 | 5' FAM to 3' MGBNFQ | 47 | |
| trh | F: TTGCTTTCAGTTTGCTATTGGCT | 116 | | 64 | (1) |
| | R: TGTTTACCGTCATATAGGCGCTT | 117 | | 64 | |
| | Probe: AGAAATACAACAATCAAAACTGA | 118 | 5' TET to 3' MGBNFQ | 55 | |
| prp* | F1: TGACGCAGCTTTAGGGACTAACTTA[1] | 122 | | 64 | (2) |
| 242 bp | R1: CGCTAAACCACTAACATCTTCATCTAC | 123 | | 65 | |
| | F2: GCGAGGAGGGTTATTCTGACTTAG | 124 | | 64 | |
| | R2: CTAAGTCAGAATAACCCTCCTCGC[1] | 125 | | 64 | |
| | R3: AAATCTATGAATTTGTAGAAGTGGTGTG | 126 | | 63 | |
| | Probe1: ATACCTGTCAGTCGTCGAAATTGGTGGAG[1] | 127 | 5' Cy3 to 3' BHQ2 | 74 | |
| | Probe2: ATACCTGTCAGTCGTCGAAATTGGTGGA | 128 | 5' TxRED to 3' BHQ2 | 73 | |
| | Probe3: ATACCTGTCAGTCGTCGAAATTGGTGGA | 129 | 5' VIC to 3'BHQ1 | 73 | |
| | Probe4: CAACATCATGCCGCTGTAATGGTGAG | 130 | 5' Cy3 to 3' BHQ2 | 72 | |
| flP | F: AATCTGTTCTGGTTGTGTTTAGAGC | 140 | | 62 | (2) |
| 143 bp | R: AAAGGTCCCAAAGCTGTCAATATAG | 141 | | 62 | |
| 211 bp | R2: AAGTCTTTTCATCACCTTCATTGC | 142 | | 62 | |
| | Probe: CTAGGGGTTGAACAGTTTGGATCTTTTAGTTTA | 143 | 5' FAM to 3' BHQ1 | 73 | |
| | Probe2: CTAGGGGTTGAACAGTTTGGA | 144 | 5' FAM to 3' MGBNFQ | 60 | |
| end | F: GCTGAGAGGTTGGAAAGTGTAGC | 151 | | 62 | (2) |
| 162 bp | R: TCTTCGTTACCATAGTATGAGCCA | 152 | | 62 | |
| | F2: TATCGGTGGGATTTCTGGTGT | 153 | | 59 | |
| | R2: CATTAACCAAGGAGTAGGAGGAAGT | 154 | | 60 | |
| | Probe: GGGTGATCATGGAGCATAGTGAAGGTAAA | 155 | 5' TxRED to 3' BHQ2 | 72 | |
| | Probe2: TCTCAAGCAGGGTATCAATCAGGCG | 156 | 5' TxRED to 3' BHQ2 | 72 | |
| 631- | F TGATAGTCGTGGTTGCGTGC | 170 | | 63 | (2) |
| ENV | R AGCTGAATCGGTTTGGTTACA | 171 | | 62 | |
| | Probe: TTGGGCGTTAGGCTTTGCGTACA | 172 | TBD | 72 | |
| IAC | F: GACATCGATATGGGTGCCG | 164 | | 62 | (1) |
| | R: CGAGACGATGCAGCCATTC | 165 | 5' Cy5 to 3' BHQ2 | 62 | |
| | Probe: TCTCATGCGTCTCCCTGGTGAATGTG | 166 | | 74 | |

*HEX, VIC, or JOE would be substituted for Cy3 if using Agilent device instead of Cephid Smartcycler, and TxRed if prp is combined with tdh and trh. prpF1/R1 have 330 bp amplicon, and [1]prpF1 and prpR2 give 242 bp amplicon- use with probe 1 on smartcycer. Primer R3 will give-100 bp band. Can us prpF2/R1 for SYBR assay. F1 and R3. Sources: (1) Nordstrom, et al., (2007) Appl Environ Microbiol. Sep;73(18):5840-7. Epub 2007 Jul 20 and (2) Unpublished.

Methods of Detection

The invention in some aspects provides methods for detecting the presence of a pathogenic *V. parahaemolyticus* molecule in a sample. The method may comprise contacting the sample with an agent capable of detecting pathogenic *V. parahaemolyticus* polypeptide or polynucleotide molecules (e.g., pathogenic *V. parahaemolyticus* RNA, cDNA, mRNA, or DNA, etc.) such that the presence of pathogenic *V. parahaemolyticus* is detected in the sample. An agent for detecting pathogenic *V. parahaemolyticus* polynucleotide using methods of the invention may be a labeled or labelable nucleic acid probe capable of hybridizing to *V. parahaemolyticus* mRNA. The nucleic acid probe may be, for example, the full-length *V. parahaemolyticus* sequences set forth herein, including but not limited to: SEQ ID NO:1 (prp locus), SEQ ID NO:8 (cps locus), SEQ ID No. 11 (tlh locus), SEQ ID NO:15, (tdh locus), SEQ ID NO:18 (trh locus) and SEQ ID NO:38 (flp locus), or a portion thereof, such as an oligonucleotide of at least 3, 4, 5, 10, 15, 30, 50, 100 or more nucleotides in length and sufficient to specifically hybridize under stringent conditions to pathogenic *V. parahaemolyticus* mRNA. Polypeptides that may be detected using methods of the invention, and whose presence may indicate the presence of a pathogenic *V. parahaemolyticus* bacteria include, but are not limited to the polypeptides set forth herein as SEQ ID NO:41, 42, and 46. Polynucleotides that may be used as probes in certain embodiments of methods and kits of the invention include, but are not limited to primers and probes set forth in Tables 2 and 3.

The term "labeled or labelable", with regard to the probe or antibody, is intended to encompass direct labeling of the probe or antibody by coupling (i.e., physically linking) a detectable substance to the diagnostic molecule (e.g., probe, antibody, binding molecule, etc.), as well as indirect labeling of the molecule by reactivity with another reagent that is directly labeled. Some non-limiting examples of indirect labeling include detection of a primary antibody using a fluorescently labeled secondary antibody and end-labeling of a DNA probe with a fluorescent molecule, with biotin such that it can be detected with fluorescently labeled streptavidin, or other detectable label.

Detection methods useful in certain embodiments of methods of the invention, including but not limited to those described above herein, can be used as the basis for a method of detecting the presence or absence of a pathogenic *V. parahaemolyticus* molecule, can be used as the basis for a method of monitoring the progression of an infection or contamination by the pathogenic *V. parahaemolyticus* bacterium in a subject or substrate, or can be used as the basis for a method of determining a prognosis for a subject at risk for infection with or a subject or substrate at risk for contamination by a pathogenic *V. parahaemolyticus* bacterium.

Some aspects of the invention provide a prognostic method for determining whether a subject is at risk for developing an infection by pathogenic *V. parahaemolyticus* bacteria, or whether a substrate of subject is at risk for contamination by a pathogenic *V. parahaemolyticus* bacterium. Such methods may include contacting a sample obtained from the subject or substrate (or isolate of the sample) with an agent capable of detecting a pathogenic *V. parahaemolyticus* polypeptide or polynucleotide such that the presence and/or level of the pathogenic *V. parahaemolyticus* polypeptide or polynucleotide is detected in the sample or isolate, thereby determining whether the subject or substrate has an infection and/or contamination and/or is at risk for developing an infection or contamination by the pathogenic *V. parahaemolyticus* bacterium.

In some aspects and embodiments, diagnostic methods of the present invention may include determining the level of a pathogenic *V. parahaemolyticus* polynucleotide in a sample or isolate from a sample. In certain embodiments, methods of the present invention may include comparing the level of a pathogenic *V. parahaemolyticus* polypeptide or polynucleotide in a sample or isolate with the level of the pathogenic *V. parahaemolyticus* polypeptide or polynucleotide in a control sample. In yet another embodiment, a diagnostic or prognostic method of the invention may also include a step of forming a prognosis or forming a diagnosis, and may also include a step of determining an appropriate treatment for a subject or substrate by a health-care provider, environmental scientist, scientist, public health personnel, or other appropriate party, based at least in part on the determination of the presence, absence, and/or amount of the pathogenic *V. parahaemolyticus* molecule in a sample from the subject or substrate.

In certain aspects of the invention, determining the presence and/or amount of a pathogenic *V. parahaemolyticus* molecule can be carried out in conjunction with the determination of one or more other biomarkers of the pathogenic *V. parahaemolyticus* bacteria. For example, the level and/or presence of a pathogenic *V. parahaemolyticus* molecule (e.g., a polynucleotide that encodes a pathogenic *V. parahaemolyticus* polypeptide, a pathogenic *V. parahaemolyticus* polypeptide or signature fragment thereof), may be detected using a panel that also permits detection at least one additional molecule whose expression and/or level is may be useful to characterize an infection or contamination with the pathogenic *V. parahaemolyticus* bacteria. For example, a panel of the invention may comprise a means to determine at least one of the level or presence one of more of a prp locus, a cps locus, and an ftp locus, etc. to generate an aggregate biomarker panel. In certain embodiments, a panel of the invention may comprise a means to determine at least one of the level or presence one of more of a prp locus, a cps locus, a tlh locus, a tdh locus, a trh locus, and an ftp locus, etc. to generate a biomarker panel that may be used in certain embodiments of the invention. A biomarker panel of the invention may include detection means for at least 1, 2, 3, 4, 5, 6, 7, 8, 9, 10, 11, 12, 13, 14, 15, 20, 30, 50, 100 or more biomarkers (including each integer in between the listed integers) in addition to a detection means for a pathogenic *V. parahaemolyticus* bacteria as set forth herein. As used herein, in certain aspects of the invention the term biomarker means a polynucleotide or polypeptide that is specific to a pathogenic *V. parahaemolyticus* bacteria Pathogenic *V. parahaemolyticus* Sequences and Variants One aspect of the invention involves isolated polynucleotide molecules that encode polypeptides of pathogenic *V. parahaemolyticus* bacteria or biologically active portions thereof, as well as polynucleotide fragments sufficient for use as hybridization probes to identify a pathogenic *V. parahaemolyticus* bacteria polypeptide-encoding polynucleotide. A polynucleotide or polypeptide of the invention may be a “signature” polynucleotide or polypeptide, which, as used herein means a polynucleotide or polypeptide that is present in a pathogenic *V. parahaemolyticus* bacteria but not present in a non-pathogenic bacterium, including but not limited to a non-pathogenic *parahaemolyticus* bacterium. Thus, the presence of a signature nucleic acid or polypeptide of a pathogenic *V. parahaemolyticus* bacterium in a biological sample indicates the presence of the pathogenic *V. parahaemolyticus* bacterium in the sample. Examples of signature polynucleotide sequences provided herein, though not intended to be limiting are *V. parahaemolyticus* sequences set forth as SEQ ID NO:1 (prp locus), SEQ ID NO:8 (cps locus), and SEQ ID NO:38 (flp locus), or fragments thereof that are sufficiently unique so as to identify the presence of the prp locus, cps locus, or flp locus, respectively. Examples of some of the signature polypeptide sequences provided herein, though not intended to be limiting are *V. parahaemolyticus* sequences set forth as SEQ ID NO:41 (prp locus), SEQ ID NO:42 (cps locus), and SEQ ID NO:46 (flp locus), or fragments thereof that are sufficiently unique so as to identify the presence of the prp locus, cps locus, or flp locus, respectively.

As used herein, the term “polynucleotide” is intended to include DNA molecules (e.g., cDNA or genomic DNA) and RNA molecules (e.g., RNA, mRNA). A polynucleotide may be single-stranded or double-stranded or may be a double-stranded DNA molecule. An “isolated” polynucleotide molecule is free of sequences that naturally flank the polynucleotide (i.e., sequences located at the 5' and 3' ends of the polynucleotide) in the genomic DNA of the organism from which the polynucleotide is derived. The terms: “polynucleotide”, “oligonucleotide”, may be used interchangeably. For example an oligonucleotide primer may also be referred to as a polynucleotide primer, etc. Moreover, an “isolated” polynucleotide such as a cDNA molecule may be free of other cellular material.

In some aspects of the invention, an isolated polynucleotide of the invention comprises the nucleic acid sequence set forth herein as SEQ ID NO:1 (prp locus), SEQ ID NO:8 (cps locus), SEQ ID NO. 11 (tlh locus), SEQ ID NO:15, (tdh locus), SEQ ID NO:18 (trh locus), SEQ ID NO:38 (flp locus), or another sequence set forth in Tables 2 and 3 or elsewhere herein, or a variant and/or fragment thereof. Some nucleic acid sequences provided herein are identified as sequences of polynucleotides found in pathogenic *V. parahaemolyticus* bacteria, for example SEQ ID NOs: 1, 8, and 38. Some nucleic acid sequences provided herein are identified as sequences of polynucleotides found in *V. parahaemolyticus* bacteria that need not be pathogenic, for example SEQ ID NOs:11, 15, and 18. Table 1 provides additional information in reference to the prp, cps, flp, tdh, trh, and tlh sequences.

The invention further encompasses polynucleotide molecules that differ from the sequences for the *V. parahaemo-*

*lyticus* sequences set forth as SEQ ID NO:1 (prp locus), SEQ ID NO:8 (cps locus), SEQ ID No. 11 (tlh locus), SEQ ID NO:15, (tdh locus), SEQ ID NO:18 (trh locus), SEQ ID NO:38 (flp locus) or another sequence set forth in Tables 2 and 3 or elsewhere herein, or a portion thereof, due to degeneracy of the genetic code and thus encode the same *V. parahaemolyticus* polypeptide as that encoded by the sequences set forth as set forth as SEQ ID NO:1 (prp locus), SEQ ID NO:8 (cps locus), SEQ ID No. 11 (tlh locus), SEQ ID NO:15, (tdh locus), SEQ ID NO:18 (trh locus), SEQ ID NO:38 (flp locus), or another sequence set forth in Tables 2 and 3 or elsewhere herein, respectively. Encoded *V. parahaemolyticus* polypeptides include, but are not limited to sequences set forth herein as SEQ ID NOs:41, 42, 43, 44, 45, and 46, and additional amino acid sequences disclosed herein.

A polynucleotide having the nucleic acid sequence as set forth herein as SEQ ID NO:1 (prp locus), SEQ ID NO:8 (cps locus), SEQ ID No. 11 (tlh locus), SEQ ID NO:15, (tdh locus), SEQ ID NO:18 (trh locus), SEQ ID NO:38 (flp locus), or another sequence set forth in Tables 2 and 3 or elsewhere herein, or a portion thereof, can be isolated using standard molecular biology techniques and the sequence information provided herein. For example, a cDNA library can be probed using all or portion of a sequence set forth as SEQ ID NO:1 (prp locus), SEQ ID NO:8 (cps locus), SEQ ID No. 11 (tlh locus), SEQ ID NO:15, (tdh locus), SEQ ID NO:18 (trh locus), SEQ ID NO:38 (flp locus) as a hybridization probe and standard hybridization techniques (e.g., as described in Sambrook, J., Fritsh, E. F., and Maniatis, T. Molecular Cloning: A Laboratory Manual. 2nd. edition, Cold Spring Harbor Laboratory, Cold Spring Harbor, N.Y., 1989).

Moreover, a polynucleotide encompassing all or a portion of a sequence set forth as SEQ ID NO:1 (prp locus), SEQ ID NO:8 (cps locus), SEQ ID No. 11 (tlh locus), SEQ ID NO:15, (tdh locus), SEQ ID NO:18 (trh locus), SEQ ID NO:38 (flp locus) or other polynucleotide sequence disclosed herein including but not limited to a ST36end locus, a ST34reg locus, a ST674hyp locus, a ST1127hyp locus, etc. can be isolated using any suitable method, including as a non-limiting example, use of the polymerase chain reaction using oligonucleotide primers set forth herein and/or designed based upon the sequence set forth herein as SEQ ID NO:1 (prp locus), SEQ ID NO:8 (cps locus), SEQ ID No. 11 (tlh locus), SEQ ID NO:15, (tdh locus), SEQ ID NO:18 (trh locus), SEQ ID NO:38 (flp locus), ST36end locus, ST34reg locus, ST674hyp locus, ST1127hyp locus, etc. can be isolated. For example, *V. parahaemolyticus* mRNA can be isolated from samples using standard, art-known methods and cDNA can be prepared using reverse transcriptase and art-known methods. Synthetic oligonucleotide primers for PCR amplification, such as those provided herein, can be designed based upon one or more nucleic acid sequences set forth herein as SEQ ID NO:1 (prp locus), SEQ ID NO:8 (cps locus), SEQ ID No. 11 (tlh locus), SEQ ID NO:15, (tdh locus), SEQ ID NO:18 (trh locus), SEQ ID NO:38 (flp locus), a ST36end locus, a ST34reg locus, a ST674hyp locus, a ST1127hyp locus, etc. and polynucleotides of the invention can be amplified using cDNA or, alternatively, genomic DNA, as a template and appropriate oligonucleotide primers according to standard PCR amplification techniques. The polynucleotide so amplified can be cloned into an appropriate vector and characterized by DNA sequence analysis. Furthermore, oligonucleotides corresponding to pathogenic and non-pathogenic *V. parahaemolyticus* poly-peptide-encoding nucleic acid sequences can be prepared by standard synthetic techniques, e.g., using an automated DNA synthesizer.

In addition to the pathogenic and non-pathogenic *V. parahaemolyticus* bacterial nucleic acid sequences set forth herein as SEQ ID NO:1 (prp locus), SEQ ID NO:8 (cps locus), SEQ ID No. 11 (tlh locus), SEQ ID NO:15, (tdh locus), SEQ ID NO:18 (trh locus), and SEQ ID NO:38 (flp locus), ST36end locus, ST34reg locus, ST674hyp locus, ST1127hyp locus, etc., it will be appreciated by those skilled in the art that DNA sequence polymorphisms that lead to changes in the amino acid sequences of pathogenic or non-pathogenic *V. parahaemolyticus* may exist within a population (e.g., the bacterial population). Such genetic polymorphism in the *V. parahaemolyticus* gene may exist among bacteria within a population due to natural allelic variation. Such natural allelic variations can typically result in 1-5% variance in the nucleotide sequence of a gene. Any and all such nucleotide variations and resulting amino acid polymorphisms in *V. parahaemolyticus* that are the result of natural allelic variation and that do not alter the pathogenicity of the *V. parahaemolyticus* bacteria are intended to be within the scope of the invention. Polynucleotide molecules corresponding to natural allelic variants of a *V. parahaemolyticus* cDNA of the invention can be isolated based on their homology to the polynucleotides disclosed herein using the cDNA, or a portion thereof, as a hybridization probe—according to standard hybridization techniques under stringent hybridization conditions, which are recognized in the art.

In some aspects of the invention, an isolated polynucleotide of the invention that hybridizes under stringent conditions to a nucleic acid sequence set forth as SEQ ID NO:1 (prp locus), SEQ ID NO:8 (cps locus), SEQ ID No. 11 (tlh locus), SEQ ID NO:15, (tdh locus), SEQ ID NO:18 (trh locus), SEQ ID NO:38 (flp locus), ST36end locus, ST34reg locus, ST674hyp locus, a ST1127hyp locus, or other sequence provided herein, corresponds to a naturally-occurring nucleic acid molecule. As used herein, a "naturally-occurring" nucleic acid molecule refers to an RNA or DNA molecule having a nucleic acid sequence that occurs in nature (e.g., encodes a natural protein). In one embodiment, the nucleic acid encodes a natural *V. parahaemolyticus* polypeptide.

In addition to naturally occurring allelic variants of the *V. parahaemolyticus* sequence that may exist in the bacterial population, the skilled artisan will further appreciate that changes may be introduced by mutation into a nucleic acid sequence set forth as SEQ ID NO:1 (prp locus), SEQ ID NO:8 (cps locus), SEQ ID No. 11 (tlh locus), SEQ ID NO:15, (tdh locus), SEQ ID NO:18 (trh locus), SEQ ID NO:38 (flp locus), ST36end locus, ST34reg locus, ST674hyp locus, ST1127hyp locus, or other sequence provided herein thereby leading to changes in the amino acid sequence of the encoded *V. parahaemolyticus* protein without altering the functional ability of the *V. parahaemolyticus* protein. For example, nucleotide substitutions leading to amino acid substitutions at "non-essential" amino acid residues may be made in the sequences. A "non-essential" amino acid residue is a residue that can be altered from a *V. parahaemolyticus* polypeptide without altering the activity of the *V. parahaemolyticus* polypeptide, whereas an "essential" amino acid residue is required for the *V. parahaemolyticus* polypeptide activity.

The invention, in some embodiments, includes use of full-length sequences of fragments of sequences of polynucleotides that encode pathogenic and non-pathogenic *V.*

*parahaemolyticus* polypeptides, but that differ in sequence from the nucleic acid sequences set forth as SEQ ID NO:1 (prp locus), SEQ ID NO:8 (cps locus), SEQ ID No. 11 (tlh locus), SEQ ID NO:15, (tdh locus), SEQ ID NO:18 (trh locus), SEQ ID NO:38 (flp locus), ST36end locus, ST34reg locus, ST674hyp locus, ST1127hyp locus, or other sequence provided herein and yet can still be used in method of the invention to detect one or more of the presence and level of a pathogenic *V. parahaemolyticus* bacteria in a sample. In certain embodiments of the invention, a variant of a prp polynucleotide, useful in a method of the invention, comprises a nucleic acid sequence that has at least 70%, 75%, 80%, 85%, 90%, 91%, 92%, 93%, 94%, 95%, 96%, 97%, 98%, or 99% identity to the sequence set forth as SEQ ID NO:1 or fragment thereof; a variant of a cps polynucleotide useful in a method of the invention comprises a nucleic acid sequence that has at least 70%, 75%, 80%, 85%, 90%, 91%, 92%, 93%, 94%, 95%, 96%, 97%, 98%, or 99% identity to the sequence set forth as SEQ ID NO:8 or fragment thereof; a variant of a tlh polynucleotide useful in a method of the invention, comprises a nucleic acid sequence that has at least 70%, 75%, 80%, 85%, 90%, 91%, 92%, 93%, 94%, 95%, 96%, 97%, 98%, or 99% identity to the sequence set forth as SEQ ID NO:11 or fragment thereof; a variant of a tdh polynucleotide useful in a method of the invention, comprises a nucleic acid sequence that has at least 70%, 75%, 80%, 85%, 90%, 91%, 92%, 93%, 94%, 95%, 96%, 97%, 98%, or 99% identity to the sequence set forth as SEQ ID NO:15 or fragment thereof; a variant of a trh polynucleotide useful in a method of the invention, comprises a nucleic acid sequence that has at least 70%, 75%, 80%, 85%, 90%, 91%, 92%, 93%, 94%, 95%, 96%, 97%, 98%, or 99% identity to the sequence set forth as SEQ ID NO:18 or fragment thereof; a variant of a flp polynucleotide useful in a method of the invention, comprises a nucleic acid sequence that has at least 70%, 75%, 80%, 85%, 90%, 91%, 92%, 93%, 94%, 95%, 96%, 97%, 98%, or 99% identity to the sequence set forth as SEQ ID NO:38 or fragment thereof; and a variant; or a ST36end locus, ST34reg locus, ST674hyp locus, ST1127hyp locus, or other polynucleotide sequence provided herein that is useful in a method of the invention, comprises a nucleic acid sequence that has at least 70%, 75%, 80%, 85%, 90%, 91%, 92%, 93%, 94%, 95%, 96%, 97%, 98%, or 99% identity to its corresponding polynucleotide sequence of the ST36end locus, ST34reg locus, ST674hyp locus, ST1127hyp locus, or other polynucleotide sequence provided herein, respectively.

It will be understood that a fragment of one or more polynucleotides comprising a nucleic acid sequence set forth herein as SEQ ID NO:1, SEQ ID NO:8, SEQ ID No. 11, SEQ ID NO:15, SEQ ID NO:18, or SEQ ID NO:38 or a polynucleotide sequence of the ST36end locus, ST34reg locus, ST674hyp locus, ST1127hyp locus, or other polynucleotide sequence provided herein can be used in methods of the invention, for example, though not intended to be limiting, as primers or probes. A fragment as used herein may be a portion of a sequence set forth herein, or variant thereof. As used herein, a portion of a polynucleotide having a length of "n" means a polynucleotide having a length of "n" minus at least one, two, three, four, five, or more nucleotides. For example if "n" equals the number of nucleotides in a sequence, a fragment may have a length of "n" minus at least 1, 2, 3, 4, 5, 6, 7, 8, 9, 10, 15, 20, 30, 40, 50, 60, 70, 80, 90, 100, or more nucleotides (including all intervening integers). It will be understood by those in the art that the number of nucleotides that can be subtracted from a sequence to result in a fragment will depend on the number of nucleotides in the sequence, for example, more fragment sizes can be obtained from a polynucleotide having nucleic acid sequence that is 2000 nucleotides in length than can be obtained from a polynucleotide having a nucleic acid sequence that is 100 nucleotides in length. In certain embodiments of the invention, a polynucleotide fragment includes between 4 and "n" minus one nucleotides of the nucleic acid sequence having "n" nucleotides set forth herein, or a variant thereof.

To determine the percent similarity/identity of two polynucleotides the nucleic acid sequences of the polynucleotides can be aligned for optimal comparison purposes (e.g., gaps may be introduced in the sequence of one polynucleotide for optimal alignment with the other polynucleotide). The nucleotide residues at corresponding positions are then compared. When a position in one sequence is occupied by the same nucleotide residue as the corresponding position in the other sequence (e.g., a variant form of the *V. parahaemolyticus* sequence), then the molecules have identity at that position. The percent identity between the two sequences is a function of the number of identical positions shared by the sequences (i.e., % similarity=number of identical positions/total number of positions×100). Such an alignment can be performed using any one of a number of well-known computer algorithms designed and used in the art for such a purpose. In some aspects of the invention, a variant of a polynucleotide comprises a fragment of the polynucleotide. In certain aspects of the invention, a variant of a polynucleotide is or comprises a portion of the polynucleotide's nucleic acid sequence that has at least 85%, 90%, 95%, 97%, 98%, 99%, or 100% sequence identity to the corresponding region of the polynucleotide's nucleic acid sequence when the sequences are aligned. For example, a polynucleotide fragment that is 20 nucleotides in length may have 100% identity with the nucleic acid sequence of a polynucleotide that is 200 nucleotides in length if all 20 nucleotides have identical positions shared by the sequences (e.g., are identical across the corresponding region) when the two polynucleotide sequences are aligned. Similarly, the sequence of a polynucleotide fragment that is 20 nucleotides long has identity of at least 90% to a nucleic acid sequence of a polynucleotide that is 200 nucleotides long if 18, 19, or 20 of the 20 nucleotides of the fragment are the same in the corresponding region of the nucleic acid sequence of the 200 nucleotide polynucleotide when the nucleic acid sequences of the fragment and the 200 nucleotide polynucleotide are aligned.

Polynucleotide fragments that may be useful in some embodiments of the invention may be primers or probes. Non-limiting examples of primer or probe sequences that may be useful in some embodiments of the invention are set forth herein as SEQ ID NOs: 2-7, 9, 10, 12-14, 16, 17, 19, 20, 36, 37, and other sequences set for in Tables 2 and 3, or complements thereof, some of which are set forth herein as SEQ ID Nos: 49, 50, 55, 56, 61, 62, etc. Those skilled in the art will understand how to determine a complement sequence using standard methods. In certain embodiments a primer sequence may also include additional elements, for example, though not intended to be limiting: a tag, detectable label, identifying sequence for purification, visualization, additional nucleotides, etc.

An isolated polynucleotide useful in methods of the invention can be created by introducing one or more nucleotide substitutions, additions, or deletions into a nucleic acid sequence such as, but not limited to, SEQ ID NO: 1, 8, 11, 15, 18, and 38, sequences set forth herein of the ST36end locus, ST34reg locus, ST674hyp locus, ST1127hyp locus, other polynucleotide sequence provided herein; or fragments thereof. Mutations can be introduced into the sequences by standard techniques, such as site-directed mutagenesis and PCR-mediated mutagenesis. The following examples are provided to illustrate specific instances of the practice of the present invention and are not intended to limit the scope of the invention. As will be apparent to one of ordinary skill in the art, the present invention will find application in a variety of compositions and methods.

EXAMPLES

Example 1

Identification of strains as ST36 currently requires costly and time-consuming DNA isolation, PCR amplification and sequencing of 7 housekeeping loci; however, a subset of the loci informs whether isolates are likely to be or are related to ST36. From among 94 clinical isolates from infections reported in Massachusetts, N.H., and Maine between 2010-2013, during which time infections from the ST36 strain were first reported from Atlantic sources [Martinez-Urtaza J, et al., (2013) N Engl J Med 369:1573-1574], 43 isolates were identical to ST36 at four housekeeping loci (dnaE, dtdS, pntA and tnaA) [González-Escalona N, et al., (2008) J Bacteriol 190:2831-2840]. The relationships of these probable ST36 isolates to 47 of the remaining clinical isolates from the region was determined by constructing a neighbor-joining tree of the concatenated and aligned sequences [Tamura K, et al. (2013) Mol Biol Evol 30:2725-2729] (FIG. 1). This identified three additional isolates that were related to but distinct from the ST36 clade. The analysis of all seven housekeeping loci using Illumina whole genome short reads from four probable ST36 isolates, including MAVP-26 (SAMN03107383), MAVP-36 (SAMN03107385), MAVP-45 (SAMN03177810) and MAVP-V (SAMN03177809) obtained from the Hubbard Center for Genome Studies at the University of New Hampshire, confirmed that these isolates are ST36 [Inouye M, et al., (2012) BMC Genomics 13:338; Jolley K. (2010) Database:pubmlsthttp://pubmlst.org/vparahaemolyticus/info/protocol.shtml. Accessed 1 Feb. 2013].

To identify genomic differences for use in a ST36-diagnostic assay, whole genome comparisons were performed between the published draft genome for serotype O4:K12 ST36 strain 10329 (the 33 contigs including NZ_AFBW01000001.1-33.1) [Gonzalez-Escalona N, et al., (2011) J Bacteriol 193:3405-3406] and the genomes of two other pathogenic strains, including the pandemic strain RIMD 2210633 (NC 004605.1, NC 004603.1) [Makino K, et al, (2003) The Lancet 361:743-749] and pre-pandemic strain BB22OP (NC 019955.1, NC 019971.1) [Jensen R V, et al., (2013). Genome Announce 1:e00002-00012]. The unique genome content was visualized [Alikhan N-F, et al., (2011) BMC Genomics 12:402 DOI:410.1186/1471-2164-1112-1402; Darling A C, et al., (2004) Genome Res 14:1394-1403] and re-annotated using a Vibrio sp. specific database in NCBI with Prokka 1.8 [Seemann T. (2014) Bioinformatics: DOI:10.1093/bioinformatics/btu1153]. Few coding regions (~six) in three different contigs appeared unique to strain 10329. It was then determined the extent the ORFs within these regions were present in and potentially exclusive to all strains in the 10329 genome group based on comparisons with draft genomes of V. parahaemolyticus available at the time of this analysis (289 total) (www.ncbi.nlm.nih.gov/genome/691), accessed Oct. 12, 2014) [Altschul S F, et al., (1997). Nucl Acids Res 25:3389-3402].

ORFs that were absent from more than one high-quality draft genome of the 10329 genome group (not all of which are ST36), or that were present in many other genome groups were eliminated from further consideration thereby focusing further analysis on two different regions of contig 10329_28 that were also present in the four Northeast regional ST36 isolates. ST36 diagnostic loci were identified. Genomic were identified, including regions that were present in 10329_28 of strain 10329 and in Northeastern ST36 isolates, including MAVP-V, MAVP-26, MAVP-36 and MAVP-45, but that were absent in pandemic and pre-pandemic strains including the prp, cps and O-antigen flippase (flp) genes. From the first region in this contig, an ORF identified as a pathogenesis-related protein (locus prp) (EGF42613) based on its similarity to a single ORF in Vibrio sp. Ex25 (YP_003285914.1) was selected as a potential diagnostic locus due to its uniqueness, even outside the species.

The designation of prp was proposed for this locus even though the gene more likely encodes an endonuclease or DNA helicase based on similarity searches in NCBI [Altschul S F, et al., (1997) Nucl Acids Res 25:3389-3402] in the absence of compelling evidence for function and a different name. Two additional ORFs including one identified as encoding a capsular polysaccharide (locus cps) (EGF42671) and another as 0-antigen flippase (locus flp) (EGF42675) in a second region of the same contig were also identified as diagnostic targets due to their potential role in conferring the O4 antigenic property of the strain, which is a useful diagnostic phenotype.

Figure 2:
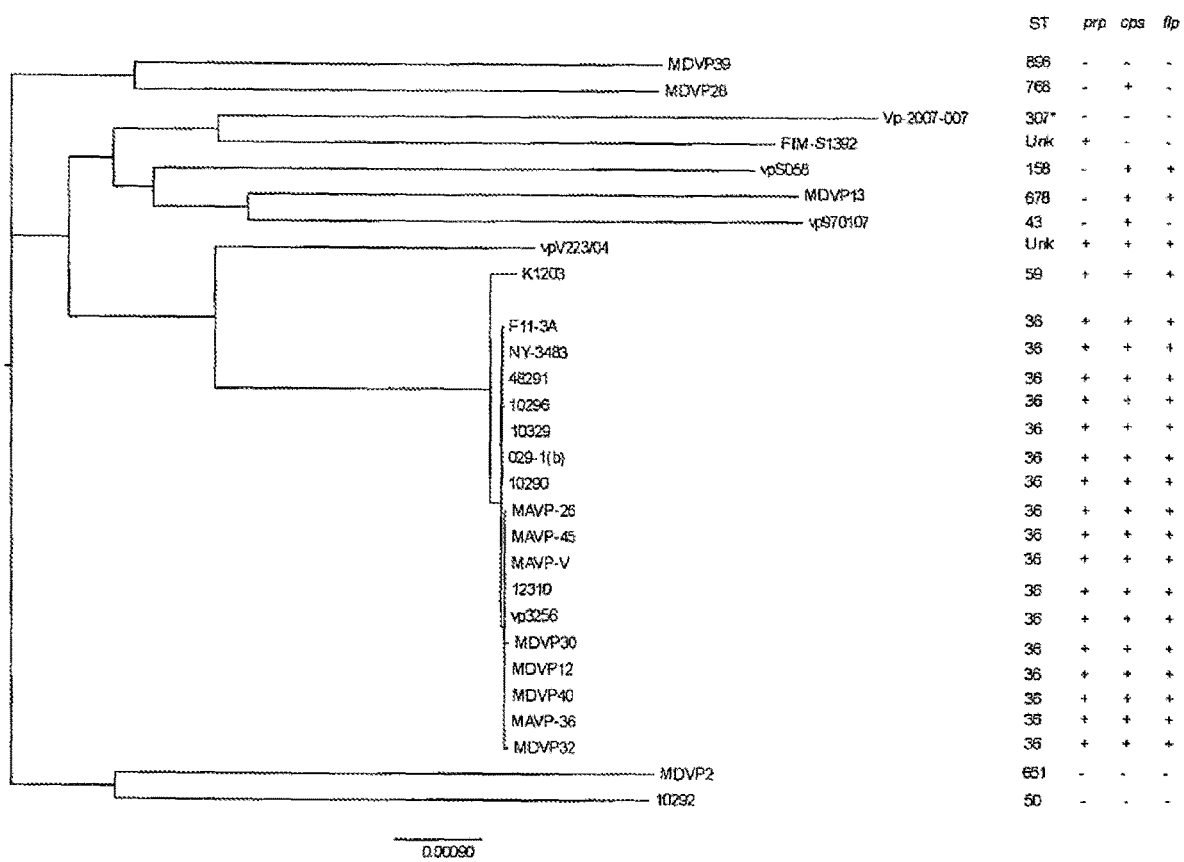
FIG. 2 provides a diagram showing the distribution of putative diagnostic loci in ST36 and related strains. Multiple genome reference-sequence alignment based phylogenies using three high quality genomes including ST36 isolate 10290 (NZ_AVOH01000000), BB22OP, and RIMD 2210633 as references were reconstructed using REALPHY v1.09 with a representative sub-set of sequenced isolates where the merged alignment represents 75% coverage of sites of the largest reference genome (10290). The distribution of each of three potentially diagnostic genes is represented by (+) for gene present, and (−) for gene absent. The distribution of these loci in all available draft genomes is indicated in FIG. 4. Note that in FIG. 4, isolate VP-2007-007 was identified as ST 306 using the SRST2 program [Inouye M, et al., (2012). *BMC Genomics* 13:338].

To determine the extent that one or a combination of these loci are present only in strains closely related to ST36, multiple reference whole genome phylogenies were constructed with REALPHY v. 1.09 for a few high quality genomes from each NCBI genome group lineage that harbored at least one of the three loci under evaluation, and for strains branching relatively closely with the 10329 genome group (www.ncbi.nlm.nih.gov/genome/?term=vibrio%20parahaemolyticus) [Bertels F, et al., (2014) Mol Biolo Evol 31:1077-1088] (see FIG. 2). This phylogeny is based on a subset of high quality genomes compared to NCBI BLAST phylogeny, thereby using a higher proportion of informative sites. The three identified genes only co-occur in ST36, closely related ST59 and one single other related strain (vpV223/04) of unknown sequence type (see FIG. 2, FIG. 4).

Only one high quality genome (MDVP13, ST678) in the 10329 genome group apparently lacks prp (see FIG. 2, FIG. 4). Five other genomes harbored one or two of the three loci. These include strains in four different NCBI genome groups (NIHCB0757, S159, S048, and SNUVpS-1) but not every strain in these genome groups harbored these genes. Based on its distribution and uniqueness, prp is likely sufficient for strain identification. It was reasoned that due to the complexity of serotypes within the ST36 clade, potential selection upon the locus that could produce variation [Banerjee S K, et al., (2014) J Clin Microbiol 52:1081-1088], and the occurrence of cps and/or flp in four more distantly related strains (FIG. 4), these may be used alone or in combination with each other and/or with prp. A combination prp with just one other locus (i.e. cps or flp) may be especially accurate.

Oligonucleotide primers that produce prp-, cps- and flp-specific amplicons were developed for simultaneous detection along with both hemolysin-encoding genes (tdh and trh)

and the species specific locus (tlh) to improve an existing multiplex PCR assay [see for example: Panicker G, et al., (2004) Appl Environ Microbiol 70:7436-7444 and J. L. Nordstrom, et al., App Environ Microbiol (2007) 73:5840-5847]. Table 2 shows non-limiting examples of primers utilized in PCR amplifications.

Alignments of 29 available prp sequences [Tamura K, et al., (2013) Mol Biol Evol 30:2725-2729] allowed identification of regions of high sequence identity, which informed primer design to produce optimal amplicon size separation with the existing multiplex PCR amplicons. Secondary structure and primer cross-dimerization were minimized by design with the aid of the NetPrimer program (PREMIER Biosoft, CA, US). A similar strategy was used to design the cps and flp-specific PCR. Amplification of the prp locus was evaluated in individual and multiplex assays using genomic DNA from positive (F11-3A), and negative (G61) [Mahoney J C, et al., (2010) Appl Environ Microbiol 76:7459-7465; Ellis, C N, et al., (2012) Appl Environ Microbiol 78:3778-3782] control strains using AccuStart PCR Supermix (Quanta, Md., US) with an initial denaturation at 94° C. for 3 minutes, followed by 30 cycles with a denaturation at 94° C. for 1 minute, primer annealing at 55° C. for 1 minute, and extension at 72° C. for 1 minute, and with a final extension at 72° C. at the completion of the cycling for 5 minutes.

Amplicons from the amplifications were evaluated using standard procedures, for example: by electrophoresis of 1.5 µl of sample on 1.2% SeaKem LE agarose (Lonza, Rockland, Me., USA) gel with 1× GelRed (Phenix Research Products, Candler, N.C., USA) in Tris-acetate-EDTA (TAE) buffer compared against a 1-kb Plus DNA ladder (Invitrogen, Grand Island, N.Y., USA).

Figure 3:
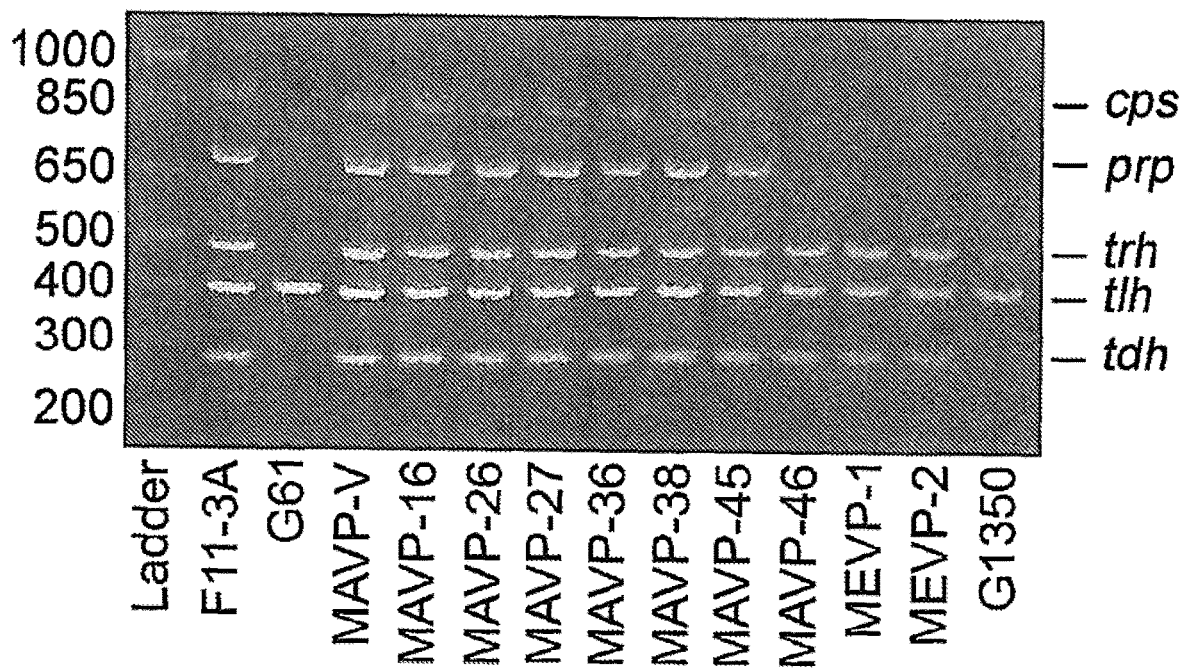
FIG. 3 shows a photographic image of an agarose gel demonstrating results of a multiplex PCR assay for identification of ST36 *V. parahaemolyticus*. The presence of virulence or strain-associated amplicons including tdh, trh, prp (using ST36prp-3 primers) and cps, and the species specific marker tlh on a subset of ST36 clade members, and isolates identified from adjacent, related clades using published and newly designed primers (Table 2) were visualized on a 1.2% SeaKem LE agarose (Lonza, Rockland, Me. USA) gel, with 1× Gelred (Phenix Research Products, Candler, N.C. USA) in TAE buffer, compared with 1 Kb Plus DNA Ladder (Invitrogen, Grand Island, N.Y. USA).

The developed assay was also applied to the collection of 94 clinical strains and several closely related environmental strains (i.e. G1350) from the Northeast. The prp amplicon was detected in all 43 strains that grouped within the ST36 clade and no other clinical or environmental isolates from northern New England, even the three strains identified as most closely related to the ST36 clade (FIG. 3). A subset of prp-positive and -negative strains was subsequently analyzed for the presence of cps, which was also only detected in ST36 clade strains (FIG. 3).

These data indicate that the presence of the prp amplicon is diagnostic for ST36 complex strains, and that the cps (or flp) amplicon could further enhance accuracy of identification. Not only was the assay useful for clinical identification, but it should also aid in surveillance. It will help determine the extent of this strain's geographic expansion, establishment of stable local populations and the seasonal dynamics of these strains, thereby aiding in management of shellfish harvesting and reducing public health risk.

Example 2

Specific Identification of Strains by Sequence Type Using PCR

In addition to ST36, several other sequence types have contributed to the rise in infections, and have been recovered from shellfish harvest areas suggesting they are not transient but resident pathogens in harvest areas. ST631 has caused infections from Atlantic harvest areas from FL to PEI Canada, and currently accounts for ~10% of infections from Gulf of Maine sources. ST34 (and closely related ST324), ST674, and ST1127 are more rarely detected in harvest areas and cause fewer infections but may be emergent types. All five of these strain types carry the same pathogenicity island harboring both tdh and trh.

A similar approach to that described for identifying sequence-type (ST)-specific genetic loci for the invasive ST36 strain, (See Example 1; and Whistler et al, 2015), was used to develop a detection process for additional pathogenic lineages. Whole genome sequence comparisons were conducted, and using BLAST Ring Image Generator (BRIG) and Multiple Alignment of Conserved Genomic Sequence With Rearrangements (MAUVE), highly unique regions were visualized, located, and compared to various reference genomes. To ensure identified DNA was uniquely present only in specific lineages (or Sequence Types), BLAST and alignment comparisons were carried out using the NCBI database of all complete and draft genomes. Primers were designed (See Table 2 for invented strain identification primers) and evaluated using PCR amplification methods for specificity and accuracy on a collection of several hundred unique isolates, and the expected high degree of specificity/accuracy was confirmed.

Methods

Amplification

PCR amplifications were performed with AccuStart PCR Supermix (Quanta, Gaithersburg, Md., US) with an initial denaturation at 94° C. for 3 minutes, followed by 30 cycles with a denaturation at 94° C. for 1 minute, primer annealing at 55° C. for 1 minute, and extension at 72° C. for 1 minute, and with a final extension at 72° C. at the completion of the cycling for 5 minutes. Altered extension times were also used as appropriate. For example, Table 2 provides PCR annealing temps and indicates certain primer pairs for which a 1.5 min extension time was used. For example, in multiplex assays, a 1.5 min extension time was used when multiple amplifications were performed in the same cycler. As noted in Table 2, the extension time used for the TdhUreG primer pair was 3 minutes. Standard procedures to optimize PCR amplifications were used.

For the locus PCR amplifications, the amplicon length determined the length in time of the PCR extension reaction, which was 1 Kb per minute. All of the reactions were 3 minutes or less and most were 1 minute. The annealing temperatures used were one degree below the melt temperature. If two primer pairs were used in multiplex, the lower annealing temperature of the primers was used. For example, if the annealing for one was 55° and the other 57°, the 55° temperature was used.

Amplicon Detection

Amplicons from the amplifications were evaluated using standard procedures, for example: by electrophoresis of 1.5 µl of sample on 1.2% SeaKem LE agarose (Lonza, Rockland, Me., USA) gel with 1× GelRed (Phenix Research Products, Candler, N.C., USA) in Tris-acetate-EDTA (TAE) buffer compared against a 1-kb Plus DNA ladder (Invitrogen, Grand Island, N.Y., USA).

Figure 5:
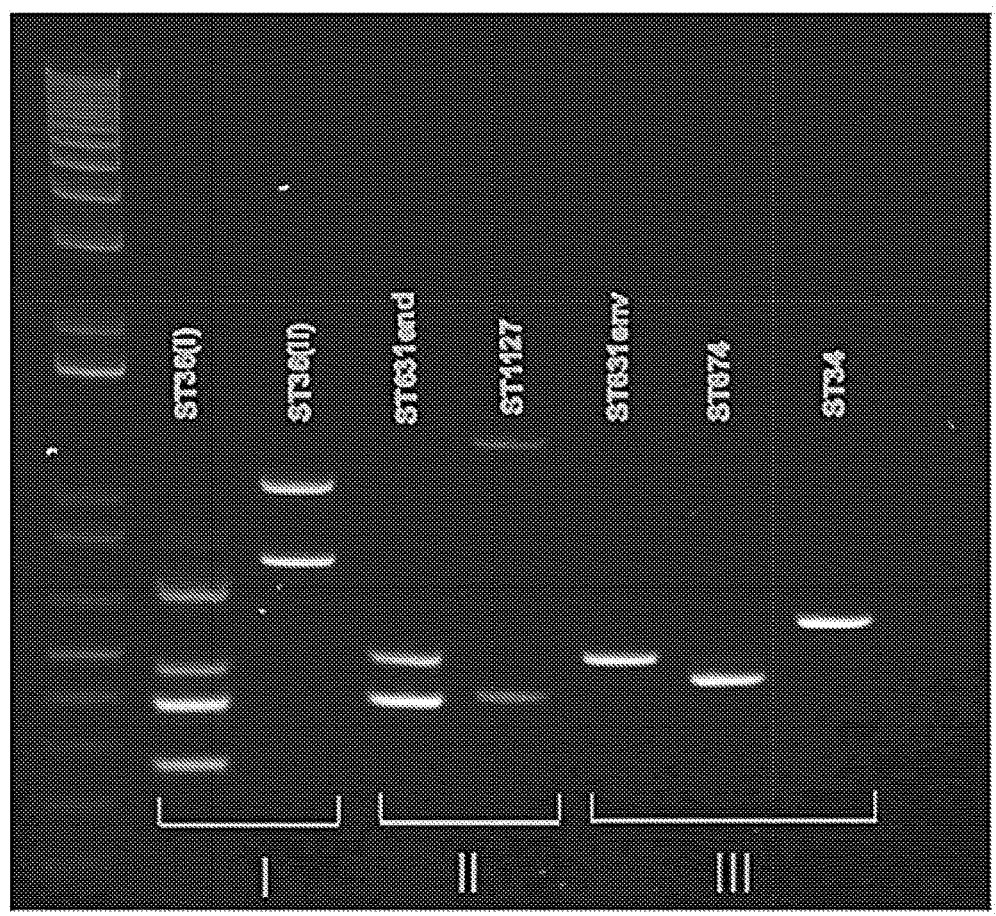
FIG. 5 provides a photographic image of a gel showing results from three PCR reactions, identified in the image as: a PCR reaction I, PCR reaction II, and PCR reaction III. The reactions were used identify pathogen sequence types using PCR. Results shown in the left lane of the PCR Reaction I gel lanes, identify ST36(I) products obtained using multiplex PCR using the prp3 and cps primers, with the expected 5 amplicons. The right lane of PCR Reaction I gel lanes shows results that provide secondary confirmation obtained using multiplex prp2 and flp primers. Results shown in PCR reaction II gel lanes identify ST631 (left) and ST1127 (right) obtained using multiplex, including the tlh control PCR (tlhF2/R). Results shown in the PCR reaction III gel lanes identify ST674 (left lane) and ST34 (right lane) (including a secondary confirmation of ST631 with a less specific amplicon ENV). See Table 2 for primer sequence information.

Additional studies have been performed using multiplex amplification methods including a tiered approach for strain identification in which the first round was the 5-amplicon (tlh/tdh/trh/prp3/cps) amplification, which was then double checked with prp2/flp amplification from the sample (see FIG. 5, PCR Reaction I). Then any isolate that was found to be not positive for ST36 in PCR Reaction I assay, was tested with other primers together for the other isolates, such as ST631 and ST1127 (see FIG. 5, PCR Reaction II and PCR Reaction III). FIG. 5 shows results from the assays.

Example 3

Enumeration of ST36 and ST631 by Quantitative PCR-Based Most Probable Number (MPN) Methods In order to use these specific loci for quantification of pathogenic *Vibrio parahaemolyticus*, qPCR assays were designed that are compatible with the currently employed FDA protocol designed by J. Jones (Nordstrom et al. 2007) and based on the Bacteriological Analytical Manual (see fda.gov/Food/FoodScienceResearch/LaboratoryMethods/ucm2006949.htm). Table 3 herein provides a list of oligonucleotide primers used for pathogen quantification.

Methods

Amplification Conditions

Amplification methods were designed and optimized as needed using routine optimization procedures. For example, cycling was based on the length of the amplicon and annealing was based on temperature of melting. Table 3 provides locus information, primer sequences, and melting temperatures for the primers used in qPCR procedures. Table 3 also provides sequences of probes and some examples of detectable labels that were used. The Quanta ToughMix (Quanta Biosciences Inc, Gaithersburg, Md.) was used (according to manufacturer's instructions) for multiplex amplifications with primers for prp, flp, and end. The cycling parameters were as follows:

Cycle 1: 95° C. hold for 60 s (this was increased as necessary depending on enzyme used) Cycle 2 (45 times):
95° C. for 5 s
59° C. for 45 s.

Assay Steps

The MPN protocol of Nordstrom uses a two-step enumeration: In step one, enriched oyster homogenate lysates are evaluated for the presence of *V. parahaemolyticus* by detection of tlh with an internal amplification control IAC and in step two, lysates that are positive for *V. parahemoltyicus* are subsequently evaluated for the presence of two virulence associated markers, including tdh and trh (with the IAC control) allowing the determination of the most probable number of these bacteria per gram of oyster.

Studies that were performed identified that a major limitation of the Nordstrom test was that these markers are present in environmental strains that are likely not pathogenic, and the markers are absent in some clinical strains so they are associated with virulence, but are not very useful for predicting the abundance of specific pathogen type strains.

Experiments were performed to develop a more specific detection strategy that can be added to this widely used platform and/or with other testing described herein, to improve risk assessment by specific quantification of the two strains that cause a predicted 85% of the cases from Atlantic harvest areas in the US. ST36 also causes more than 50% of the cases from the Pacific harvest areas of the US.

Experiments were carried out and a third assay step was developed. Studies were performed to evaluate lysates (samples) that were positive for either tdh or trh, and if found to be positive for one or both, the samples were further tested for the presence of ST36 by targeted amplification of both prp and flp, and for ST631 by the targeted amplification of end using probes and primers designed to these loci (Table 3), using qPCR amplification methods.

The probes were fluorescently labeled (see label information in Table 3) and they attached to the loci and when the primers amplified the sequence it released the quencher from the fluorofor, which was detected. These assays can also be performed using the detectable label: SYBR green or other detectable labels incorporated in the amplicon or linked to the probes, as indicated in Table 3 and elsewhere herein. Evaluation and quantitation of amplicons was performed using standard methods and manufacturer's instructions.

The developed PCR reactions were compatible with the FDA-required IAC internal control. Presence of these pathogenic bacteria in the lysates was further confirmed by use of the strain specific PCR primers by end-point binary PCR (Table 2) including the cps locus, and the prp2 primer pair for validation, and ST631-ENV or end primers.

Other types of qPCR assays that were carried out included a combined qPCR detection of prp, flp, and end polynucleotides. In the assays, an initial step included one cycle of tlh/IAC amplification/detection, and if results were positive a next step was to amplify and detect tdh/trh/IAC, which was followed by a third step of amplifying and detecting prp/flp/end/IAC.

Example 4

Figure 6:
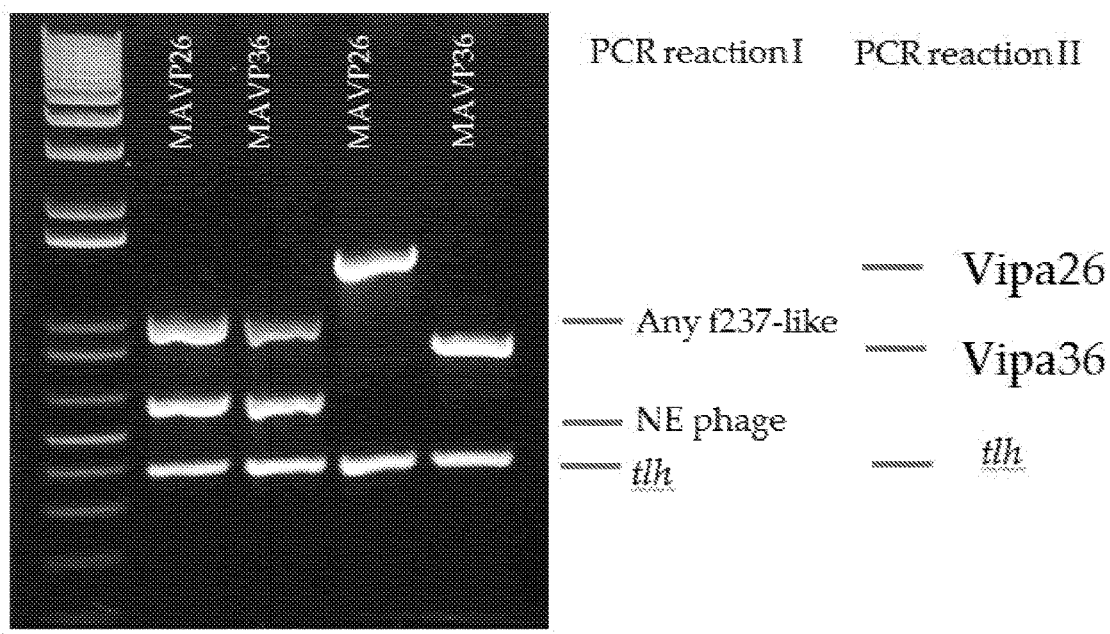
FIG. 6 provides a photographic image of a gel showing results from two PCR reactions, labeled in the image as PCR reaction I and PCR reaction II. In the experiments, PCR was used in the identification of *V. parahaemolyticus* sequences. The results for PCR reaction I show: bands at: tlh (tlhF2/tlhR primers), NE Phage (ST36NEOrf10F/ST36NEHypR primers), any f237-like phage (ST36PhageF2/R2 primers). The results for PCR reaction II show: tlh (tlhF2/tlhR primers), Vipa 26 and Vipa 36 size difference (ST36PhHypDF3/ST36PhOrf9R1 primers). See Table 2 for sequence information for primers.

Identification of Sub Populations of ST36 that are Localized to the Gulf of Maine (Vipa-26 Marker) or Katama Bay of Martha's Vineyard (Vipa-36 Marker) and Invention of a Population Marker Based PCR Whole genome phylogenies revealed that there were distinctive lineages with diagnostic characteristics of the populations in the Gulf of Maine, for Katama Bay of Martha's Vineyard that would allow traceback of isolates. The unique attributes were the presence of phage Pathogenicity Islands: Vipa-26 in the Gulf of Maine, and Vipa-36 only in Katama Bay. Experiments were performed and a detection assay that included PCR amplification processes for specific identification of strains by population/harvest areas was developed. Following application of the multiplex PCR (see Example 1 and Whistler et al., 2015), isolates that were positive for the ST36 marker were subsequently analyzed for the presence of f237-like or Vipa-like phage, followed by a PCR reaction that distinguished the Gulf of Maine, and Katama Bay population by size difference of the amplicon (see FIG. 6). PCR reactions were performed that included: PCR reaction I: to test for presence of tlh (tlhF2/tlhR primers, see Table 2), NE Phage (ST36NEOrf10F/ST36NEHypR primers, see Table 2), any f237-like phage (ST36PhageF2/R2 primers, see Table 2). Additional PCR was performed that included PCR reaction II: that tested for the presence of tlh (tlhF2/tlhR primers, see Table 2), Vipa 26 and Vipa 36 size difference (ST36PhHypDF3/ST36PhOrf9R1 primers, see Table 2). These primers were validated on the entire University of New Hampshire (UNH) collection of clinical strains, and these markers were identified as present only in ST36 clinical strains isolated from these two locations, and to be absent in all other clinical strains (including those in the NCBI database). For a list of primers, see Table 2. For amplification conditions see Examples 1 and 2).

Example 5

Identification of a Shared Pathogenicity Island Architecture Among Tdh/Trh Positive Pathogens of Several Sequence Types (ST36, ST631, ST34/324, ST674, ST1127, ST749, and ST110), and Invention of PI-Hybrid Marker Based PCR Through the application of PacBio genome sequencing and highly accurate genome assembly, it was identified that the major emergent and invasive pathogenic strains of *V. parahaemolyticus* harboring both tdh and trh share a previously undiscovered hybrid pathogenicity island architecture. The unique feature of the island is the presence of a smaller tdh island flanked by transposases that have integrated within the major pathogenicity island containing the urease cluster, trh, and type three secretion beta genes that are implicated in defining virulence. It was identified that it is not simply the presence of the tdh and trh genes in the genomes that is characteristic, but the synteny or architecture of these elements within the same island. Therefore a strategy was developed whereby all strains with this specific island architecture could be detected by PCR amplification through the juncture of these two islands from tdh to ureG and detection, for example, by electrophoresis.

Figure 7:
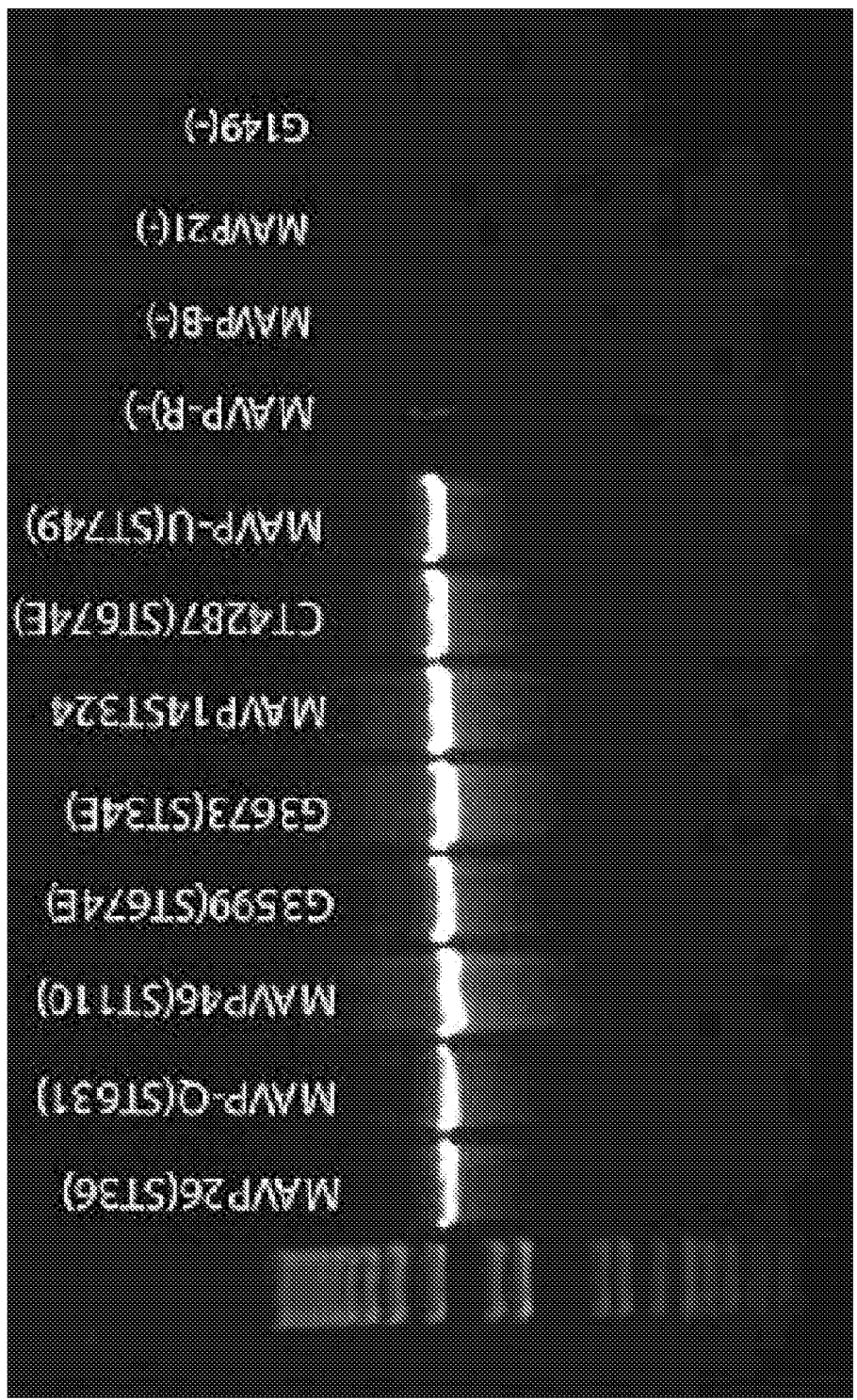
FIG. 7 is a photographic image of a gel showing results of amplifications demonstrating a shared pathogenicity island architecture among tdh/trh positive pathogens of several sequence types include in the eight lanes from left to right: ST36, ST631, ST110, ST674, ST34, ST324, ST674 and ST749 and is not present in the non-pathogenic strains and non-regional pathogenic sequence types that lack the island shown in the four right-hand lanes of the gel.

FIG. 7 shows results amplifications of the identified island region. The results demonstrated that there is a shared pathogenicity island architecture among tdh/trh positive pathogens of several sequence types including, ST36, ST631, ST1110, ST674, ST34, ST324, ST674 and ST749. The results showed that the pathogenicity island architecture was not present in non-pathogenic strains, and strains that lack the island, as shown by the lack of the product in the four right-hand lanes of the gel.

The primers used in the PCR amplification are the primers listed in Table 2 as TdhUreG. The forward primer, SEQ ID NO:100, anneals to tdh gene, the reverse primer, SEQ ID NO: 101, anneals to ureG, and this unique juncture is the pathogenicity island. The region amplified is the region is this unique island. The reaction conditions are also provided in Example 1 and 2 herein with additional detail in Table 2. PCR amplifications were performed with AccuStart PCR Supermix (Quanta, Gaithersburg, Md., US) with an initial denaturation at 94° C. for 3 minutes, followed by 30 cycles with a denaturation at 94° C. for 1 minute, primer annealing at 55° C. for 1 minute, and extension at 72° C. for 3 minutes, and with a final extension at 72° C. at the completion of the cycling for 5 minutes.

Amplicons from the amplifications were evaluated using standard procedures, for example: by electrophoresis of 1.5 μl of sample on 1.2% SeaKem LE agarose (Lonza, Rockland, Me., USA) gel with 1× GelRed (Phenix Research Products, Candler, N.C., USA) in Tris-acetate-EDTA (TAE) buffer compared against a 1-kb Plus DNA ladder (Invitrogen, Grand Island, N.Y., USA).

In the gel shown in FIG. 7, the actual strain number is listed first, and then the sequence type is in brackets. The presence of the "E" after the sequence type indicates that the sample was obtained from the environment such as an oyster. ST324 is a very close relative of ST34, and both are pathogens. ST674E is a pathogen type, ST749 is a clinical strain and also pathogen type; and ST110 is a pathogen. The last four lanes are strains that don't have the island and they are also negative. These last four lanes demonstrated that the strains that were not expected to amplify, did not amplify

EQUIVALENTS

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated in their entirety herein by reference.

What is claimed is:

1. A method of identifying the status of a pathogenic *V. parahaemolyticus* in a sample obtained from a subject or substrate, the method comprising:
   (a) detecting in the sample a level of at least one ST36prp polynucleotide comprising (i) the nucleic acid sequence of SEQ ID NO: 1, or a variant thereof having at least 99% sequence identity to the nucleic acid sequence of SEQ ID NO: 1, or (ii) the nucleic acid sequence of SEQ ID NO: 2, 3, 4, 5, 6, 7, 21, 22, 23, 24, 25, 26, 127, 128, 129, or 130, or a variant thereof having at least 94% sequence identity to the nucleic acid sequence with SEQ ID NO: 2, 3, 4, 5, 6, 7, 21, 22, 23, 24, 25, 26, 127, 128, 129, or 130, respectively;
   (b) comparing the level of the detected ST36prp polynucleotide to a control level of the detected ST36prp polynucleotide;
   (c) detecting in the sample at least one of
   (i) a ST36cps polynucleotide comprising (A) the nucleic acid sequence of SEQ ID NO: 8, or a variant thereof having at least 99% sequence identity to the nucleic acid sequence of SEQ ID NO: 8, or (B) the nucleic acid sequence of SEQ ID NO: 9, 10, 27, or 28 or a variant thereof having at least 94% sequence identity to the nucleic acid sequence with SEQ ID NO: 9, 10, 27, or 28, respectively; and
   (ii) a ST36flp polynucleotide comprising (C) the nucleic acid sequence of SEQ ID NO: 38, or a variant thereof having at least 99% sequence identity to the nucleic acid sequence of SEQ ID NO: 38, or (D) the nucleic acid sequence of SEQ ID NO: 36, 37, 39, 40, 143, or 144, or a variant thereof having at least 94% sequence identity to the nucleic acid sequence with SEQ ID NO: 36, 37, 39, 40, 143, or 144, respectively;
   (d) identifying the subject or substrate as including pathogenic *V. parahaemolyticus*, wherein a higher level of the at least one ST36prp polynucleotide detected in the sample compared to the ST36prp polynucleotide control level and at least one of the ST36cps polynucleotide and the ST36flp polynucleotide detected in the sample identifies the sample as including the pathogenic *V. parahaemolyticus* and identifies the subject or substrate as having *V. parahaemolyticus* infection and *V. parahaemolyticus* contamination, respectively,
   (e) selecting a therapeutic regimen or decontamination regimen appropriate to treat the *V. parahaemolyticus* infection in the identified subject or to decontaminate the *V. parahaemolyticus* contamination of the identified substrate, respectively; and
   (f) administering the selected therapeutic regimen or decontamination regimen to the identified subject or substrate, respectively.

2. The method of claim 1, the method further comprising:
   (g) comparing the level of the detected ST36cps polynucleotide to a control level of the detected ST36cps polynucleotide; and
   (h) identifying the status of the pathogenic *V. parahaemolyticus* us in the sample based at least in part on the difference between the level of the detected ST36cps polynucleotide and the control level of the detected ST36cps polynucleotide.

3. The method of claim 2, wherein a higher level of the detected ST36cps polynucleotide compared to the control level of the detected ST36cps polynucleotide identifies the status of the pathogenic *V. parahaemolyticus* as present in the sample.

4. The method of claim 1, further comprising:
   (g) comparing the level of the detected ST36flp polynucleotide to a control level of the detected ST36flp polynucleotide; and
   (h) identifying the status of the pathogenic *V. parahaemolyticus* in the sample based at least in part on a difference between the level of the detected ST36flp polynucleotide and the control level of the detected ST36flp polynucleotide.

5. The method of claim 4, wherein a higher level of the detected ST36flp polynucleotide compared to the control level of the detected ST36flp polynucleotide aids in identifying the status of the pathogenic *V parahaemolyticus* in the sample.

6. The method of claim 1, wherein the substrate comprises one or more of a liquid wherein the liquid optionally comprises water; one or more of a metal, wood, plastic, glass, cork, fiber, a polymer, or a fabric; a food substance, and wherein the food substance optionally comprises shellfish; at least a portion of a tool, work surface, a medical device, body of water, clothing, skin, tissue, an edible substance, a beverage, or a food; and a fluid sample, semisolid sample, aqueous sample, or tissue sample.

7. The method of claim 1, further comprising:
   (g) detecting in the sample a level of a tdh polynucleotide comprising the nucleic acid sequence set forth as SEQ ID NO:15, or a variant thereof having at least 99% sequence identity to the nucleic acid sequence of SEQ ID NO: 15; and
   (h) comparing the level of the detected tdh polynucleotide to a control level of the detected tdh polynucleotide, wherein a higher level of the detected tdh polynucleotide compared to the control level of the detected tdh polynucleotide aids in identifying the status of the pathogenic *V. parahaemolyticus* in the sample.

* * * * *